(12) United States Patent
Lorentsen et al.

(10) Patent No.: US 10,550,375 B2
(45) Date of Patent: Feb. 4, 2020

(54) POLYPEPTIDE HAVING XYLANASE ACTIVITY

(71) Applicant: DuPont Nutrition Biosciences ApS, Copenhagen K (DK)

(72) Inventors: Rikke Hoeegh Lorentsen, Randers (DK); Susan Arent Lund, Braband (DK); Svend Haaning, Galten (DK); Igor Nikolaev, Nordwijk (NL); Sharief Barends, Voorschoten (NL); Jan Hendrick A Van Tuijl, Zoetermeer (NL); Bart Koops, Pijnacker (NL)

(73) Assignee: DuPont Nutrition Biosciences ApS, Copenhagen K (DK)

(*) Notice: Subject to any disclaimer, the term of this patent is extended or adjusted under 35 U.S.C. 154(b) by 180 days.

(21) Appl. No.: 15/116,281

(22) PCT Filed: Jan. 30, 2015

(86) PCT No.: PCT/EP2015/051979
§ 371 (c)(1),
(2) Date: Aug. 3, 2016

(87) PCT Pub. No.: WO2015/114110
PCT Pub. Date: Aug. 6, 2015

(65) Prior Publication Data
US 2017/0009220 A1    Jan. 12, 2017

(30) Foreign Application Priority Data
Jan. 31, 2014  (GB) .................................. 1401699.2

(51) Int. Cl.
| | |
|---|---|
| *C12N 9/24* | (2006.01) |
| *C12C 5/00* | (2006.01) |
| *C12P 19/14* | (2006.01) |
| *A23K 20/189* | (2016.01) |
| *A61K 38/47* | (2006.01) |
| *C12C 7/01* | (2006.01) |
| *C12P 19/04* | (2006.01) |

(52) U.S. Cl.
CPC .......... *C12N 9/2482* (2013.01); *A23K 20/189* (2016.05); *A61K 38/47* (2013.01); *C12C 5/004* (2013.01); *C12C 7/01* (2013.01); *C12P 19/04* (2013.01); *C12P 19/14* (2013.01); *C12Y 302/01008* (2013.01)

(58) Field of Classification Search
None
See application file for complete search history.

(56) References Cited

FOREIGN PATENT DOCUMENTS

| | | |
|---|---|---|
| WO | 2003046169 A2 | 6/2003 |
| WO | WO-2014081884 A1 * | 5/2014 ............. A61K 38/16 |

OTHER PUBLICATIONS

Kimura et al. "Molecular cloning, characterization, and expression analysis of the xynF3 gene from Aspergillus oryzae." Bioscience, biotechnology, and biochemistry 66.2 (2002): 285-292. (Year: 2002).*
Bornscheuer et al. "Engineering the third wave of biocatalysis." Nature 485.7397(2012):185 (Year: 2012).*
NCBI Protein Database, entry for beta-1,4-xylanase [Aspergillus oryzae 3.042], entered on Jun. 18, 2012, webpage accessed Nov. 9, 2018 (Year: 2012).*
NCBI Blast Protein Alignment, Basu sequence Seq ID No. 996 (Query) of with Kimura sequence of Fig. 2 (Subject), webpage accessed May 22, 2019 (Year: 2019).*
International Search Report, PCT International Appl. No. PCT/EP2015/051979, dated August 6, 2015.
Tetsuya Kimura et al., Molecular Cloning, Characterization, and Expression Analysis of the XYNF3 Gene From Aspergillus Oryzae, Bioscience, Biotechnology and Biochemistry, vol. 66, No. 2 (2002), pp. 285-292.
Database Uniprot (Online), Retrieved From EBI Accession No. Uniprot: Q96VB6 (2001).
Database EMBL (Online), Retrieved From EBI Accession No. EM_STD: KF233755 (2013).
Digvijay Verma et al., Molecular Approaches for Ameliorating Microbial Xylanases, Bioresource Technology, Elsevier VB, GB, vol. 117 (2012), pp. 360-367.

* cited by examiner

*Primary Examiner* — Emily A Cordas

(57) ABSTRACT

The present invention relates to an isolated polypeptide having xylanase activity, selected from the group consisting of:
  a) a polypeptide comprising an amino acid sequence having at least 87% identity with SEQ ID NO: 1;
  b) a polypeptide encoded by a polynucleotide having at least 87% identity with SEQ ID NO:2; or
  c) a fragment of a polypeptide of a) or b) which fragment has xylanase activity.

17 Claims, 11 Drawing Sheets
Specification includes a Sequence Listing.

FIGURE 1

SEQ ID No. 1

>Translation of synXyn92 (24aa - 325aa) 302aa
QAAASINNAFKAHGKKYFGTCADQDTLTNPKNAAIIKADFGQLTPENSMKWDATEPSQGKFNFGGADYLV
NFAKQNGKLIRGHTLVWHSQLPSWVQNINDKNTLTKVMKNHITTVMSRYKGKIYAWDVVNEIFNEDGTLR
NSVFYNVLGEDFVRIAFETARAADPNAKLYINDYNLDSANYAKTKGMVSHVKKWIAEGIPIDGIGSQTHL
GAGGGAGVAGALNALAAAGVSEVAITELDIAGASSNDYVNVVKACLNEPKCVGITVWGVSDKDSWRSDDN
PLLFDSNYKPKAAYNAIIDALR

FIGURE 2

SEQ ID No. 2

> synXyn92 (121bp - 1098bp, direct) 978bp
ATGAAGCTCAGCTCGTTCCTCTACACCGCCAGCCTCGTCGCTGCCATCCCTACCGCTATCGAGCCCCGAC
AGGCTGCTGCCAGCATCAACAACGCCTTCAAGGCCCACGGCAAGAAGTACTTCGGCACTTGCGCCGACCA
GGACACGCTCACCAACCCCAAGAACGCCGCCATCATCAAGGCCGACTTCGGCCAGCTCACCCCCGAGAAC
AGCATGAAGTGGGACGCCACCGAGCCCAGCCAGGGCAAGTTCAACTTTGGCGGCGCTGACTACCTCGTCA
ACTTCGCCAAGCAGAACGGCAAGCTCATCCGCGGCCACACCCTCGTCTGGCACAGCCAGCTCCCTAGCTG
GGTCCAGAACATCAACGACAAGAACACCCTGACCAAGGTCATGAAGAACCACATCACCACCGTCATGAGC
CGCTACAAGGGCAAGATCTACGCCTGGGACGTCGTCAACGAGATCTTCAACGAGGACGGCACCCTCCGCA
ACAGCGTCTTTTACAACGTCCTGGGCGAGGACTTCGTCCGCATTGCCTTCGAGACTGCCCGAGCCGCCGA
CCCCAACGCTAAGCTCTACATCAACGACTACAACCTCGACAGCGCCAACTACGCCAAGACCAAGGGCATG
GTCAGCCACGTCAAGAAGTGGATCGCCGAGGGCATCCCCATCGACGGCATCGGCAGCCAGACTCACCTTG
GCGCTGGCGGCGGCGCTGGCGTTGCTGGCGCTCTCAACGCTCTGGCCGCTGCCGGCGTCAGCGAGGTCGC
CATCACCGAGCTGGACATTGCTGGCGCTAGCAGCAACGACTACGTCAACGTCGTCAAGGCCTGCCTCAAC
GAGCCCAAGTGCGTCGGCATCACCGTCTGGGGCGTCAGCGACAAGGACAGCTGGCGCAGCGACGACAACC
CCCTCCTCTTCGACTCCAACTACAAGCCCAAGGCCGCCTACAACGCCATCATCGACGCCCTCCGCTAA

FIGURE 3

SEQ ID No. 3

```
>Translation of synXyn85 (24aa - 327aa) 304aa
QAAASINNAFKAHGKKYFGTCADQDTLSNSQNAAIIKADFGQLTPENSMKWDATEPSQGKFNFAGADYLV
NYAKQNGKLVRGHTLVWHSQLPSWVSAITDKNTLTSVMKNHITTVMSRYKGQIYAWDVVNEIFNEDGTLR
NSVFYNVLGEDFVRIAFETARAVDPDAKLYINDYNLDSANYAKTQGMVSHVKKWLAAGIPIDGIGSQTHL
SPGGLSSSGVAGALTALASTGVSEVAITELDIAGASSNDYVNVVKACLDVPKCVGITVWGVSDKDSWRSD
DSPLLFDSNYQPKAAYNAIIDALS
```

FIGURE 4

SEQ ID No. 4

```
> synXyn85 (121bp - 1104bp, direct) 984bp
ATGAAGCTCAGCTCGTTCCTCTACACCGCCAGCCTCGTCGCCGCTATCCCTACCGCTATCGAGCCCCGAC
AGGCCGCTGCCAGCATCAACAACGCCTTCAAGGCCCACGGCAAGAAGTACTTCGGCACTTGCGCCGACCA
GGACACCCTCAGCAACAGCCAGAACGCCGCCATCATCAAGGCCGACTTCGGCCAGCTCACCCCCGAGAAC
AGCATGAAGTGGGACGCCACCGAGCCCAGCCAGGGCAAGTTCAACTTCGCTGGCGCCGACTACCTCGTCA
ACTACGCTAAGCAGAACGGCAAGCTCGTCCGCGGCCACACCCTCGTCTGGCACAGCCAGCTCCCGTCCTG
GGTCAGCGCCATCACCGACAAGAACACCCTCACCAGCGTCATGAAGAACCACATCACCACCGTCATGAGC
CGCTACAAGGGCCAGATCTACGCCTGGGACGTCGTCAACGAGATCTTCAACGAGGACGGCACCCTCCGCA
ACTCCGTCTTTTACAACGTCCTCGGCGAGGACTTCGTCCGCATTGCCTTCGAGACTGCCCGAGCCGTCGA
CCCCGACGCCAAGCTCTACATCAACGACTACAACCTCGACAGCGCCAACTACGCCAAGACCCAGGGCATG
GTCAGCCACGTCAAGAAGTGGCTCGCTGCCGGCATCCCCATCGACGGCATCGGCAGCCAGACCCACCTCA
GCCCTGGCGGCCTCAGCAGCAGCGGCGTCGCTGGCGCTCTCACCGCCCTCGCCTCTACCGGCGTCAGCGA
GGTCGCCATTACCGAGCTGGACATTGCTGGCGCTAGCAGCAACGACTACGTCAACGTCGTCAAGGCCTGC
CTCGACGTCCCCAAGTGCGTCGGCATCACCGTCTGGGGCGTCAGCGACAAGGACAGCTGGCGCAGCGACG
ACAGCCCCCTCCTCTTCGACTCCAACTACCAGCCCAAGGCCGCCTACAACGCCATCATCGACGCCCTCAG
CTAA
```

FIGURE 5

SEQ ID No. 5

>Translation of synXyn89 (24aa - 327aa) 304aa
QAAASINNAFKAHGKKYFGTCADQGTLSNSKNAAIIKADFGQLTPENSMKWDATEPSQGKFNFGGADYLV
NYAKQNGKLIRGHTLVWHSQLPSWVQDITDKNTLTSVMKNHITTVMSRYKGKIYAWDVVNEIFNEDGTLR
NSVFYNVLGEDFVRIAFETARAADPDAKLYINDYNLDSANYAKTKGMVSHVKKWIAAGIPIDGIGSQTHL
GAGGLSGSGVAGALNALASTGVSEVAITELDIAGASSNDYVNVVKACLNVPKCVGITVWGVSDKDSWRSD
DSPLLFDSNYQPKAAYNAIIDALS

FIGURE 6

SEQ ID No. 6

> synXyn89 (121bp - 1104bp, direct) 984bp
ATGAAGCTCAGCTCGTTCCTCTACACCGCCAGCCTCGTCGCCGCTATCCCTACCGCCATCGAGCCCCGAC
AGGCCGCTGCCAGCATCAACAACGCCTTCAAGGCCCACGGCAAGAAGTACTTCGGCACTTGCGCCGACCA
GGGCACGCTCAGCAACAGCAAGAACGCCGCCATCATCAAGGCCGACTTCGGCCAGCTCACCCCCGAGAAC
AGCATGAAGTGGGACGCCACCGAGCCCAGCCAGGGCAAGTTCAACTTTGGCGGCGCTGACTACCTCGTCA
ACTACGCTAAGCAGAACGGCAAGCTCATCCGCGGCCACACCCTCGTCTGGCACAGCCAGCTCCCGTCCTG
GGTCCAGGACATCACCGACAAGAACACCCTCACCAGCGTCATGAAGAACCACATCACCACCGTCATGAGC
CGCTACAAGGGCAAGATCTACGCCTGGGACGTCGTCAACGAGATCTTCAACGAGGACGGCACCCTCCGCA
ACTCCGTCTTTTACAACGTCCTCGGCGAGGACTTCGTCCGCATTGCCTTCGAGACTGCCCGAGCCGCCGA
CCCCGACGCCAAGCTCTACATCAACGACTACAACCTCGACAGCGCCAACTACGCCAAGACCAAGGGCATG
GTCAGCCACGTCAAGAAGTGGATCGCTGCCGGCATCCCCATCGACGGCATCGGCAGCCAGACCCACCTCG
GCGCTGGCGGCCTTTCTGGCTCTGGCGTGGCTGGCGCCCTCAACGCCCTCGCCAGCACCGGCGTCAGCGA
GGTCGCCATCACCGAGCTGGACATTGCTGGCGCTAGCAGCAACGACTACGTCAACGTCGTCAAGGCCTGC
CTCAACGTCCCCAAGTGCGTCGGCATCACCGTCTGGGGCGTCAGCGACAAGGACAGCTGGCGCAGCGACG
ACAGCCCCCTCCTCTTCGACTCCAACTACCAGCCCAAGGCCGCCTACAACGCCATCATCGACGCCCTCAG
CTAA

FIGURE 7

SEQ ID No. 7

>Translation of synXyn72 (24aa - 324aa) 301aa
QAAASINNAFKAKGKKYFGTCADQGTLSDSTNSAIIKADFGQLTPENSMKWDATEPSQGKFSFGGADYLV
NYATSNGKLIRGHTLVWHSQLPSWVQGITDKNTLTSVLKNHITTVMNRYKGKIYAWDVVNEIFNEDGTLR
NSVFYNVLGEDFVRIAFETARAVDPQAKLYINDYNLDSANYAKTKGMANHVKKWIAQGIPIDGIGSQTHL
GAGGSSGVKGALNTLASSGVSEVAITELDIAGASSNDYVNVVKACLNVSKCVGITVWGVSDKDSWRSDDS
PLLFDSNYQPKAAYNAIINAL

FIGURE 8

SEQ ID No. 8

>synXyn72 (121bp - 1095bp, direct) 975bp
ATGAAGCTCAGCTCGTTCCTCTACACCGCCAGCCTCGTCGCCGCCATCCCTACCGCCATCGAGCCCCGAC
AGGCCGCTGCCAGCATCAACAACGCCTTCAAGGCCAAGGGCAAGAAGTACTTCGGCACTTGCGCCGACCA
GGGCACGCTCAGCGACAGCACCAACAGCGCCATCATCAAGGCCGACTTCGGCCAGCTCACCCCCGAGAAC
AGCATGAAGTGGGACGCCACCGAGCCCAGCCAGGGCAAGTTCAGCTTTGGCGGCGCTGACTACCTCGTCA
ACTACGCCACCAGCAACGGCAAGCTCATCCGCGGCCACACCCTCGTCTGGCACAGCCAGCTCCCGTCCTG
GGTCCAGGGCATCACCGACAAGAACACCCTCACCAGCGTCCTCAAGAACCACATCACCACCGTCATGAAC
CGCTACAAGGGCAAGATCTACGCCTGGGACGTCGTCAACGAGATCTTCAACGAGGATGGCACCCTCCGCA
ACAGCGTCTTTTACAACGTCCTGGGCGAGGACTTCGTCCGCATTGCCTTCGAGACTGCCCGAGCCGTCGA
CCCCCAGGCCAAGCTCTACATCAACGACTACAACCTCGACAGCGCCAACTACGCCAAGACCAAGGGCATG
GCCAACCACGTCAAGAAGTGGATCGCCCAGGGCATCCCCATCGACGGCATCGGCAGCCAGACCCACCTCG
GCGCTGGCGGCTCTAGCGGCGTCAAGGGCGCTCTCAACACCCTCGCCAGCTCCGGCGTCAGCGAGGTCGC
CATCACCGAGCTGGACATTGCTGGCGCCTCGAGCAACGACTACGTCAACGTCGTCAAGGCCTGCCTCAAC
GTCAGCAAGTGCGTCGGCATCACCGTCTGGGGCGTCTCCGACAAGGACAGCTGGCGCAGCGACGACAGCC
CCCTCCTCTTCGACTCCAACTACCAGCCCAAGGCCGCCTACAACGCCATCATTAACGCCCTCTAA

FIGURE 9

SEQ ID No. 9

>Translation of synXyn80 (24aa - 325aa) 302aa
QAAASIDAKFKAHGKKYFGNIADQYTLTKNPKTAAIIKADFGQLTPENSMKWDATEPSRGKFNFGGSDYL
VNFAKQNNKLIRGHTLVWHSQLPSWVQNINDKNTLTQVMKNHITTVMSRYKGKIYAWDVVNEIFNEDGTL
RNSVFYNVLGEDFVRIAFETARAADPNAKLYINDYNLDSANYAKTKGMVSHVKKWIAEGIPIDGIGSQTH
LGAGGGAGVSGALNALATAGTKEVAITELDIAGASSTDYVNVVKACLNQPKCVGITVWGVSDKDSWRSDD
TPLLFDSNYNPKPAYNAITDAL

FIGURE 10

SEQ ID No. 10

> synXyn80 (121bp - 1098bp, direct) 978bp
ATGAAGCTCAGCTCGTTCCTCTACACCGCCAGCCTCGTCGCCGCTATCCCTACCGCCATCGAGCCCCGAC
AGGCCGCTGCCAGCATCGACGCCAAGTTCAAGGCCCACGGCAAGAAGTACTTCGGCAACATTGCCGACCA
GTACACGCTCACCAAGAACCCCAAGACCGCCGCCATCATCAAGGCCGACTTCGGCCAGCTCACCCCCGAG
AACAGCATGAAGTGGGACGCCACCGAGCCCAGCCGAGGCAAGTTCAACTTCGGCGGCAGCGACTACCTCG
TCAACTTCGCCAAGCAGAACAACAAGCTCATCCGCGGCCACACCCTCGTCTGGCACAGCCAGCTCCCGTC
CTGGGTCCAGAACATCAACGACAAGAACACCCTCACCCAGGTCATGAAGAACCACATCACCACCGTCATG
AGCCGCTACAAGGGCAAGATCTACGCCTGGGACGTCGTCAACGAGATCTTCAACGAGGACGGCACCCTCC
GCAACAGCGTCTTTTACAACGTCCTGGGCGAGGACTTCGTCCGCATTGCCTTCGAGACTGCCCGAGCCGC
CGACCCCAACGCCAAGCTCTACATCAACGACTACAACCTCGACAGCGCCAACTACGCCAAGACCAAGGGC
ATGGTCAGCCACGTCAAGAAGTGGATCGCCGAGGGCATCCCCATCGACGGCATCGGCTCTCAGACTCACC
TCGGCGCTGGCGGCGGCGCTGGCGTCTCTGGCGCTCTCAACGCCCTCGCCACCGCCGGCACCAAGGAGGT
CGCCATCACCGAGCTGGACATTGCTGGCGCTAGCAGCACCGACTACGTCAACGTCGTCAAGGCCTGCCTC
AACCAGCCCAAGTGCGTCGGCATCACCGTCTGGGGCGTCAGCGACAAGGACAGCTGGCGCAGCGACGACA
CCCCCCTGCTGTTCGACAGCAACTACAACCCCAAGCCCGCCTACAACGCCATCACGGACGCCCTCTAA

FIGURE 11

SEQ ID No. 11

```
>Translation of synXyn93
QAAASIDNAFKAHGKKYFGTCADQDTLTNPKNVAIIKADFGQLTPENSMKWDATEPSQGKFNFGGADYLV
NFAKQNGKLIRGHTLVWHGQLPSWVQNINDKNTLTKVMKNHITTVMSRYKGKIYAWDVVNEIFNEDGTLR
NSVFYNVLGEDFVRIAFETARAADPNAKLYINDYNLDSANYAKTKGMVSHVKKWIAEGIPIDGIGSQTHL
GAGGGAGVAGALNALAAAGVSEVAITELDIAGASSNDYVNVVKACLNEPKCVGITVWGVSDKDSWRSDDN
PLLFDSNYKPKAAYNAIIDALR*
```

FIGURE 12

SEQ ID No. 12

```
>13AA22XC_synXyn93(121bp - 1098bp, direct) 978bp
ATGAAGCTCAGCTCGTTCCTCTACACCGCCAGCCTCGTCGCTGCCATCCCTACCGCTATCGAGCCCCGAC
AGGCTGCTGCCAGCATCGACAACGCCTTCAAGGCCCACGGCAAGAAGTACTTCGGCACTTGCGCCGACCA
GGACACGCTCACCAACCCCAAGAACGTCGCCATCATCAAGGCCGACTTCGGCCAGCTCACCCCCGAGAAC
AGCATGAAGTGGGACGCCACCGAGCCCAGCCAGGGCAAGTTCAACTTTGGCGGCGCTGACTACCTCGTCA
ACTTCGCCAAGCAGAACGGCAAGCTCATCCGCGGCCACACCCTCGTCTGGCACGGCCAGCTCCCTAGCTG
GGTCCAGAACATCAACGACAAGAACACCCTGACCAAGGTCATGAAGAACCACATCACCACCGTCATGAGC
CGCTACAAGGGCAAGATCTACGCCTGGGACGTCGTCAACGAGATCTTCAACGAGGACGGCACCCTCCGCA
ACAGCGTCTTTTACAACGTCCTGGGCGAGGACTTCGTCCGCATTGCCTTCGAGACTGCCCGAGCCGCCGA
CCCCAACGCTAAGCTCTACATCAACGACTACAACCTCGACAGCGCCAACTACGCCAAGACCAAGGGCATG
GTCAGCCACGTCAAGAAGTGGATCGCCGAGGGCATCCCCATCGACGGCATCGGCAGCCAGACTCACCTTG
GCGCTGGCGGCGGCGCTGGCGTTGCTGGCGCTCTCAACGCTCTGGCCGCTGCCGGCGTCAGCGAGGTCGC
CATCACCGAGCTGGACATTGCTGGCGCTAGCAGCAACGACTACGTCAACGTCGTCAAGGCCTGCCTCAAC
GAGCCCAAGTGCGTCGGCATCACCGTCTGGGGCGTCAGCGACAAGGACAGCTGGCGCAGCGACGACAACC
CCCTCCTCTTCGACTCCAACTACAAGCCCAAGGCCGCCTACAACGCCATCATCGACGCCCTCCGCTAA
```

POLYPEPTIDE HAVING XYLANASE ACTIVITY

CROSS-REFERENCE TO RELATED APPLICATIONS

This application is a National Stage Entry of International Patent Application No. PCT/EP2015/051979, filed Jan. 30, 2015, which claims priority to United Kingdom Patent Application No. 1401699.2, filed Jan. 31, 2014, the disclosures of each of which are incorporated by reference herein.

FIELD OF THE INVENTION

The present invention relates to novel synthetic xylanases and the use of said xylanases in applications, including in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry, and methods using these xylanases, as well as compositions (such as feed additive compositions) comprising said xylanases.

BACKGROUND OF THE INVENTION

For many years, endo-β-1,4-xylanases (EC 3.2.1.8) (referred to herein as xylanases) have been used for the modification of complex carbohydrates derived from plant cell wall material. It is well known in the art that the functionality of different xylanases (derived from different microorganisms or plants) differs enormously. Xylanase is the name given to a class of enzymes which degrade the linear polysaccharide beta-1,4-xylan into xylooligosaccharides or xylose, thus breaking down hemicellulose, one of the major components of plant cell walls.

Based on structural and genetic information, xylanases have been classified into different Glycoside Hydrolase (GH) families (Henrissat, (1991) *Biochem. J.* 280, 309-316).

Initially all known and characterized xylanases belonged to the families GH10 or GH11. Further work then identified numerous other types of xylanases belonging to the families GH5, GH7, GH8 and GH43 (Collins et al (2005) *FEMS Microbiol Rev.*, 29 (1), 3-23).

Until now the GH11 family differs from all other GH's, being the only family solely consisting of xylan specific xylanases. The structure of the GH11 xylanases can be described as a β-Jelly roll structure or an all β-strand sandwich fold structure (Himmel et al 1997 *Appl. Biochem. Biotechnol.* 63-65, 315-325). GH11 enzymes have a catalytic domain of around 20 kDa.

GH10 xylanases have a catalytic domain with molecular weights in the range of 32-39 kDa. The structure of the catalytic domain of GH10 xylanases consists of an eightfold β/α barrel (Harris et al 1996—Acta. Crystallog. Sec. D 52, 393-401).

Three-dimensional structures are available for a large number of Family GH10 enzymes, the first solved being those of the *Streptomyces lividans* xylanase A (Derewenda et al J Biol Chem 1994 Aug. 19; 269(33) 20811-4), the *C. fimi* endo-glycanase Cex (White et al Biochemistry 1994 Oct. 25; 33(42) 12546-52), and the *Cellvibrio japonicus* Xyn10A (previously *Pseudomonas fluorescens* subsp. xylanase A) (Harris et al Structure 1994 Nov. 15; 2(11) 1107-16.). As members of Clan GHA they have a classical $(\alpha/\beta)_8$ TIM barrel fold with the two key active site glutamic acids located at the C-terminal ends of beta-strands 4 (acid/base) and 7 (nucleophile) (Henrissat et al Proc Natl Acad Sci USA 1995 Jul. 18; 92(15) 7090-4).

Comprehensive studies characterising the functionality of xylanases have been done on well characterised and pure substrates (Kormelink et al., 1992 Characterisation and mode of action of xylanases and some accessory enzymes. Ph.D. Thesis, Agricultural University Wageningen, Holland (175 pp., English and Dutch summaries)). These studies show that different xylanases have different specific requirements with respect to substitution of the xylose backbone of the arabinoxylan (AX). Some xylanases require three unsubstituted xylose residues to hydrolyse the xylose backbone; others require only one or two. The reasons for these differences in specificity are thought to be due to the three dimensional structure within the catalytic domains, which in turn is dependent on the primary structure of the xylanase, i.e. the amino acid sequence. However, the translation of these differences in the amino acid sequences into differences in the functionality of the xylanases, has not been documented when the xylanase acts in a complex environment, such as a plant material, e.g. in a feedstuff.

The xylanase substrates in plant material, e.g. in wheat, have traditionally been divided into two fractions: The water un-extractable AX (WU-AX) and the water extractable AX (WE-AX). There have been numerous explanations as to why there are two different fractions of AX. The older literature (D'Appolonia and MacArthur—(1976, Cereal Chem. 53. 711-718) and Montgomery and Smith (1955, J. Am. Chem. Soc. 77. 3325-332) describes quite high differences in the substitution degree between WE-AX and WU-AX. The highest degree of substitution was found in WE-AX. This was used to explain why some of the AX was extractable. The high degree of substitution made the polymer soluble, compared to a lower substitution degree, which would cause hydrogen bonding between polymers and consequently precipitation.

The difference between the functionality of different xylanases has been thought to be due to differences in xylanase specificity and thereby their preference for the WU-AX or the WE-AX substrates.

Xylanase enzymes have been reported from nearly 100 different organisms, including plants, fungi and bacteria. The xylanase enzymes are classified into several of the more than 40 families of glycosyl hydrolase enzymes. The glycosyl hydrolase enzymes, which include xylanases, mannanases, amylases, β-glucanases, cellulases, and other carbohydrases, are classified based on such properties as the sequence of amino acids, their three dimensional structure and the geometry of their catalytic site (Gilkes, et al., 1991, Microbiol. Reviews 55: 303-315).

BRIEF DESCRIPTION OF THE DRAWINGS

FIG. 1 shows the mature polypeptide of a synthetic xylanase designated herein as SynXyn92 (SEQ ID No. 1).

FIG. 2 shows the polynucleotide sequence of a synthetic xylanase designated herein as SynXyn92 (SEQ ID No. 2).

FIG. 3 shows the mature polypeptide of a synthetic xylanase designated herein as SynXyn85 (SEQ ID No. 3).

FIG. 4 shows the polynucleotide sequence of a synthetic xylanase designated herein as SynXyn85 (SEQ ID No. 4).

FIG. 5 shows the mature polypeptide of a synthetic xylanase designated herein as SynXyn89 (SEQ ID No. 5).

FIG. 6 shows the polynucleotide sequence of a synthetic xylanase designated herein as SynXyn89 (SEQ ID No. 6).

FIG. 7 shows the mature polypeptide of a synthetic xylanase designated herein as SynXyn72 (SEQ ID No. 7).

FIG. 8 shows the polynucleotide sequence of a synthetic xylanase designated herein as SynXyn72 (SEQ ID No. 8).

FIG. 9 shows the mature polypeptide of a synthetic xylanase designated herein as SynXyn80 (SEQ ID No. 9).

FIG. 10 shows the polynucleotide sequence of a synthetic xylanase designated herein as SynXyn80 (SEQ ID No. 9).

FIG. 11 shows the mature polypeptide of a synthetic xylanase designated herein as SynXyn93 (SEQ ID No. 11).

FIG. 12 shows the polynucleotide sequence of a synthetic xylanase designated herein as SynXyn93 (SEQ ID No. 12).

SUMMARY OF THE INVENTION

Figure 13:
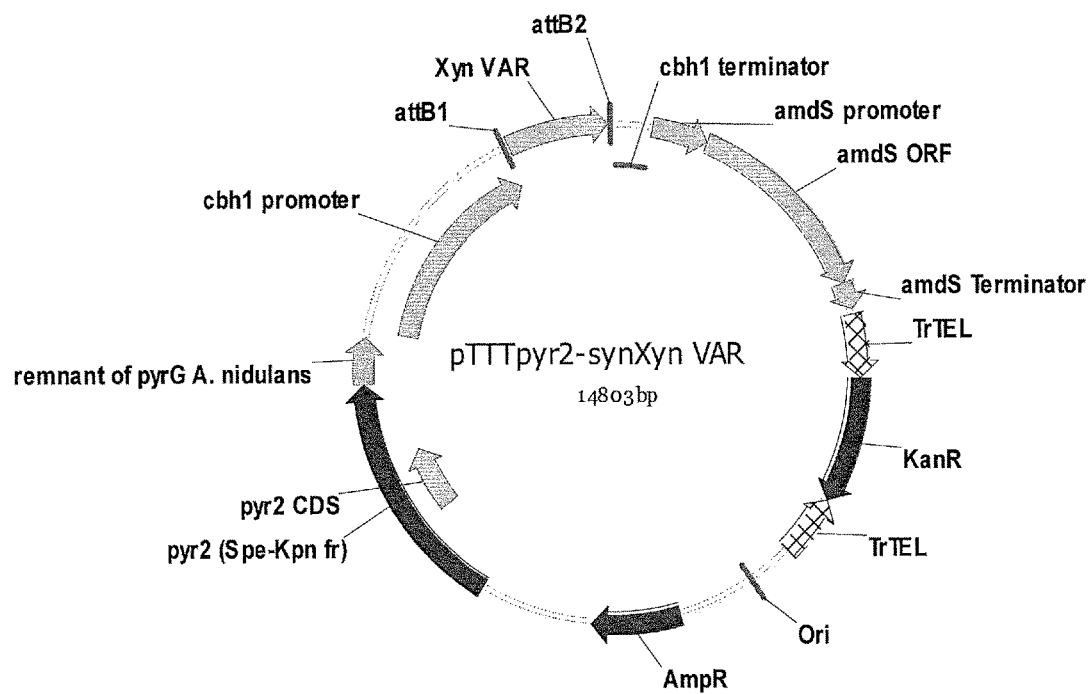
FIG. 13 shows a schematic map of the expression vector for the synthetic xylanases (pTTTpyr2-synXyn_VAR).
Figure 14:
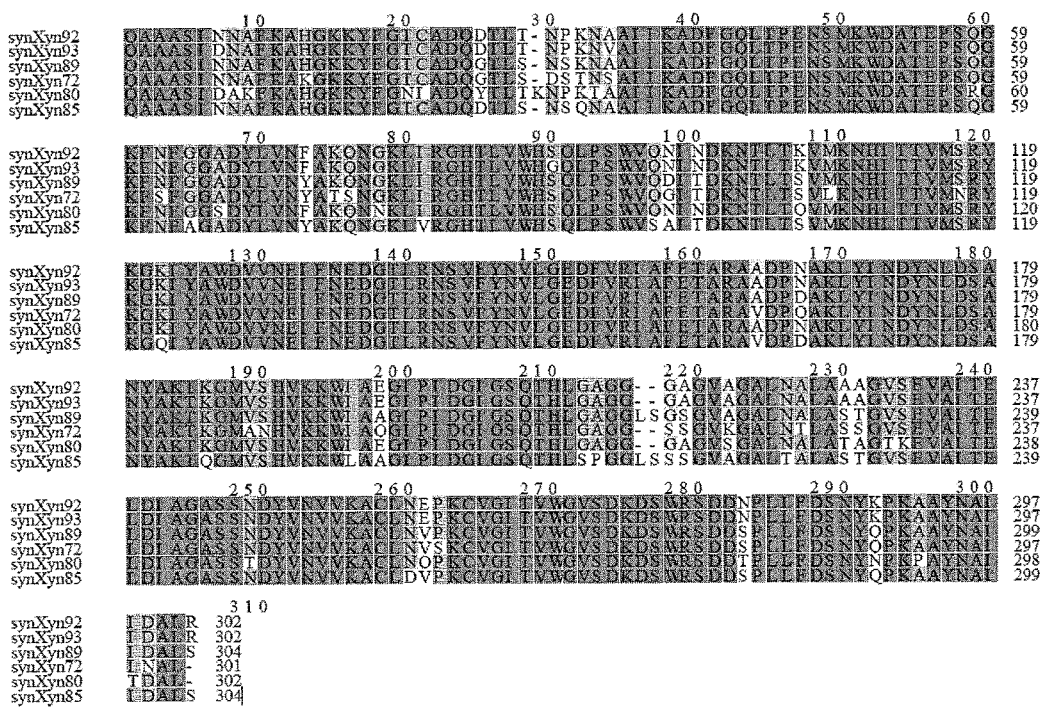
FIG. 14 shows an alignment of the mature polypeptide sequences of the synthetic xylanases—CLUSTAL Omega multiple sequence alignment was used with default parameter settings (Matrix: Gonnet; Gap Opening Penalty: 10; Gap Extension: 0.2).
Figure 15:
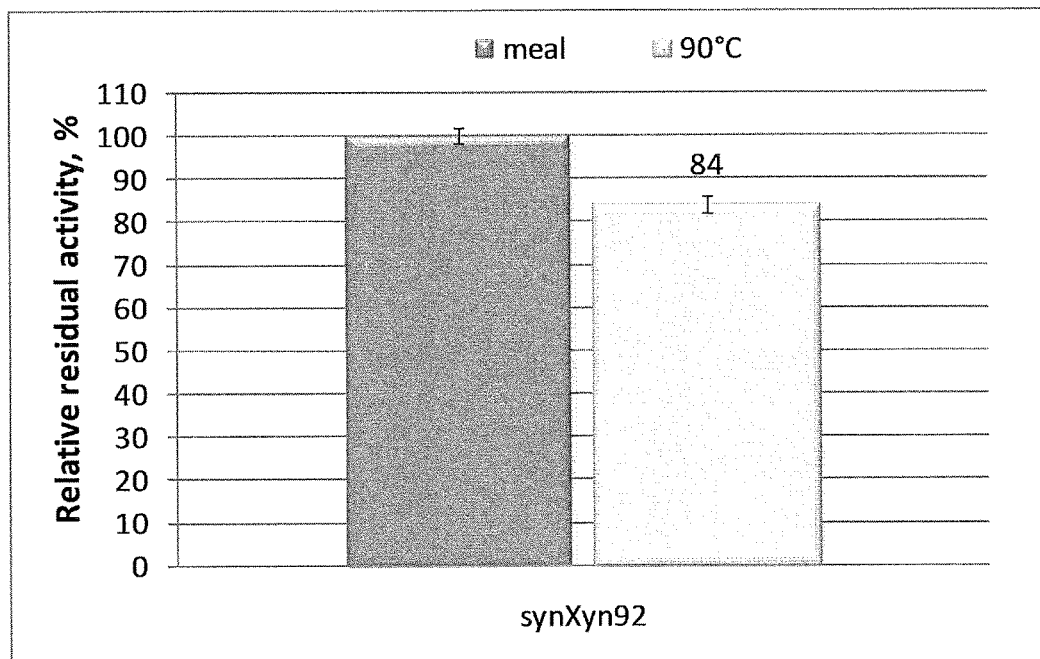
FIG. 15 shows the results of a pelleting test for processing stability of the synthetic xylanase SynXyn92—at processing temperatures of 90° C.

A seminal finding of the present invention is that synthetic xylanases can be designed which in addition to having the ability to breakdown (solubilise) insoluble arabinoxylans (AXinsol), they have other properties that render them especially useful in applications, such as in feedstuffs, in brewing or malting, in the treatment of arabinoxylan containing raw materials like grain-based materials, e.g. in the production of biofuel or other fermentation products, including biochemicals (e.g. bio-based isoprene), and/or in the wheat gluten-starch separation industry. For instance the synthetic xylanases taught herein are surprisingly thermostable, have surprisingly high recovery, e.g. residual activity after heat treatment (e.g. during the pelleting process) and are pepsin resistant.

During the pelleting process the enzyme (e.g. a feed comprising the enzyme) is conditioned for 30 seconds at 90° C.

During the pelleting process an enzyme may be formulated on a substrate, e.g. wheat, and may be formulated into a premix, e.g. a corn/soy feed mix (such as 61.1% Corn, 31.52% Hipro Soya 48, 4.00% Soya Oil, 0.40% Sodium Bicarbonate, 0.25% Vitamins/Minerals Leghennen, 0.20% DL-methionine, 1.46% Dicalcium Phosphate, 1.16% Limestone).

The xylanase can be included at a level which ensures a final target dosage is achieved, e.g. 20 000 XU/kg feed. The premix may be prepared by mixing the enzyme(s) formulated on the substrate, e.g. wheat, into a feed mix, e.g. 10 kg corn/soy feed mix and mixed, for a specified time, e.g. 10 min.

The premix may be added to feed, e.g. 110 kg feed, and mixed for a specified time, e.g. 10 min, before conditioning. The feed comprising the enzyme is typically conditioned for 30 seconds at 90° C. before pelleting.

The feed comprising the enzyme may be treated with dry steam to reach a target temperature of 90° C. after 30 seconds.

The term "conditioned" or "conditioning" as used herein means mixing the feed/enzyme mixture and treating same with dry steam to reach a target temperature of 90° C. after 30 seconds.

Following the conditioning the feed/enzyme mixture may be formed into pellets. The formation of the pellets may be done by any conventional means known to one skilled in the art. The pellets may be formed by the pelleting process described herein.

For the first time, the present inventors have been able to express entirely synthetic polypeptides having xylanase activity and enhanced properties.

The synthetic xylanases taught herein are GH10 xylanases.

In particular the synthetic xylanases of the present invention efficiently breakdown (solubilise) AXinsol from a wide range of substrates, including corn, wheat, DDGS, etc., in particular corn and corn based substrates, in particular both wheat (including wheat-based) products and corn (including corn-based products). This contrasts with prior-known enzymes, which are often inferior at solubilising AXinsol in corn or corn-based substrates or which are not efficient in both wheat- and corn-based substrates.

In addition, the synthetic xylanases of the present invention may be particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol), a (fast) reduction in viscosity is obtained or the solubilized polymers (obtained from dissolving AXinsol) cannot contribute to increasing viscosity. This latter effect is essential in some of the claimed applications.

Without wishing to be bound by theory, the synthetic enzyme of the present invention mainly releases polymers, which do not contribute to viscosity, because the released polymers are short.

Typically, conventional xylanases may breakdown AXinsol, but will often lead to an increase in viscosity of the mixture. This increased viscosity is disadvantageous in many applications.

Without wishing to be bound by theory, although some conventional xylanases breakdown AXinsol, they lead to an increase in soluble degradation products of high molecular weight, which leads to an increase in viscosity in the mixture.

Furthermore or alternatively and again without wishing to be bound by theory, conventional xylanase enzymes may breakdown AXinsol, but because they do not degrade the solubilised products of high molecular weight fast enough the viscosity in the mixture is not ideal. In contrast, with the methods and uses of the present invention, the synthetic xylanases breakdown AXinsol without increasing viscosity and/or whilst reducing viscosity quickly compared with conventional enzymes. Without wishing to be being bound by theory, it is believed that high molecular weight products are not formed by the enzymes of the present invention.

The enzymes of the present invention and as described herein have been found to not only breakdown (solubilise) insoluble arabinoxylans (AXinsol) from a wide range of substrates, including corn, wheat, DDGS, etc., in particular corn and corn-based substrates, in particular both wheat (including wheat-based) products and corn (including corn-based products), but also efficiently ensuring that viscosity is not raised and/or reducing viscosity. Without wishing to be being bound by theory, it is believed that high molecular weight products are not formed by the enzymes of the present invention.

Thus the present invention relates to enzymes capable of solubilising pentosans, in particular xylan-containing materials, such as arabinoxylans, in particular insoluble arabinoxylans. In particular the enzyme is particularly good at solubilising pentosans in particular xylan-containing materials, such as arabinoxylans, in particular insoluble arabinoxylans, in a broad spectrum of substrates, including corn based substrates.

Many of the xylanases commercialized for use in feedstuffs for solubilizing pentosans are GH11 enzymes. It had been considered by those skilled in the art that GH10 xylanases were not as strong at solubilizing pentosans, particularly AXinsol, compared with GH11 xylanases. Surprisingly it has been found that the synthetic xylanases disclosed herein which are GH10 xylanases are particularly good at degrading AXinsol in a broad spectrum of substrates, including corn based substrates. Surprisingly, the present inventors have found that the synthetic GH10 xylanases of the present invention outperform commercial GH11 xylanases in their ability to solubilize pentosans. In addition the synthetic GH10 xylanases are thermostable.

The fact that the present enzymes efficiently degrade AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-based diet, such as corn-soy diet for example.

It was completely unexpected for a GH10 xylanase to be so good at degrading AXinsol in cereals, particularly in corn or corn-based substrates.

The enzymes of the present invention may be able to efficiently (and quickly) degrade the polymers and oligomers that are produced from degradation of AXinsol or that are present in grain-based material. This leads to an unexpected advantage for the synthetic xylanases taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g. bio-based isoprene); or in the wheat gluten-starch separation industry for the production of starch for example.

Notably it has been found that the degradation product on average is shorter for the synthetic enzymes tested herein compared with GH11 enzymes. This means that the degradation products do not contribute to or cause an increase in viscosity.

Based on these findings, the synthetic xylanases according to the present invention can be used to degrade a xylan-containing material, particularly arabinoxylans, particularly AXinsol.

In addition or alternatively, the xylanases according to the present invention can be used to degrade soluble polymers (e.g. oligomers) that are produced from degradation of AXinsol or that are (naturally) present in grain-based materials. Surprisingly it has been found that the variant xylanases according the present invention can be used to both degrade a xylan-containing material, particularly arabinoxylans, particularly AXinsol, and to degrade soluble polymers (e.g. oligomers) that are produced from degradation of AXinsol.

Such enzymes finds useful application in many industries, including feedstuffs, malting and brewing, in the treatment of arabinoxylan containing raw materials like grain-based materials, in the wheat gluten-starch separation industry, in the production of starch derived syrups, in biofuel production, and the like.

Statements of the Invention

In a first aspect the present invention provides an isolated polypeptide having xylanase activity, selected from the group consisting of:
  (a) a polypeptide comprising an amino acid sequence having at least 87% identity (suitably at least 89%, suitably at least 90%, suitably at least 92%, suitably at least 94%, suitably at least 98%, suitably at least 100% identity) with SEQ ID NO: 1;
  (b) a polypeptide encoded by a polynucleotide having at least 87% identity (suitably at least 89%, suitably at least 90%, suitably at least 92%, suitably at least 94%, suitably at least 98%, suitably at least 100% identity) with SEQ ID NO:2; or
  (c) a fragment of a polypeptide of a) or b) which fragment has xylanase activity.

In a further aspect the present invention provides an isolated polynucleotide (e.g. cDNA) comprising a nucleotide sequence which encodes the polypeptide of the present invention.

In a yet further aspect, there is provided an isolated polynucleotide (e.g. cDNA) comprising a polynucleotide having at least 87% identity (suitably at least 89%, suitably at least 90%, suitably at least 92%, suitably at least 94%, suitably at least 98%, suitably at least 100% identity) with SEQ ID No: 2; or an isolated polynucleotide which differs from SEQ ID No. 2 due to the degeneracy of the genetic code.

The present invention yet further provides an isolated polynucleotide (e.g. cDNA) selected from the group consisting of: SEQ ID No. 2, SEQ ID No. 4, SEQ ID No. 6, SEQ ID No. 8, SEQ ID No. 10 and SEQ ID No. 12, or an isolated polynucleotide which differs from SEQ ID No. 2, SEQ ID No. 4, SEQ ID No. 6, SEQ ID No. 8, SEQ ID No. 10 and SEQ ID No. 12 due to the degeneracy of the genetic code.

In one aspect the present invention provides a nucleic acid construct comprising the polynucleotide of the present invention operably linked to one or more control sequences that direct the production of the polypeptide in an expression host.

In another aspect, the present invention provides a recombinant expression vector comprising the nucleic acid construct of the present invention.

There is further provided, a recombinant host cell comprising a polynucleotide according the present invention, a nucleic acid construct of the present invention nucleic acid construct of the present invention or a vector according to the present invention.

The present invention further provides a method for producing the polypeptide of the present invention comprising (a) cultivating a host cell comprising a nucleic acid construct according to the present invention under conditions conducive for production of the polypeptide; and (b) recovering the polypeptide.

In a further aspect of the present invention there is provided a fermentate produced by the method of the present invention.

A yet further aspect of the present invention is the provision of a xylanase produced by the method of the present invention.

The present invention yet further provides an enzyme composition comprising a) a synthetic xylanase according to the present invention, b) the fermentate according to the present invention, or c) a combination thereof.

The present invention further provides a feed additive composition comprising a) a synthetic xylanase enzyme according to the present invention, b) the fermentate according to the present invention, or c) a combination thereof.

In a further aspect of the present invention there is provided a premix comprising a) a synthetic xylanase enzyme according to the present invention, b) the fermentate according to the present invention, c) the enzyme composition according to the present invention, d) a feed additive composition according to the present invention or e) a combination thereof; and at least one vitamin and/or at least one mineral.

The present invention yet further provides a feed (or feedstuff) comprising a) a synthetic xylanase enzyme according to the present invention, b) the fermentate according to the present invention, c) the enzyme composition according to the present invention, d) a feed additive composition according to the present invention, e) a premix according to the present invention or f) a combination thereof.

In a further aspect there is provided a method of preparing a feedstuff comprising admixing a feed component with a) a synthetic xylanase according to the present invention, b) the fermentate according to the present invention, c) the enzyme composition according to the present invention, d) a feed additive composition according to the present invention, e) a premix according to the present invention or f) a combination thereof.

The present invention yet further provides a method for degrading arabinoxylan-containing material in a xylan-containing material, comprising admixing said xylan-containing material with a) a synthetic xylanase enzyme according to the present invention, b) the fermentate according to the present invention, c) the enzyme composition according to the present invention, d) a feed additive composition according to the present invention, e) a premix according to the present invention or f) a combination thereof.

In another aspect, there is provided use of a) a synthetic xylanase enzyme according to the present invention, b) the fermentate according to the present invention, c) the enzyme composition according to the present invention, d) a feed additive composition according to the present invention, e) a premix according to the present invention or f) a combination thereof for solubilizing arabinoxylan in a xylan-containing material.

DETAILED DISCLOSURE OF THE PREFERRED EMBODIMENTS OF THE INVENTION

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be had by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "the feed" includes reference to one or more feeds and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

Increasing prices of raw material traditionally used as an energy source in animal feed, as a feedstock in biofuel production, as an ingredient in brewing or malting, or as a feedstock in wheat gluten-starch separation processes for instance have resulted in inclusion of low-cost fibrous materials in the starting substrates for these industries, particularly the use of low-cost fibrous by-products in animal feed.

Fibre addition may cause several disadvantageous effects. For example in animal feed fibre addition may cause anti-nutritional effects. In feedstuffs, hemicellulose and cellulose (including insoluble arabinoxylan) form physical barriers encapsulating (or entrapping) nutrients like starch and protein and thereby retaining access to these nutrients for the animal.

Hemicellulose and cellulose (including insoluble arabinoxylans (AXinsol)) by themselves are also potential energy sources, as they consist of C5- and C6-saccharides. Mono C6-saccharides can be used as energy source by the animal, while oligo C5-saccharides can be transformed into short chain fatty acids by the micro flora present in the animal gut (van den Broek et al., 2008 Molecular Nutrition & Food Research, 52, 146-63), which short chain fatty acids can be taken up and digested by the animal's gut.

Release of nutrients from feedstuffs as a consequence of physical barrier degradation is dependent on the ability of the xylanase to degrade insoluble fibre components (e.g. insoluble arabanoxylans (AXinsol)).

In a first aspect the present invention provides an isolated polypeptide having xylanase activity, selected from the group consisting of:
  (a) a polypeptide comprising an amino acid sequence having at least 87% identity with SEQ ID NO: 1;
  (b) a polypeptide encoded by a polynucleotide having at least 87% identity with SEQ ID NO:2; or
  (c) a fragment of a polypeptide of a) or b) which fragment has xylanase activity.

In another aspect the present invention provides an isolated polypeptide having xylanase activity, selected from the group consisting of:
  (a) a polypeptide comprising an amino acid sequence having at least 89% identity with SEQ ID NO: 1;
  (b) a polypeptide encoded by a polynucleotide having at least 89% identity with SEQ ID NO:2; or
  (c) a fragment of a polypeptide of a) or b) which fragment has xylanase activity.

In one embodiment the present invention provides an isolated polypeptide having xylanase activity, selected from the group consisting of:
  (a) a polypeptide comprising an amino acid sequence having at least 90% identity with SEQ ID NO: 1;
  (b) a polypeptide encoded by a polynucleotide having at least 90% identity with SEQ ID NO:2; or
  (c) a fragment of a polypeptide of a) or b) which fragment has xylanase activity.

In another embodiment the present invention provides an isolated polypeptide having xylanase activity, selected from the group consisting of:
  (a) a polypeptide comprising an amino acid sequence having at least 94% identity with SEQ ID NO: 1;
  (b) a polypeptide encoded by a polynucleotide having at least 94% identity with SEQ ID NO:2; or
  (c) a fragment of a polypeptide of a) or b) which fragment has xylanase activity.

In a yet further embodiment the present invention provides an isolated polypeptide having xylanase activity, selected from the group consisting of:
  (a) a polypeptide comprising an amino acid sequence having at least 98% identity with SEQ ID NO: 1;
  (b) a polypeptide encoded by a polynucleotide having at least 98% identity with SEQ ID NO:2; or
  (c) a fragment of a polypeptide of a) or b) which fragment has xylanase activity.

The polypeptide according to the present invention may comprise an amino acid sequence selected from the group consisting of SEQ ID No. 1, SEQ ID No: 3, SEQ ID No. 5, SEQ ID No. 7, SEQ ID No. 9 and SEQ ID No. 11.

In one embodiment the present invention provides a polypeptide having xylanase activity, comprising an amino acid sequence having at least 87% identity with one of the amino acid sequences selected from the group consisting of: SEQ ID No. 1, SEQ ID No: 3, SEQ ID No. 5, SEQ ID No. 7, SEQ ID No. 9 and SEQ ID No. 11.

In one embodiment the present invention provides a polypeptide having xylanase activity, comprising an amino acid sequence having at least 93% identity with one of the amino acid sequences selected from the group consisting of: SEQ ID No. 1, SEQ ID No: 3, SEQ ID No. 5, SEQ ID No. 7, SEQ ID No. 9 and SEQ ID No. 11.

In one embodiment the present invention provides a polypeptide having xylanase activity, comprising an amino acid sequence having at least 98% identity with one of the amino acid sequences selected from the group consisting of: SEQ ID No. 1, SEQ ID No: 3, SEQ ID No. 5, SEQ ID No. 7, SEQ ID No. 9 and SEQ ID No. 11.

In one embodiment the polypeptide having xylanase activity comprises an amino acid sequence selected from the group consisting of: SEQ ID No. 1, SEQ ID No: 3, SEQ ID No. 5, SEQ ID No. 7, SEQ ID No. 9 and SEQ ID No. 11.

In a specific embodiment the polypeptide having xylanase activity comprises an amino acid sequence shown herein as SEQ ID No. 1.

In a further embodiment the polypeptide according to the present invention may consist of an amino acid sequence selected from the group consisting of SEQ ID No. 1, SEQ ID No: 3, SEQ ID No. 5, SEQ ID No. 7, SEQ ID No. 9 and SEQ ID No. 11.

In one embodiment the polypeptide may be encoded by a polynucleotide having at least 87% identity with SEQ ID No. 2, SEQ ID No. 4, SEQ ID No. 6, SEQ ID No. 8, SEQ ID No. 10 and SEQ ID No. 12; or at least 87% identity with a polynucleotide which differs from SEQ ID No. 2, SEQ ID No. 4, SEQ ID No. 6, SEQ ID No. 8, SEQ ID No. 10 and SEQ ID No. 12 due to the degeneracy of the genetic code.

In another embodiment the polypeptide may be encoded by a polynucleotide having at least 93% identity with SEQ ID No. 2, SEQ ID No. 4, SEQ ID No. 6, SEQ ID No. 8, SEQ ID No. 10 and SEQ ID No. 12; or at least 93% identity with a polynucleotide which differs from SEQ ID No. 2, SEQ ID No. 4, SEQ ID No. 6, SEQ ID No. 8, SEQ ID No. 10 and SEQ ID No. 12 due to the degeneracy of the genetic code.

In another embodiment the polypeptide may be encoded by a polynucleotide having at least 95% identity with SEQ ID No. 2, SEQ ID No. 4, SEQ ID No. 6, SEQ ID No. 8, SEQ ID No. 10 and SEQ ID No. 12; or at least 95% identity with a polynucleotide which differs from SEQ ID No. 2, SEQ ID No. 4, SEQ ID No. 6, SEQ ID No. 8, SEQ ID No. 10 and SEQ ID No. 12 due to the degeneracy of the genetic code.

In a preferred embodiment, the polypeptide of the present invention is encoded by a polynucleotide selected from the group consisting of: SEQ ID No. 2, SEQ ID No. 4, SEQ ID No. 6, SEQ ID No. 8, SEQ ID No. 10 and SEQ ID No. 12; or a polynucleotide which differs from SEQ ID No. 2, SEQ ID No. 4, SEQ ID No. 6, SEQ ID No. 8, SEQ ID No. 10 and SEQ ID No. 12 due to the degeneracy of the genetic code.

In one embodiment, the polypeptide of the present invention is encoded by polynucleotide comprising the nucleotide sequence shown herein as SEQ ID No. 2 or a polynucleotide which differs from SEQ ID No. 2 due to the degeneracy of the genetic code.

Suitably, the nucleic acid or polynucleotide sequences taught herein may be genomic DNA, cDNA, synthetic DNA, or RNA.

In one embodiment, the nucleic acid or polynucleotide sequences taught herein may be DNA, more preferably cDNA In one embodiment, the present invention provides a nucleic acid construct comprising the polynucleotide of the present invention operably linked to one or more control sequences that direct the production of the polypeptide in an expression host.

Also contemplated is a recombinant expression vector comprising the nucleic acid construct of the present invention or polynucleotides of the present invention; and host cells (e.g. recombinant host cells) comprising the nucleic acid construct of the present invention or polynucleotides of the present invention; or vectors according to the present invention.

In one embodiment a method for producing the polypeptide of the present invention comprising (a) cultivating a host cell comprising a nucleic acid construct according to the present invention under conditions conducive for production of the polypeptide; and (b) recovering the polypeptide is taught.

The polypeptide so produced may be recovered. The polypeptide so produced may be used as part of a fermentate or may be isolated and/or purified to produce an isolated or purified synthetic xylanase.

In one preferred embodiment the synthetic xylanase produced in accordance with a method of the present invention is recovered.

In one preferred embodiment the synthetic xylanase produced in accordance with a method of the present invention is isolated and/or purified.

In some embodiments the synthetic xylanase may be used directly as a fermentate without isolation and/or purification of the enzyme.

The host cell of the present invention may be selected from the group consisting of a bacterial cell, fungal cell, a yeast cell, a filamentous fungal cell and a plant cell. Preferably the host cell is a bacterial or fungal cell.

In one embodiment preferably the synthetic xylanase is an endoxylanase, e.g. an endo-1,4-β-d-xylanase. The classification for an endo-1,4-β-d-xylanase is E.C. 3.2.1.8.

In one preferred embodiment the polypeptide of the present invention has at least 40% residual activity of xylanase activity after incubation at 65° C. for 10 minutes at pH 6.

In one preferred embodiment the polypeptide of the present invention has at least 50% residual activity of xylanase activity after incubation at 65° C. for 10 minutes at pH 6.

In another preferred embodiment the polypeptide of the present invention has at least 80% residual activity of xylanase activity after incubation at 61° C. for 10 minutes at pH 6.

Suitably, the polypeptide of the present invention has a residual activity of at least 70% when incubated with 0.2 mg/ml pepsin in a buffered solution at pH3.5 for two hours at a temperature of 40° C.

In a preferred embodiment, the polypeptide of the present invention has at least 60% residual xylanase activity after a feed comprising the polypeptide has been treated with dry steam to reach a target temperature of 90° C. after 30 seconds.

In a preferred embodiment, the polypeptide of the present invention has at least 60% residual xylanase activity after a feed comprising the polypeptide has been conditioned for 30 seconds at 90° C., e.g. as part of a pelleting process.

In a preferred embodiment, the synthetic xylanase according to the present invention has a Tm value of more than 61° C. (preferably more than 65° C., preferably more than 69° C., preferably more than 73° C.), wherein the Tm value is measured as the temperature at which 50% residual activity is obtained after 10 min incubation.

The thermostability of the synthetic xylanase in accordance with the present invention may be determined using the "Assay for measurement of thermostability" (see below).

Assay for Measurement of Thermostability

The thermal denaturation profiles of the synthetic xylanases was measured by diluting and pre-incubating the enzyme samples in 25 mM MES buffer, pH 6.0 for 10 min at varying temperatures (e.g. 61, 65, 69 and 73° C., respectively) and subsequently measuring the residual activity by the xylanase Activity Assay described in Example 2. Activity measured without pre-incubation was set to 100% and the residual activity of each synthetic xylanase at each temperature was calculated as relative to this. Tm value is calculated from the thermal denaturation profiles as the temperature at which 50% residual activity is obtained.

Full details of the Assay for measurement of thermostability can be found in Example 2 (see "Thermostability Assay").

The residual activity of each synthetic xylanase was calculated as the ratio between activity measured for the stressed (heat treated) and unstressed (not heat treated) enzyme samples respectively: (Mean blanked activity of stressed sample)/(Mean blanked activity of unstressed sample).

In one embodiment, a synthetic xylanase is considered to be thermostable in accordance with the present invention if it has a Tm value of more than 65° C., wherein the Tm value is the temperature at which 50% residual activity is obtained after 10 min incubation. This Tm value may be measured in accordance with the assay for measurement of thermostability as taught herein.

In one embodiment, a synthetic xylanase is considered to be thermostable in accordance with the present invention if it has a Tm value of more than 69° C., wherein the Tm value is the temperature at which 50% residual activity is obtained after 10 min incubation. This Tm value may be measured in accordance with the assay for measurement of thermostability as taught above In one embodiment, a synthetic xylanase is considered to be thermostable in accordance with the present invention if it has a Tm value of more than 73° C., wherein the Tm value is the temperature at which 50% residual activity is obtained after 10 min incubation. This Tm value may be measured in accordance with the assay for measurement of thermostability as taught herein.

A surprising technical advantage of the synthetic xylanase (or composition comprising the synthetic xylanase) is that they are markedly good at withstanding a heat treatment (e.g. during the pelleting process for example) of up to about 85° C. (suitably up to about 90° C.). The heat treatment may be performed for 30 seconds. To withstand such heat treatment means that at least about 40%, suitably at least 50%, of the enzyme that was present/active in the additive before heating to the specified temperature is still present/active after it cools to room temperature. Preferably, at least about 60% (suitably at least about 70%, suitably at least about 80%) of the enzyme that is present and active in the additive before heating to the specified temperature is still present and active after it cools to room temperature.

The term "thermostability" is the ability of an enzyme to resist irreversible inactivation (usually by denaturation) at a relatively high temperature. This means that the enzyme retains a specified amount of enzymatic activity after exposure to an identified temperature over a given period of time.

There are many ways of measuring thermostability. By way of example, enzyme samples maybe incubated without substrate for a defined period of time (e.g. 10 min or 1 to 30 min) at an elevated temperature compared to the temperature at which the enzyme is stable for a longer time (days). Following the incubation at elevated temperature the enzyme sample is assayed for residual activity at the permissive temperature of e.g. 30° C. (alternatively 25-50° C. or even up to 70° C.). Residual activity is calculated as relative to a sample of the enzyme that has not been incubated at the elevated temperature.

Thermostability can also be measured as enzyme inactivation as function of temperature. Here enzyme samples are incubated without substrate for a defined period of time (e.g. 10 min or 1 to 30 min) at various temperatures and following incubation assayed for residual activity at the permissive temperature of e.g. 30° C. (alternatively 25-70° C. or even higher). Residual activity at each temperature is calculated as relative to a sample of the enzyme that has not been incubated at the elevated temperature. The resulting thermal denaturation profile (temperature versus residual activity) can be used to calculate the temperature at which 50% residual activity is obtained. This value is defined as the Tm value.

Even further, thermostability can be measured as enzyme inactivation as function of temperature. Here enzyme samples are incubated without substrate at a defined elevated temperature (e.g. 76° C.) for various time periods (e.g. between 10 sec and 30 min) and following incubation assayed for residual activity at the permissive temperature of e.g. 30° C. (alternatively 25-70° C. or even higher). Residual activity at each temperature is calculated as relative to an enzyme sample that has not been incubated at the elevated temperature. The resulting inactivation profile (time versus residual activity) can be used to calculate the time at which 50% residual activity is obtained. This is usually given as T½.

These are examples of how to measure thermostability. Thermostability can also be measured by other methods. Preferably thermostability is assessed by use of the "Assay for measurement of thermostability" as taught herein.

In contradistinction to thermostability, thermoactivity is enzyme activity as a function of temperature. To determine thermoactivity enzyme samples may be incubated (assayed) for the period of time defined by the assay at various temperatures in the presence of substrate. Enzyme activity is obtained during or immediately after incubation as defined by the assay (e.g. reading an OD-value which reflects the amount of formed reaction product). The temperature at which the highest activity is obtained is the temperature optimum of the enzyme at the given assay conditions. The activity obtained at each temperature can be calculated relative to the activity obtained at optimum temperature. This will provide a temperature profile for the enzyme at the given assay conditions.

In the present application thermostability is not the same as thermoactivity.

In some embodiments the enzyme having xylanase activity, e.g. the GH10 xylanase enzyme (such as the modified GH10 xylanase enzyme) or a fragment thereof of the present invention should have good xylanase activity at a pH of between about 5 and 6.

Preferably the enzyme having xylanase activity, e.g. the GH10 xylanase enzyme (such as the modified GH10 xylanase enzyme) or a fragment thereof according to the present invention retains greater than 70% of maximum activity between pH4 and 8, suitably between pH 4.6 and 7.

In some embodiments, e.g. in feed applications, the enzyme having xylanase activity, e.g. the GH10 xylanase enzyme (such as the modified GH10 xylanase enzyme) or a fragment thereof according to the present invention preferably retains greater than 70% of maximum activity between 4.9 and 6.

Without wishing to be bound by theory, pH may also have an important effect on enzyme efficacy and efficiency. For feed applications in particular the pH profile of the xylanases of the present invention favour activity in the small intestine, under neutral conditions.

The present invention further provides an enzyme composition or a feed additive composition comprising the polypeptide of the present invention or the fermentate according to the present invention.

The present invention also provides a premix comprising the polypeptide of the present invention or the fermentate according to the present invention, or the enzyme composition of the present invention, or a feed additive composition according to the present invention and/or at least one mineral.

In some embodiments the feed additive composition according to the present invention or the premix according to the present invention further comprises one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including α-amylases (E.C. 3.2.1.1), G4-forming amylases (E.C. 3.2.1.60), β-amylases (E.C. 3.2.1.2) and γ-amylases (E.C. 3.2.1.3)).

The synthetic xylanase according to the present invention or a fermentate comprising same, or an enzyme composition comprising same may be used in a method for degrading arabinoxylan-containing material in a xylan-containing material.

Suitably, the arabinoxylan may be insoluble arabinoxylan (AXinsol).

In one embodiment the xylan-containing material is selected from one or more of the group consisting of: a feed or feedstuff; a feed component; a grain-based material; a mash; a wort; a malt; malted barley; an adjunct, a barley mash; and a cereal flour.

In a one embodiment the arabinoxylans are solubilized without increasing viscosity in the reaction medium.

In one embodiment of the present invention the feed or feedstuff or feed component comprises or consists of corn, DDGS (such as cDDGS), wheat, wheat bran or a combination thereof.

In one preferred embodiment the feed or feedstuff is a corn-based feedstuff.

The synthetic xylanase according to the present invention may be used in combination with one or more of the enzymes selected from the group consisting of endoglucanases (E.C. 3.2.1.4); celliobiohydrolases (E.C. 3.2.1.91), β-glucosidases (E.C. 3.2.1.21), cellulases (E.C. 3.2.1.74), lichenases (E.C. 3.2.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), amylases, alpha-amylases (E.C. 3.2.1.1), other xylanases (E.C. 3.2.1.8, E.C. 3.2.1.32, E.C. 3.2.1.37, E.C. 3.2.1.72, E.C. 3.2.1.136), glucoamylases (E.C. 3.2.1.3), hemicellulases, proteases (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)), debranching enzymes, cutinases, esterases and/or mannanases (e.g. a β-mannanase (E.C. 3.2.1.78)).

The synthetic xylanase according to the present invention may be used in combination with one or more of the enzymes selected from the group consisting of a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or an amylase (including α-amylases (E.C. 3.2.1.1), G4-forming amylases (E.C. 3.2.1.60), β-amylases (E.C. 3.2.1.2) and γ-amylases (E.C. 3.2.1.3)).

In one embodiment the method or use according to the present invention comprises administering a subject with a synthetic xylanase enzyme according to the present invention, or a fermentate comprising a synthetic xylanase enzyme according to the present invention, or an enzyme composition comprising a synthetic xylanase according to the present invention, or a feed additive composition comprising a synthetic xylanase according to the present invention, or a premix comprising a synthetic xylanase according to the present invention or a feedstuff comprising a synthetic xylanase according to the present invention.

In one embodiment the method or use of the present invention is (or is part of) a wheat gluten-starch separation process.

In another embodiment, the method or use of the present invention is (or is part of) a biofuel (e.g. bioethanol) or biochemical (e.g. bio-based isoprene) production process.

In another embodiment, the method or use of the present invention is (or is part of) a malting or brewing process.

Suitably, a fermented beverage, e.g. beer, produced by a method according to the present invention in envisaged by the present invention.

Both the polypeptide sequences and the nucleic acid sequences taught herein are preferably isolated.

The synthetic xylanase of the present invention is preferably a GH10 xylanase. In other words the xylanase may have a molecular weight in the range of 32-39 kDa and/or the catalytic domain of the xylanase consists of an eightfold β/a barrel structure (as taught in Harris et al 1996—Acta. Crystallog. Sec. D 52, 393-401).

In one aspect of the invention, the xylanase of the invention is a xylanase of Glycoside Hydrolyase (GH) Family 10. The term "of Glycoside Hydrolyase (GH) Family 10" means that the xylanase in question is or can be classified in the GH family 10.

Protein similarity searches (e.g. protein blast at HyperText Transfer protocol: blast.ncbi.nlm.nih.gov/Blast.cgi?CMD=Web&PAGE_TYPE=BlastHome) may determine whether an unknown sequence falls under the term of a GH10 xylanase family member, particularly the GH families may be categorised based on sequence homology in key regions. In addition or alternatively, to determine whether an unknown protein sequence is a xylanase protein within the GH10 family, the evaluation can be done, not only on sequence similarity/homology/identity, but also on 3D structure similarity. The classification of GH-families is often based on the 3D fold. Software that will predict the 3D fold of an unknown protein sequence is HHpred (HyperText Transfer protocol:toolkit.tuebingen.mpg.de/hhpred). The power of this software for protein structure prediction relies on identifying homologous sequences with known structure to be used as template. This works so well because structures diverge much more slowly than primary sequences. Proteins of the same family may have very similar structures even when their sequences have diverged beyond recognition.

In practice, an unknown sequence can be pasted into the software HyperText Transfer protocol toolkit.tuebingen.mpg.de/hhpred) in FASTA format. Having done this, the search can be submitted. The output of the search will show a list of sequences with known 3D structures. To confirm that the unknown sequence indeed is a GH10 xylanase, GH10 xylanases may be found within the list of homologues having a probability of >90. Not all proteins identified as homologues will be characterised as GH10 xylanases, but some will.

The latter proteins are proteins with a known structure and biochemically characterisation identifying them as xylanases. The former have not been biochemically characterised as GH10 xylanases. Several references describes this protocol such as Soding J. (2005) Protein homology detection by HMM-HMM comparison—Bioinformatics 21, 951-960 (doi:10.1093/bioinformatics/bti125) and Söding J, Biegert A, and Lupas A N. (2005) The HHpred interactive server for protein homology detection and structure prediction—Nucleic Acids Research 33, W244-W248 (Web Server issue) (doi:10.1093/nar/gki40).

According to the Cazy site Hyper Text Transfer protocol// world_wide_web.cazy.org/),Family 10 glycoside hydrolases can be characterised as follows:

Known Activities: endo-1,4-β-xylanase (EC 3.2.1.8); endo-1,3-β-xylanase (EC 3.2.1.32); tomatinase (EC 3.2.1.-)

Mechanism: Retaining

Clan: GH-A

Catalytic Nucleophile/Base: Glu (experimental)

Catalytic Proton Donor: Glu (experimental)

3D Structure Status: $(\beta/\alpha)_8$

The GH10 xylanase of the present invention may have a catalytic domain with molecular weights in the range of 32-39 kDa. The structure of the catalytic domain of the GH10 xylanase of the present invention consists of an eightfold β/α barrel (Harris et al 1996—Acta. Crystallog. Sec. D 52, 393-401).

Three-dimensional structures are available for a large number of Family GH10 enzymes, the first solved being those of the *Streptomyces lividans* xylanase A (Derewenda et al J Biol Chem 1994 Aug. 19; 269(33) 20811-4), the *C. fimi* endo-glycanase Cex (White et al Biochemistry 1994 Oct. 25; 33(42) 12546-52), and the *Cellvibrio japonicus* Xyn10A (previously *Pseudomonas fluorescens* subsp. xylanase A) (Harris et al Structure 1994 Nov. 15; 2(11) 1107-16.). As members of Clan GHA they have a classical $(\alpha/\beta)_8$ TIM barrel fold with the two key active site glutamic acids located at the C-terminal ends of beta-strands 4 (acid/base) and 7 (nucleophile) (Henrissat et al *Proc Natl Acad Sci USA* 1995 Jul. 18; 92(15) 7090-4).

The term "GH10 xylanase" as used herein means a polypeptide having xylanase activity and having a $(\alpha/\beta)_8$ TIM barrel fold with the two key active site glutamic acids located at the C-terminal ends of beta-strands 4 (acid/base) and 7 (nucleophile).

In one embodiment, the synthetic xylanase according to the present invention is capable of degrading (or degrades) a xylan-containing material, particularly arabinoxylans, particularly insoluble arabinoxylans (AXinsol).

The term "consisting essentially of" as used herein means that unspecified components may be present if the characteristics of the claimed composition are thereby not materially affected.

The term "consisting of" means that the proportions of the specific ingredients must total 100%.

The term "comprising" used herein may be amended in some embodiments to refer to consisting essentially of or consisting of (both having a more limited meaning that "comprising").

In one embodiment the insoluble arabinoxylan containing material is not wheat straw.

The term "fragment thereof" as used herein means an active fragment. In other words the fragment is one which has xylanase activity. Suitably the fragment may have the same xylanase activity as the full length synthetic xylanase enzyme from which the fragment is derived. Alternatively, the fragment may have a modified activity (e.g. enhanced specificity, specific activity, pH or temperature profile) compared with the synthetic xylanase from which the fragment is derived. In addition the fragment must retain the thermostable properties of the synthetic xylanase of which it is a fragment.

In one embodiment the fragment is at least 60% of the full length of the synthetic xylanase from which the fragment is derived.

In one embodiment the fragment is at least 75% of the full length of the synthetic xylanase from which the fragment is derived.

In one embodiment the fragment is at least 85% of the full length of the synthetic xylanase from which the fragment is derived.

In one embodiment the fragment is at least 95% of the full length of the synthetic xylanase from which the fragment is derived.

In one embodiment the fragment is at least 98% of the full length of the synthetic xylanase from which the fragment is derived.

In one embodiment the fragment is a fragment of one or more of the sequences selected from the group consisting of SEQ ID No. 1, SEQ ID No: 3, SEQ ID No. 5, SEQ ID No. 7, SEQ ID No. 9 and SEQ ID No. 11.

In one embodiment the synthetic xylanase according to the present invention a) comprises one of the amino acid sequences shown herein as SEQ ID No. 1, SEQ ID No: 3, SEQ ID No. 5, SEQ ID No. 7, SEQ ID No. 9 or SEQ ID No. 11, or b) comprises an amino acid sequence which is at least 96%, preferably at least 98.5%, preferably at least 99%, identical with the amino acid sequences shown herein as SEQ ID No. 1, SEQ ID No: 3, SEQ ID No. 5, SEQ ID No. 7, SEQ ID No. 9 or SEQ ID No. 11, or c) comprises a fragment which is at least 85% of the full length of the synthetic xylanase shown herein as SEQ ID No. 1, SEQ ID No: 3, SEQ ID No. 5, SEQ ID No. 7, SEQ ID No. 9 or SEQ ID No. 11.

Uses

The synthetic xylanase of the present invention can be suitably used in any one of the following applications:

a) An additive in animal feedstuffs; and/or b) A feed supplement for an animal; and/or c) Breakdown of grain-based material (e.g. this can be whole grain or part of grain). The breakdown products (e.g. glucose) can be used as a feedstock for any fermentation process, such as in biofuel (e.g. bioethanol) production or in the production of other products such as biochemicals (e.g., bio-based isoprene). Therefore in one embodiment the present invention relates to the production of biofuel (e.g. bioethanol) and to the enhanced utilisation of grain-based material in the biofuel industry; and/or d) Cereal (e.g. wheat) gluten-starch separation industry. The resultant product(s) may be starch (e.g. purified starch) and/or gluten and/or fibres and/or water solubles (such as soluble pentosans). In one embodiment the present invention relates to the production of starch and/or gluten; and/or e) Improving malting and brewing, e.g. by breaking down grain-based material (e.g. malted barley) and/or f) to degrade AXsol or the breakdown products of AXinsol to ensure viscosity is not increased and/or viscosity is reduced in the reaction mixture; and/or g) to reducing viscosity when degrading grain-based materials, e.g. in biofuel (e.g. bioethanol) production processes.

In one embodiment the synthetic xylanase of the present invention is used in a feedstuff. Preferably a feedstuff comprising corn or is a corn-based feedstuff.

In one embodiment the synthetic xylanase of the present invention is used in malting or brewing.

In a further embodiment the synthetic xylanase of the present invention is used in wheat gluten-starch separation.

In a yet further embodiment the synthetic xylanase of the present invention is used in the breakdown of grain-based material and may be part of the biofuel (e.g. bioethanol) production process.

Advantages

The novel synthetic xylanase taught herein has many advantages compared with known xylanases.

In addition, the synthetic xylanase of the present invention is particularly thermostable. This provides significant advantages in some applications. In particular, in feed applications, enzymes can be subject to heat treatment, e.g. during pelleting processes. Thus the enzymes need to be able to maintain their activity after such processing. The synthetic xylanase of the present invention are particularly and unexpectedly thermostable. Specifically the synthetic xylanase of the present invention have been found to have very high recovery (e.g. residual activity) after the pelleting process.

Suitably the synthetic xylanase has a Tm value of more than 65° C., wherein the Tm value is the temperature at which 50% residual activity is obtained after 10 min incubation.

Furthermore, an improved thermostability is also very beneficial during degradation of starch, which takes place at elevated temperatures during liquefaction (around 85-95 C). Being thermostable allows the addition of the enzyme during this step.

In addition or alternatively it has been found that the synthetic xylanases are unexpectedly highly pepsin resistant.

Pepsin is a digestive protease excreted by an animal in the first part of the digestive system. Pepsin degrades protein which makes the protein available as a nutrient for the animal. The exogenous enzymes, i.e. enzymes added to the feed, are also proteins and they will be degraded if they are susceptible to degradation by the pepsin. This will in most cases destroy the enzyme activity. Thus, it is highly advantageous that the synthetic xylanases have pepsin resistance.

The synthetic xylanase as taught herein and of the present invention are also unexpectedly good at solubilising pentosans.

The synthetic xylanase as taught herein and of the present invention are unexpectedly good at solubilising AXinsol.

Surprisingly it has been found that the synthetic xylanase of the present invention is particularly good at degrading xylan-containing materials, such as arabinoxylans, e.g. AXinsol, in a broad spectrum of substrates, corn, wheat, DDGS, etc., in particular corn and corn based substrates, in particular both wheat (including wheat-based) products and corn (including corn-based products). This contrasts with prior-known enzymes, which are often inferior at solubilising AXinsol in corn or corn-based substrates or which are not as efficient in both wheat- and corn-based substrates.

In addition, the synthetic xylanase of the present invention may be particularly good at not only breaking down (solubilising) AXinsol, but also breaking down (or degrading) the solubilized polymers efficiently. By being able to efficiently (quickly) breakdown (degrade) the solubilized polymers (obtained from dissolving AXinsol) a reduction in viscosity is obtained. This latter effect is essential in some of the claimed applications.

Typically, conventional xylanases may breakdown AXinsol, but will lead to an increase is the polymer production products which will lead to an increase in viscosity of the mixture. This increased viscosity is disadvantageous in many applications.

The synthetic xylanase of the present invention and as described herein have been found to not only breakdown (solubilise) insoluble arabinoxylans (AXinsol) from a wide range of substrates, including corn, wheat, DDGS, etc., in particular corn and corn-based substrates, in particular both wheat (including wheat-based) products and corn (including corn-based products), but also efficiently breakdown the thus solubilised polymers to ensure viscosity is not raised and/or to reduce viscosity.

In some embodiments, the synthetic xylanases of the present invention and as described herein are capable of degrading AXsol or the breakdown products of AXinsol to ensure viscosity is not increased and/or viscosity is reduced in the reaction mixture.

In particular the synthetic xylanase of the present invention is particularly effective at degrading xylan-containing materials, such as arabinoxylans, e.g. AXinsol, in corn and corn based substrates.

Many of the xylanases commercialized for use in feedstuffs for solubilizing pentosans are GH11 enzymes. It had been considered by those skilled in the art that GH10 xylanases were not as strong at solubilizing pentosans, particularly AXinsol, compared with GH11 xylanases. Surprisingly it has been found that the synthetic xylanase(s) disclosed herein which are GH10 xylanases are particularly good at solubilizing AXinsol in a broad spectrum of substrates, including corn based substrates. Surprisingly, the present inventors have found that the synthetic xylanases of the present invention (and taught herein) outperform commercial GH11 xylanases in their ability to solubilize pentosans.

The fact that the synthetic xylanases efficiently solubilize AXinsol from corn and corn-based substrates is significantly advantageous as corn holds much more AX in the insoluble form compared with other cereals, such as wheat and rye for example. Therefore only xylanases that can breakdown AXinsol can show significant benefit to animals fed on corn-soy diet for example.

It was completely unexpected for a GH10 xylanase to be so good on solubilizing AXinsol in cereals, particularly in corn or corn-based substrates.

The synthetic xylanase of the present invention are able to efficiently (and quickly) degrade the polymers and/or oligomers that are produced from solubilisation of AXinsol or that are present in grain-based materials. This leads to an unexpected advantage for the synthetic xylanase taught herein in that they are particularly good in a number of applications to keep viscosity low or to reduce viscosity, e.g. in feedstuffs; in brewing and/or malting; in grain-based production of glucose, e.g. for further processing to biofuels and/or biochemicals (e.g., bio-based isoprene); or in the wheat gluten-starch separation industry for the production of starch for example.

One advantage of the present invention is that it improves wheat gluten-starch separation.

The enzyme of the present invention is particularly effective at enhancing the performance of a subject or improving the digestibility of a raw material in a feed and/or for improving feed efficiency in a subject.

Xylan-Containing Material

The synthetic xylanase of the present invention (or composition comprising the synthetic xylanase of the present invention) may be used to degrade any xylan-containing material.

In one embodiment the xylan-containing material is any plant material comprising arabinoxylan.

In one embodiment the xylan-containing material is any plant material comprising insoluble arabinoxylan (AXinsol).

In one embodiment the xylan-containing material is a feedstuff or feed component.

In one embodiment the xylan-containing material is a grain-based material (including whole grains or partial grains or malted grains, e.g. malted barley). When the method relates to biofuel production (e.g. bioethanol production) then preferably the xylan-containing material is a grain-based material.

In another embodiment the xylan-containing material may be barley malt or mash, or malted barley or combinations thereof.

In a yet further embodiment the xylan-containing material may be a cereal flour (e.g. wheat, oat, rye or barley flour). When the method relates to a gluten-starch separation process preferably the xylan-containing material is a cereal flour (e.g. wheat oat, rye or barley flour).

Breakdown or Degradation

The enzyme (or composition comprising the enzyme) of the present invention or as disclosed herein may be used to breakdown (degrade) AXinsol or AXsol or degradation products of AXinsol.

The term "breakdown" or "degrade" in synonymous with hydrolyses.

Solubilisation/Degradation

The present invention relates to a method of degrading a xylan-containing material (preferably an arabinoxylan-containing material, preferably an insoluble arabinoxylan (AXinsol)-containing material) to produce soluble pentosans (which can be polymeric, oligomeric or monomeric).

This method may be described herein as pentosan solubilisation or arabinoxylan solubilisation or AXinsol solubilisation or degradation of AXinsol.

In one embodiment, the present invention relates to a method of degrading (or breaking down) insoluble arabinoxylan (AXinsol). This can also be referred to as solubilisation of insoluble arabinoxylan and/or solubilisation of pentosans.

In a further embodiment of the present invention the method relates to degrading (e.g. breaking down) polymers derived from the degradation of insoluble arabinoxylans.

Arabinoxylan (AX)

The term "arabinoxylans" (AX) as used herein means a polysaccharide consisting of a xylan backbone (1,4-linked xylose units) with L-arabinofuranose (L-arabinose in its 5-atom ring form) attached randomly by $1\alpha \rightarrow 2$ and/or $1\alpha \rightarrow 3$ linkages to the xylose units throughout the chain. Arabinoxylan is a hemicellulose found in both the primary and secondary cell walls of plants. Arabinoxylan can be found in the bran of grains such as wheat, maize (corn), rye, and barley.

Arabinoxylan (AX) is found in close association with the plant cell wall, where it acts as a glue linking various building blocks of the plant cell wall and tissue, give it both structural strength and rigidity.

The term "pentosan" as used herein is any of a group of carbohydrates which yield pentoses on complete hydrolysis.

Since xylose and arabinose (the constituents of arabinoxylans) are both pentoses, arabinoxylans are usually classified as pentosans.

AX is the principal Non Starch Polysaccharide (NSP)-fraction in several of the most important feed raw material, including wheat and corn.

Its abundance, location within vegetable material and molecular structure cause AX to have a severe, negative impact on feed digestibility, effectively reducing the nutritional value of the raw materials in which it is present. This makes AX an important anti-nutritional factor, reducing animal production efficiency.

In addition AX can have a severe, negative impact when trying to breakdown plant material for example in processes such as brewing, malting, biofuel manufacture, effectively reducing the amount of substrate accessible in the raw plant material.

AXs can also hold substantial amounts of water (which can be referred to as their water holding capacity)—this can cause soluble arabinoxylans to result in (high) viscosity—which is a disadvantage in many applications.

The term "Hemicellulose"—as used herein means the polysaccharide components of plant cell walls other than cellulose. The term "hemicellulose" as used herein may mean polysaccharides in plant cell walls which are extractable by dilute alkaline solutions.

Hemicelluloses comprise almost one-third of the carbohydrates in woody plant tissue. The chemical structure of hemicelluloses consists of long chains of a variety of pentoses, hexoses, and their corresponding uronic acids. Hemicelluloses may be found in fruit, plant stems, and grain hulls. Xylan is an example of a pentosan consisting of D-xylose units with $1\beta \rightarrow 4$ linkages.

Water Insoluble Arabinoxylan (AXinsol)

Water-insoluble arabinoxylan (AXinsol) also known as water-unextractable arabinoxylan (WU-AX) constitutes a significant proportion of the dry matter of plant material.

In wheat, AXinsol can account for 6.3% of the dry matter. In wheat bran and wheat DDGS, AXinsol can account for about 20.8% or 13.4% of the dry matter (w/w).

In rye, AXinsol can account for 5.5% of the dry matter.

In corn, AXinsol can account for 3.5-6% (e.g. 5.1%) of the dry matter. In corn DDGS AXinsol can account for 10-20% (e.g. 12.6%) of the dry matter.

AXinsol causes nutrient entrapment in feed. Large quantities of well digestible nutrients such as starch and proteins remain either enclosed in clusters of cell wall material or bound to side chains of the AX. These entrapped nutrients will not be available for digestion and subsequent absorption in the small intestine.

Water-Soluble Arabinoxylan (AXsol)

Water-soluble arabinoxylan (AXsol) also known as water extractable arabinoxylan (WE-AX) can cause problems in biofuel production, biochemical production, carbohydrate processing and/or malting and/or brewing and/or in feed as they can cause increased viscosity due to the water-binding capacity of AXsol.

In feed AXsol can have an anti-nutritional effect particularly in monogastrics as they cause a considerable increase of the viscosity of the intestinal content, caused by the extraordinary water-binding capacity of AXsol. The increase viscosity can affect feed digestion and nutrient use as it can prevent proper mixing of feed with digestive enzymes and bile salts and/or it slows down nutrient availability and absorption and/or it stimulates fermentation in the hindgut.

In wheat, AXsol can account for 1.8% of the dry matter. In wheat bran and wheat DDGS, AXsol can account for about 1.1% or 4.9% of the dry matter (w/w).

In rye, AXsol can account for 3.4% of the dry matter.

In barley, AXsol can account for 0.4-0.8% of the dry matter.

In corn, AXsol can account for 0.1-0.4% (e.g. 0.1%) of the dry matter. In corn DDGS AXinsol can account for 0.3-2.5% (e.g. 0.4%) of the dry matter.

In addition, however, to the amount of AXsol present in plant material, when a xylanase solubilises AXinsol in the plant material this can release pentosans and/or oligomers which contribute to AXsol content of the plant material.

One significant advantage of the modified xylanases disclosed herein is that they have the ability to solubilise AXinsol without increasing viscosity. It is presently believed that high molecular weight products are not formed.

A breakdown of AXsol can decrease viscosity.

A breakdown of AXsol can release nutrients.

Viscosity

The present invention can be used to ensure that the viscosity is not increased and/or to reduce viscosity in any process where the water-binding capacity of AXsol causes an undesirable increase in viscosity.

The present invention relates to ensuring that viscosity is not increased and/or to reducing viscosity by breaking down (degrading) AXsol or by breaking down (degrading) the polymers and/or oligomers produced by solubilising AXinsol.

Without wishing to be bound by theory, by being able to efficiently (quickly) breakdown (degrade) the solubilized polymers (e.g. oligomers) obtained from dissolving AXinsol an undesirable increase in viscosity can be avoided and/or a reduction in viscosity can be obtained. The term "efficiently" as used herein means that the enzyme is capable of degrading the polymers (e.g. oligomers) being formed by solubilisation of the AXinsol faster than the speed with which the AXinsol is degraded (or solubilized).

Reducing viscosity has advantages in many applications as taught herein.

An example of a xylanase used in the bioethanol industry is Xylathin™ An example of a Xylanase used in the wheat gluten-starch separation Industry is Shearzyme™.

In one embodiment of the present invention the xylanases taught herein are viscosity reducers.

Generally, wheat (or other cereal) is first dry-milled to separate the bran and germ from the endosperm, which is ground into flour. This endosperm flour is then further fractionated through a wheat starch separation process into several product streams of varying commercial value. The major aim is to produce a refined grade of A-starch, consisting of large, lenticular granules of 15-40 µm. The second stream B-starch consists of less purified starch granules, which are spherical and small (1-10 µm). (C. C. Maningat, P. A. Seib, S. D. Bassi, K. S. Woo, G. D. Lasater, Chapter 10 from the book "*Starch*" (2009) 441-451, *Wheat starch: production, properties, modification and uses*). Isolated wheat starch forms the starting material for modified starch production with applications in both food- and nonfood-applications. Vital gluten is the third product of added-value in wheat separation processes.

The vitality of the isolated wheat gluten is determined by the ability to form viscoelastic networks, required for breadmaking. Vital gluten encapsulates the carbon dioxide formed in dough preparation during baking, and consequently increases the bread volume. (Anne van der Borght, Hans Goesaert, Wim S. Veraverbeke, Jan A. Delcour, *Journal of Cereal Science* 41 (2005) 221-237, Fractionation of wheat and wheat flour into starch and gluten: overview of the main processes and the factors involved.) It is therefore often used to enrich flours for bread making, to achieve improved bread products. Other markets for gluten include as an additive in vegetarian, meat, fish or poultry products, including those in pet-food industry; in cereal breakfast; or in soy sauce. Due to its thermoplasticity and good film-forming properties, gluten is also used in non-food markets as adhesives. (L. Day, M. A. Augustin, I. L. Batey, C. W Wrigley, *Trends in Food Science & Technology* 17 (2006) 82-90, *Wheat-gluten uses and industry needs*.).

The synthetic xylanases taught herein can be used to reduce the viscosity (or not increase viscosity) in processes for separating cereal flour (e.g. wheat, oat, rye or barley flour) into starch and gluten fractions and to improve the separation by degrading oligosaccharides that hinder gluten agglomeration.

Wort viscosity, and the viscosity of barley mash and barley malt in brewing and malting can cause significant disadvantages during brewing and/or malting. The present invention relates to reducing the viscosity (or not increase the viscosity) of wort, barley mash, barley malt or a combination thereof.

Feed or Feedstuff

The synthetic xylanase or feed additive composition of the present invention may be used as—or in the preparation of—a feed.

The term "feed" is used synonymously herein with "feedstuff".

Preferably the arabinoxylan-containing material of the present invention is a feedstuff, or a constituent of a feedstuff, or a feed component.

The feed may be in the form of a solution or as a solid or as a semi-solid—depending on the use and/or the mode of application and/or the mode of administration.

When used as—or in the preparation of—a feed—such as functional feed—the enzyme or composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

In a preferred embodiment the enzyme or feed additive composition of the present invention is admixed with a feed component to form a feedstuff.

The term "feed component" as used herein means all or part of the feedstuff. Part of the feedstuff may mean one constituent of the feedstuff or more than one constituent of the feedstuff, e.g. 2 or 3 or 4. In one embodiment the term "feed component" encompasses a premix or premix constituents.

Preferably the feed may be a fodder, or a premix thereof, a compound feed, or a premix thereof. In one embodiment the feed additive composition according to the present invention may be admixed with a compound feed, a compound feed component or to a premix of a compound feed or to a fodder, a fodder component, or a premix of a fodder.

The term "fodder" as used herein means any food which is provided to an animal (rather than the animal having to forage for it themselves). Fodder encompasses plants that have been cut.

The term fodder includes silage, compressed and pelleted feeds, oils and mixed rations, and also sprouted grains and legumes.

Fodder may be obtained from one or more of the plants selected from: corn (maize), alfalfa (Lucerne), barley, birdsfoot trefoil, brassicas, Chau moellier, kale, rapeseed (canola), rutabaga (swede), turnip, clover, alsike clover, red clover, subterranean clover, white clover, fescue, brome, millet, oats, sorghum, soybeans, trees (pollard tree shoots for tree-hay), wheat, and legumes.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

Any feedstuff of the present invention may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grain (DDG) (particularly corn based Distillers Dried Grain (cDDG)), Distillers Dried Grain Solubles (DDGS) (particularly corn based Distillers Dried Grain Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

In one embodiment the feedstuff comprises or consists of corn, DDGS (such as cDDGS), wheat, wheat bran or a combination thereof.

In one embodiment the feed component may be corn, DDGS (e.g. cDDGS), wheat, wheat bran or a combination thereof.

In one embodiment the feedstuff comprises or consists of corn, DDGS (such as cDDGS) or a combination thereof.

In one embodiment a feed component may be corn, DDGS (such as cDDGS) or a combination thereof.

A feedstuff of the present invention may contain at least 30%, at least 40%, at least 50% or at least 60% by weight corn and soybean meal or corn and full fat soy, or wheat meal or sunflower meal.

A feedstuff of the present invention may contain between about 5 to about 40% corn DDGS. For poultry—the feedstuff on average may contain between about 7 to 15% corn DDGS. For swine (pigs)—the feedstuff may contain on average 5 to 40% corn DDGS.

A feedstuff of the present invention may contain corn as a single grain, in which case the feedstuff may comprise between about 35% to about 80% corn.

In feedstuffs comprising mixed grains, e.g. comprising corn and wheat for example, the feedstuff may comprise at least 10% corn.

In addition or in the alternative, a feedstuff of the present invention may comprise at least one high fibre feed material and/or at least one by-product of the at least one high fibre feed material to provide a high fibre feedstuff. Examples of high fibre feed materials include: wheat, barley, rye, oats, by products from cereals, such as corn gluten meal, corn gluten feed, wet-cake, Distillers Dried Grain (DDG), Distillers Dried Grain Solubles (DDGS), wheat bran, wheat middlings, wheat shorts, rice bran, rice hulls, oat hulls, palm kernel, and citrus pulp. Some protein sources may also be regarded as high fibre: protein obtained from sources such as sunflower, lupin, fava beans and cotton.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wet-cake, Distillers Dried Grain (DDG)—particularly cDDG, wheat bran, and wheat for example.

In one embodiment the feedstuff of the present invention comprises at least one high fibre material and/or at least one by-product of the at least one high fibre feed material selected from the group consisting of Distillers Dried Grain Solubles (DDGS)—particularly cDDGS, wheat bran, and wheat for example.

In the present invention the feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" in the present invention encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

The term "feed" in the present invention encompasses in some embodiments fish food. A fish food normally contains macro nutrients, trace elements and vitamins necessary to keep captive fish in good health. Fish food may be in the form of a flake, pellet or tablet. Pelleted forms, some of which sink rapidly, are often used for larger fish or bottom feeding species. Some fish foods also contain additives, such as beta carotene or sex hormones, to artificially enhance the color of ornamental fish.

The term "feed" in the present invention encompasses in some embodiment bird food. Bird food includes food that is used both in birdfeeders and to feed pet birds. Typically bird food comprises of a variety of seeds, but may also encompass suet (beef or mutton fat).

As used herein the term "contacted" refers to the indirect or direct application of the enzyme (or composition comprising the enzyme) of the present invention to the product (e.g. the feed). Examples of the application methods which may be used, include, but are not limited to, treating the product in a material comprising the feed additive composition, direct application by mixing the feed additive composition with the product, spraying the feed additive composition onto the product surface or dipping the product into a preparation of the feed additive composition.

In one embodiment the feed additive composition of the present invention is preferably admixed with the product (e.g. feedstuff). Alternatively, the feed additive composition may be included in the emulsion or raw ingredients of a feedstuff.

For some applications, it is important that the composition is made available on or to the surface of a product to be affected/treated. This allows the composition to impart one or more of the following favourable characteristics: performance benefits.

The synthetic xylanase (or composition comprising the synthetic xylanase) of the present invention may be applied to intersperse, coat and/or impregnate a product (e.g. feedstuff or raw ingredients of a feedstuff) with a controlled amount of said enzyme.

In a particularly preferred embodiment the enzyme (or composition comprising the enzyme) of the present invention is homogenized to produce a powder.

In an alternative preferred embodiment, the enzyme (or composition comprising the enzyme) of the present invention is formulated to granules as described in WO2007/044968 (referred to as TPT granules) or WO1997/016076 or WO1992/012645 incorporated herein by reference.

In another preferred embodiment when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme.

Preferably, the salt used for the salt coating has a water activity greater than 0.25 or constant humidity greater than 60% at 20° C.

Preferably, the salt coating comprises a $Na_2SO_4$.

The method of preparing an enzyme (or composition comprising the enzyme) of the present invention may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour.

It will be understood that the enzyme (or composition comprising the enzyme) of the present invention is suitable for addition to any appropriate feed material.

It will be understood by the skilled person that different animals require different feedstuffs, and even the same animal may require different feedstuffs, depending upon the purpose for which the animal is reared.

Optionally, the feedstuff may also contain additional minerals such as, for example, calcium and/or additional vitamins.

Preferably, the feedstuff is a corn soybean meal mix.

In one embodiment, preferably the feed is not pet food.

In another aspect there is provided a method for producing a feedstuff. Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting—in particular by suitable techniques that may include at least the use of steam.

The feedstuff may be a feedstuff for a monogastric animal, such as poultry (for example, broiler, layer, broiler breeders, turkey, duck, geese, water fowl), and swine (all age categories), a ruminant such as cattle (e.g. cows or bulls (including calves)), horses, sheep, a pet (for example dogs, cats) or fish (for example agastric fish, gastric fish, freshwater fish such as salmon, cod, trout and carp, e.g. koi carp, marine fish such as sea bass, and crustaceans such as shrimps, mussels and scallops). Preferably the feedstuff is for poultry.

Corn Based Feedstuff

In a preferred embodiment the feedstuff may be a corn based feedstuff. The term "corn based feedstuff" as used herein means a feedstuff which comprises or consists of corn (maize) or a by-product of corn.

Preferably the corn based feedstuff comprises corn or a by-product of corn as the major constituent. For example the corn based feedstuff may comprise at least 35% corn or a by-product of corn, such as at least 40% corn or a by-product of corn, such as at least 50% corn or a by-product of corn, such as at least 60% corn or a by-product of corn, such as at least 70% corn or a by-product of corn, such as at least 80% or a by-product of corn, such as at least 90% corn or a by-product of corn, for example 100% corn or a by-product of corn.

In some embodiments the corn based feedstuff may comprise corn or a by-product of corn as a minor constituent; in which case the feedstuff may be supplemented with corn or a by-product of corn. By way of example only the feedstuff may comprise for example wheat supplemented with corn or a by-product of corn.

When corn or the by-product of corn is a minor constituent of the feedstuff, the corn or by-product of corn is at least 5%, preferably at least 10%, preferably at least 20%, preferably at least 30% of the feedstuff.

For the avoidance of doubt the term "corn" as used herein is synonymous with maize, e.g. Zea mays.

In one embodiment the by-product of corn may be corn Distillers Dried Grain Solubles (cDDGS) or corn wet-cake or corn Distillers Dried Grain (DDG) or corn gluten meal or corn gluten feed or combinations thereof.

In one embodiment preferably the arabinoxylan-containing material of the present invention comprises a by-product of corn, such as corn Distillers Dried Grain Solubles (cDDGS) or corn wet-cake or corn Distillers Dried Grain (DDG) or corn gluten meal or corn gluten feed or combinations thereof.

Wheat Based Feedstuff

In a preferred embodiment the feedstuff may be a wheat based feedstuff. The term "wheat based feedstuff" as used herein means a feedstuff which comprises or consists of wheat or a by-product of wheat.

Preferably the wheat based feedstuff comprises wheat or a by-product of wheat as the major constituent. For example the wheat based feedstuff may comprise at least 40% wheat or a by-product of wheat, such as at least 60% wheat or a by-product of wheat, such as at least 80% or a by-product of wheat, such as at least 90% wheat or a by-product of wheat, for example 100% wheat or a by-product of wheat.

In some embodiments the wheat based feedstuff may comprise wheat or a by-product of wheat as a minor constituent; in which case the feedstuff may be supplemented with wheat or a by-product of wheat. By way of example only the feedstuff may comprise for example wheat supplemented with wheat or a by-product of wheat.

When wheat or the by-product of wheat is a minor constituent of the feedstuff, the wheat or by-product of wheat is at least 5%, preferably at least 10%, preferably at least 20%, preferably at least 30% of the feedstuff.

In one embodiment the by-product of wheat may be wheat bran, wheat middlings, wheat fibres for example.

Bran is the hard outer layer of grain and consists of combined aleurone and pericarp. Along with germ, it is an integral part of whole grains, and is often produced as a by-product of milling in the production of refined grains. When bran is removed from grains, the grains lose a portion of their nutritional value. Bran is present in and may be milled from any cereal grain, including rice, corn (maize), wheat, oats, barley and millet. Bran is particularly rich in dietary fiber and essential fatty acids and contains significant quantities of starch, protein, vitamins and dietary minerals.

Wheat middlings is coarse and fine particles of wheat bran and fine particles of wheat shorts, wheat germ, wheat flour and offal from the "tail of the mill".

Wheat middlings is an inexpensive by-product intermediate of human food and animal feed. In one embodiment preferably the arabinoxylan-containing material of the present invention comprises wheat bran and/or wheat middlings.

Wet-Cake, Distillers Dried Grains (DDG) and Distillers Dried Grain Solubles (DDGS)

Wet-cake, Distillers Dried Grains and Distillers Dried Grains with Solubles are products obtained after the removal of ethyl alcohol by distillation from yeast fermentation of a grain or a grain mixture by methods employed in the grain distilling industry.

Stillage coming from the distillation (e.g. comprising water, remainings of the grain, yeast cells etc.) is separated into a "solid" part and a liquid part.

The solid part is called "wet-cake" and can be used as animal feed as such.

The liquid part is (partially) evaporated into a syrup (solubles).

When the wet-cake is dried it is Distillers Dried Grains (DDG).

When the wet-cake is dried together with the syrup (solubles) it is Distillers Dried Grans with Solubles (DDGS).

Wet-cake may be used in dairy operations and beef cattle feedlots.

The dried DDGS may be used in livestock, e.g. dairy, beef and swine) feeds and poultry feeds.

Corn DDGS is a very good protein source for dairy cows.

Corn Gluten Meal

In one aspect, the by-product of corn may be corn gluten meal (CGM).

CGM is a powdery by-product of the corn milling industry. CGM has utility in, for example, animal feed. It can be used as an inexpensive protein source for feed such as pet food, livestock feed and poultry feed. It is an especially good source of the amino acid cysteine, but must be balanced with other proteins for lysine.

Feed Additive Composition

The feed additive composition of the present invention and/or the feedstuff comprising same may be used in any suitable form.

The feed additive composition of the present invention may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

In some applications, the feed additive compositions of the present invention may be mixed with feed or administered in the drinking water.

In one aspect the present invention relates to a method of preparing a feed additive composition, comprising admixing a xylanase as taught herein with a feed acceptable carrier, diluent or excipient, and (optionally) packaging.

Premix

The feedstuff and/or feed additive composition may be combined with at least one mineral and/or at least one vitamin. The compositions thus derived may be referred to herein as a premix.

Malting and Brewing

The synthetic xylanase (or composition comprising the synthetic xylanase) of the present invention may be used in malting and brewing.

Barley grains contain 1.7 to 4.1% (w/w) water-extractable and 3.6 to 6.4% (w/w) total beta-glucan (Anderson, M. A., Cook, J. A., & Stone, B. A., Journal of the Institute of Brewing, 1978, 84, 233-239; Henry, J., Journal of the Science of Food and Agriculture, 1985, 36, 1243).

Wheat grains contain 0.1 to 0.8% (w/w) water-extractable and 0.6 to 1.4% (w/w) total beta-glucan (Anderson, M. A. et al (1978) supra).

Efficient hydrolysis of arabinoxylans (AXsol) and beta-glucan is important because such compounds can be involved in production problems such as wort viscosity (Ducroo, P. & Frelon, P. G., Proceedings of the European Brewery Convention Congress, Zurich, 1989, 445; Vietor, R. J. & Voragen, A. G. J., Journal of the Institute of Brewing, 1993, 99, 243) and filterability and haze formation (Coote, N. & Kirsop, B. H. 1976, Journal of the Institute of Brewing, 1976, 82, 34; Izawa, M., Kano, Y. & Kanimura, M. 1991. Proceedings Aviemore Conference on Malting, brewing and Distillling, 1990, 427).

The present invention provides a method of hydrolysing arabinoxylans (e.g. AXinsol and AXsol) during malting and brewing wherein wheat grains, barley grains or a combination thereof, or portions of the wheat and/or barley grains, are admixed with the synthetic xylanase of the present invention.

In one aspect of the present invention may relate to a food composition that is a beverage, including, but not limited to, a fermented beverage such as beer and wine, comprising a synthetic xylanase according to the present invention.

In another aspect of the present invention may relate to a food composition that is a beverage, including, but not limited to, a fermented beverage such as beer and wine, comprising a synthetic xylanase according to the present invention.

In the context of the present invention, the term "fermented beverage" is meant to comprise any beverage produced by a method comprising a fermentation process, such as a microbial fermentation, such as a bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, corn (maize), potato, tapioca, cassava and syrups, such as corn syrup, sugar cane syrup, inverted sugar syrup, barley and/or wheat syrups, and the like may be used as a source of starch.

As used herein, the term "mash" (e.g. as used herein in relation to malting or brewing) refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing a fermented beverage such as beer comprising mixing the synthetic xylanase of the present invention with malt or adjunct.

Examples of beers comprise: full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavoured malt beverages, e. g. citrus flavoured, such as lemon-, orange-, lime-, or berry-flavoured malt beverages, liquor flavoured malt beverages, e. g., vodka-, rum-, or tequila-flavoured malt liquor, or coffee flavoured malt beverages, such as caffeine-flavoured malt liquor, and the like.

Breakdown of Grain-Based Material e.g. for Biofuel Production

The synthetic enzyme (or composition comprising the synthetic enzyme) of the present invention or as disclosed herein may be used to breakdown (degrade) AXinsol and AXsol during grain processing from e.g. grain-based material. The grain-based material may be whole grains (e.g. whole wheat, barley, rye, triticale or corn grains or mixtures thereof) or portions of the whole grains, or mixtures thereof.

In one embodiment the synthetic enzyme (or composition comprising the synthetic enzyme) of the present invention or as disclosed herein may be used to breakdown (degrade) AXinsol and AXsol in grain-based materials or whole grains.

For the avoidance of doubt the whole grains can be mechanically broken.

The grain-based material may be broken down or degraded to glucose. The glucose may subsequently be used as a feedstock for any fermentation process, e.g. for biofuel (e.g. bioethanol) production and/or biochemicals (e.g., bio-based isoprene) production.

The grain-based material may be feedstock for a biofuel (e.g. bioethanol) production process.

Today most fuel ethanol is produced from corn (maize) grain, which is milled, treated with amylase enzymes to hydrolyse starch to sugars, fermented, and distilled. While substantial progress has been made in reducing costs of ethanol production, substantial challenges remain. Improved techniques are still needed to reduce the cost of biofuel feedstocks for ethanol production. For example, in grain-based ethanol production degradation of arabinoxylans may increase accessibility of starch.

The present invention provides a synthetic xylanase for use in the breakdown of hemicelluloses, e.g. arabinoxylan— particularly AXinsol and AXsol.

By way of example only, in the European fuel alcohol industry, small grains like wheat, barley and rye are common raw materials, in the US corn is mainly used. Wheat, barley and rye contain, next to starch, high levels of non-starch polysaccharide polymers (NSP), like cellulose, beta-glucan and hemicellulose.

The ratio in which the different NSPs are represented differ for each feedstock. The table below shows the different amounts of NSPs in wheat, barley and rye compared to some other feedstocks.

TABLE 1

Non-starch Polysaccharides (NSPs) present in different feedstocks (g kg$^{-1}$ dry matter)

|  | Corn | Wheat | Rye | Barley | | Oats | |
|---|---|---|---|---|---|---|---|
|  |  |  |  | Hulled | Hulless | Hulled | Hulless |
| Beta-Glucan | 1 | 8 | 16 | 42 | 42 | 28 | 41 |
| Cellulose | 22 | 17-20 | 15-16 | 43 | 10 | 82 | 14 |
| Soluble and Non-soluble NCP[1] | 75 | 89-99 | 116-136 | 144 | 114 | 150 | 113 |
| Total NSP | 97 | 107-119 | 132-152 | 186 | 124 | 232 | 116 |

[1]Non Cellulosic Polysaccharides: pentosans, (arabino)xylans and other hemicelluloses NSPs can give high viscosity to grain mashes. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step.

In one embodiment of the present invention the method for degrading grain-based material comprises admixing the synthetic xylanase as disclosed herein as early as possible in the biofuel (e.g. bioethanol) production process, e.g. preferably during mixing of the grain-based material at the start of the process. One advantage of adding the modified xylanases as disclosed herein at an early stage in the process is that the enzymes breakdown initial viscosity.

In one embodiment of the present invention the method for degrading grain-based material comprises admixing the synthetic xylanase as disclosed herein prior to or during liquefaction, saccharification, fermentation, simultaneous saccharification and fermentation, post fermentation or a combination thereof.

In one embodiment of the present invention the method for degrading grain-based material comprises admixing the synthetic xylanase as disclosed herein during liquefaction (e.g. a high temperature step that follows mixing).

Therefore in one embodiment the present invention relates to reducing viscosity when degrading grain-based materials, e.g. in biofuel (e.g. bioethanol) production processes.

The benefits of using the synthetic xylanases taught herein to reduce viscosity when degrading grain-based materials, e.g. in biofuel (e.g. bioethanol) production processes are multiple:

Higher dry substance mash can be used in the process
Higher solids content of final syrup can be obtained
Better heat transfer, lower energy requirement
Reduced evaporator fouling leading to reduced cleaning costs
Increased final ethanol yields
Improved quality of DDGS (by-product)
Better separation between the solid and liquid part during stillage separation (after distillation). The lower viscosity increases separation efficiency.

A further significant advantage of the present invention is that use of the synthetic xylanase described herein in biofuel production can also result in improved (by)products from that process such as wet-cake, Distillers Dried Grains (DDG) or Distillers Dried Grains with Solubles (DDGS). Therefore one advantage of the present invention is since the wet-cake, DDG and DDGS are (by)products of biofuel (e.g. bioethanol) production the use of the present invention can result is improved quality of these (by)products. For example the arabinoxylans in the (by)products can be already dissolved during the biofuel production process.

Cereal (e.g. Wheat) Gluten-Starch Separation

The synthetic xylanase (or composition comprising the synthetic xylanase) of the present invention or as disclosed herein may be used to breakdown (degrade) AXinsol and AXsol during wheat starch and gluten separation.

After initial separation of the wheat bran and germ from the endosperm, fractionation of wheat endosperm flour into starch and gluten fractions is industrially applied on large scale to obtain high quality A-starch and byproducts B-starch and vital gluten.

The product of the degradation of the cereal flour (e.g. wheat flour) in the present invention is starch (high quality A-starch).

In addition, by-products B-starch and vital gluten are also produced. Each individual product is then further processed to supplement or modify food product characteristics to the market needs.

There are several wheat separation processes used by industry described in literature. These industrial processes differ mainly in the forms of the flour-water mixtures presented to the fractionation equipment (centrifuge, hydrocyclone, or screen) or in the initial reaction conditions as temperature and applying of shear (Abdulvahit Sayaslan, Lebensm.-Wiss. U.-Technol 37 (2004) 499-515, *Wetmilling of wheat flour: industrial processes and small-sacale test methods*).

In the method for separating a cereal flour (e.g. wheat flour) into starch and gluten fractions the method comprises admixing a cereal flour (e.g. wheat flour), water and a synthetic xylanase. The cereal flour, water and synthetic xylanase may be mixed simultaneously or sequentially. In some embodiments the cereal flour (e.g. wheat flour) and water may be admixed before admixing with the synthetic xylanase.

In general, cereal flour (e.g. wheat flour) is either mixed to a dough or batter, varying between 35 to 63% Dry solids, at temperatures of -20-45° C. The mixture is then further processed either by:

1) letting the mixture rest for some time (-30 minutes) and sequentially washing out the starch from the mixture using a screen, centrifuge or hydrocyclone to separate the starch milk from the gluten, or
2) applying shear to the mixture, optionally diluting the mixture further and then separating the wheat flour by a hydrocyclone, or a 2- or 3-phase decanter centrifuge.

The term "dry solids" as used herein means total solids (dissolved and undissolved) of a slurry (in %) on a dry weight basis.

In one embodiment of the present invention the method or use as claimed may include the steps of mixing wheat flour to form a dough or batter between 35-63% dry solids, at a temperature of about 20 to about 45° C. and separating the starch from the gluten.

The method of the present invention may further comprise:

a) resting the mixture for about 30 minutes and sequentially washing out the starch from the mixture using either a screen, a centrifuge or a hydrocyclone to separate the starch milk from the gluten; or
b) applying shear to the mixture and optionally diluting the mixture further, separating the starch from the gluten using a hydrocyclone or a 2- or 3-phase decanter centrifuge.

The present invention provides for improving the separation of the starch and the gluten by adding a synthetic xylanase as taught herein suitably during the initial mixing step of flour and water in the various processes described above used for wheat starch separation. Separation is improved by adding a synthetic xylanase during the initial mixing step due to viscosity reduction and the hydrolysis of AXsol and/or AXinsol interfering with the gluten particles. By degrading these poly- and oligosaccharides, gluten agglomeration is enhanced, improving the gluten yield. (S. A. Frederix, C. M. Courtin, J. A. Delcour, J. *Cereal Sci.* 40 (2004) 41-49, *Substrate selectivity and inhibitor sensitivity affect xylanase functionality in wheat flour gluten-starch separation*).

One advantage of the present invention is that it results in higher A-starch yields and/or better quality gluten (e.g. better quality vital gluten).

One advantage of the present invention is that it improves wheat gluten-starch separation.

One of the ways to evaluate gluten quality is by monitoring gluten agglomeration. When a certain amount of friction through kneading of the dough or mixing of the batter is applied, gluten particles tend to agglomerate into larger particles that form a polymeric network, called "vital gluten". "Vital gluten" can be added to food products to improve properties of baked goods such as dough strength, shelf-life and bread volume (L. Day, M. A. Augustin, I. L. Batey and C. W. Wrigley; *Wheat-gluten uses and industry needs*; Trends in Food Science & Technology 17 (2006) 82-90).

In the bakery industry, the quality and quantity of the gluten in a wheat flour is determined by the ICC standard assay No. 155 (AACC 38-12) using a Glutomatic. In this device, a dough is formed from wheat flour (10.0 gr) mixed with a small amount of 2% NaCl solution (4.2-4.8 ml). After 20 seconds of mixing step, the dough is continuously kneaded while being washed for 5 minutes with a 2% NaCl solution at room temperature (-22° C.) pumped through the mixing cup at a flow rate of -70 ml/minute. During this washing step, the wash water containing starch is collected and the gluten particles form a gluten ball within the Glutomatic sieve holder.

The quality of the gluten is measured by evaluating the gluten agglomeration. This is done by centrifuging the gluten ball in a special centrifuge containing a small sieve. The gluten particles that pass this sieve are weighed (small gluten) and the total amount of gluten is weighed. The gluten index is calculated by (total wet gluten—small wet gluten)/total wet gluten. The more gluten agglomeration is improved, the smaller the small gluten fraction will be and the higher the gluten index value is. A high gluten index, with a theoretical maximum of 100%, indicates a high quality gluten ball.

Another value to quantify the amount of gluten is the dried gluten yield (%). This value is calculated by dividing the grams of total dried gluten by the total amount of dry flour which was used in the experiment. The more dried gluten is recovered, the better the separation is. This industrial assay is currently under adaptation to simulate a dough separation process used in industry.

Dosages

Preferably, the synthetic xylanase is present in the xylan-containing material (e.g. feedstuff) in the range of about 500 XU/kg to about 16,000 XU/kg xylan-containing material (e.g. feed), more preferably about 750 XU/kg feed to about 8000 XU/kg xylan-containing material (e.g. feed), preferably about 1500 XU/kg feed to about 3000 XU/kg xylan-containing material (e.g. feed), preferably about 2000 XU/kg feed to about 2500 XU/kg xylan-containing material (e.g. feed), and even more preferably about 1000 XU/kg xylan-containing material (e.g. feed) to about 4000 XU/kg xylan-containing material (e.g. feed).

In one embodiment the synthetic xylanase is present in the xylan-containing material (e.g. feedstuff) at more than about 500 XU/kg xylan-containing material (e.g. feed), suitably more than about 600 XU/kg xylan-containing material (e.g. feed), suitably more than about 700 XU/kg xylan-containing material (e.g. feed), suitably more than about 800 XU/kg xylan-containing material (e.g. feed), suitably more than about 900 XU/kg xylan-containing material (e.g. feed), suitably more than about 1000 XU/kg xylan-containing material (e.g. feed), suitably more than about 2000 XU/kg, suitably more than about 2500 XU/kg, suitably more than about 3000 XU/kg xylan-containing material (e.g. feed), In one embodiment the synthetic xylanase is present in the xylan-containing material (e.g. feedstuff) at a concentration of between about 2000 XU/kg to about 2500 XU/kg.

In one embodiment the synthetic xylanase is present in the xylan-containing material (e.g. feedstuff) at less than about 16,000 XU/kg xylan-containing material (e.g. feed), suitably less than about 8000 XU/kg xylan-containing material (e.g. feed), suitably less than about 7000 XU/kg xylan-containing material (e.g. feed), suitably less than about 6000 XU/kg xylan-containing material (e.g. feed), suitably less than about 5000 XU/kg xylan-containing material (e.g. feed), suitably less than about 4000 XU/kg xylan-containing material (e.g. feed).

Preferably, the synthetic xylanase may be present in a feed additive composition in range of about 100XU/g to about 320,000XU/g composition, more preferably about 300XU/g composition to about 160,000XU/g composition, and even more preferably about 500XU/g composition to about 50,000 XU/g composition, and even more preferably about 500XU/g composition to about 40,000 XU/g composition.

In one embodiment the synthetic xylanase is present in the feed additive composition at more than about 100XU/g composition, suitably more than about 200XU/g composition, suitably more than about 300XU/g composition, suitably more than about 400XU/g composition, suitably more than about 500XU/g composition.

In one embodiment the synthetic xylanase is present in the feed additive composition at less than about 320,000XU/g composition, suitably less than about 160,000XU/g composition, suitably less than about 50,000XU/g composition, suitably less than about 40,000XU/g composition, suitably less than about 30000XU/g composition.

The xylanase activity can be expressed in xylanase units (XU) measured at pH 5.0 with AZCL-arabinoxylan (azurine-crosslinked wheat arabinoxylan, Xylazyme tablets, Megazyme) as substrate. Hydrolysis by endo-(1-4)-β-D-xylanase (xylanase) produces water soluble dyed fragments, and the rate of release of these (increase in absorbance at 590 nm) can be related directly to enzyme activity. The xylanase units (XU) are determined relatively to an enzyme standard (Danisco Xylanase, available from Danisco Animal Nutrition) at standard reaction conditions, which are 40° C., 5 min reaction time in McIlvaine buffer, pH 5.0.

The xylanase activity of the standard enzyme is determined as amount of released reducing sugar end groups from an oat-spelt-xylan substrate per min at pH 5.3 and 50° C. The reducing sugar end groups react with 3, 5-Dinitrosalicylic acid and formation of the reaction product can be measured as increase in absorbance at 540 nm. The enzyme activity is quantified relative to a xylose standard curve (reducing sugar equivalents). One xylanase unit (XU) is the amount of standard enzyme that releases 0.5 μmol of reducing sugar equivalents per min at pH 5.3 and 50° C.

In one embodiment suitably the enzyme is classified using the E.C. classification above, and the E.C. classification designates an enzyme having that activity when tested in the assay taught herein for determining 1 XU.

Preferably, the synthetic xylanase is present in the mixing step of a wheat starch separation process in the dough or batter in the range of about 0.01 kg/MT DS dough or batter to about 0.60 kg/MT DS, more preferably about 0.05 kg/MT DS to about 0.45 kg/MT DS dough or batter, and even more preferably about 0.10 kg/MT DS to about 0.25 kg/MT DS dough or batter.

In some embodiments (particularly in the wheat starch separation embodiment) the synthetic xylanase may be dosed in the range of about 0.019 g protein/MT DS wheat flour (which is equivalent to 0.019 mg/kg DS) to about 119 g protein/MT DS wheat flour (which is equivalent to 119 mg/kg DS—where DS means dry solids content and MT means metric ton.

In some embodiments (particularly in the wheat starch separation embodiment) the synthetic xylanase may be dosed at about 1.19 g protein/MT DS wheat flour (which is equivalent to about 1.19 mg/kg DS)—where DS means dry solids content and MT means metric ton.

In some embodiments (particularly in the wheat starch separation embodiment) the synthetic xylanase may be dosed in the range of about 9 to about 120000 units/kg wheat flour, suitably between about 500-2400 units/kg wheat flour, suitably between about 900-1200 units/kg wheat flour (wherein 1 unit is defined as the amount of enzyme required to generate 1 micromole of xylose reducing sugar equivalents per minute under the conditions of the birch wood assay taught below:

Birch Wood Assay

Xylanase activity of an enzyme can be measured using 1% xylan from birch wood (Sigma 95588) or 1% arabinoxylan from wheat flour (MEGAZYME® P-WAXYM) as substrates. The assay is performed in 50 mM sodium citrate pH 5.3, 0.005% Tween-80 buffer at 50° C. for 10 minutes.

The released reducing sugar is quantified by reaction with 3, 5-Dinitrosalicylic acid and measurement of absorbance at 540 nm. The enzyme activity is quantified relative to a xylose standard curve. In this assay, one xylanase unit (U) is defined as the amount of enzyme required to generate 1 micromole of xylose reducing sugar equivalents per minute under the conditions of the assay.

In some embodiments (particularly in degrading grain-based material) the synthetic xylanase may be dosed in the range of about 0.29 g/protein/MT DS wheat (which is equivalent to 0.29 mg/kg DS) to about 0290 g/protein/MT DS wheat (which is equivalent to 290 mg/kg DS).

In some embodiments (particularly in degrading grain-based material) the xylanase may be dosed at 2.9 g/protein/MT DS wheat (which is equivalent to 2.9 mg/kg DS).

In some embodiments (particularly in degrading grain-based material) the xylanase may be dosed in the range of about 22 to about 285000 units/kg, suitably about 1100 to about 5700 units/kg, suitably about 2200 to about 2850 units/kg (wherein 1 unit is defined as the amount of enzyme required to generate 1 micromole of xylose reducing sugar equivalents per minute under the conditions of the birch wood assay taught above.

The synthetic enzyme and/or composition comprising the synthetic enzyme according to the present invention may be designed for one-time dosing or may be designed for use (e.g. feeding) on a daily basis.

The optimum amount of the synthetic enzyme and/or composition comprising the synthetic enzyme to be used in the present invention will depend on the product to be treated and/or the method of contacting the product with the composition and/or the intended use for the same.

The amount of synthetic enzyme used in the compositions should be a sufficient amount to be effective.

The amount of synthetic enzyme used in the compositions should be a sufficient amount to be effective and to remain sufficiently effective in for example improving the performance of an animal fed feed products containing said composition. This length of time for effectiveness should extend up to at least the time of utilisation of the product (e.g. feed additive composition or feed containing same).

Formulation

In one embodiment the synthetic enzyme may be formulated as a liquid, a dry powder or a granule.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

For some embodiments the synthetic enzyme may be coated, for example encapsulated.

In one embodiment the coating protects the synthetic xylanase from heat and may be considered a thermoprotectant.

In one embodiment the feed additive composition is formulated to a dry powder or granules as described in WO2007/044968 (referred to as TPT granules) or WO1997/016076 or WO1992/012645 (each of which is incorporated herein by reference).

In one embodiment the feed additive composition may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

With regard to the granule at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

In one embodiment the feed additive composition may be formulated to a granule for animal feed comprising: a core; an active agent, the active agent of the granule retaining at least 80% activity after storage and after a steam-heated pelleting process where the granule is an ingredient; a moisture barrier coating; and a moisture hydrating coating that is at least 25% w/w of the granule, the granule having a water activity of less than 0.5 prior to the steam-heated pelleting process.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

The granule may be produced using a steam-heated pelleting process which may be conducted between 85° C. and 95° C. for up to several minutes.

In some embodiments the enzyme may be diluted using a diluent, such as starch powder, lime stone or the like.

In one embodiment, the synthetic enzyme or composition comprising the synthetic enzyme is in a liquid formulation suitable for consumption preferably such liquid consumption contains one or more of the following: a buffer, salt, sorbitol and/or glycerol.

In another embodiment the synthetic enzyme or composition comprising the synthetic enzyme may be formulated by applying, e.g. spraying, the enzyme(s) onto a carrier substrate, such as ground wheat for example.

In one embodiment the synthetic enzyme or composition comprising the synthetic enzyme according to the present invention may be formulated as a premix. By way of example only the premix may comprise one or more feed components, such as one or more minerals and/or one or more vitamins.

In one embodiment the synthetic enzyme for use in the present invention are formulated with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Packaging

In one embodiment the synthetic enzyme and/or composition comprising same (e.g. feed additive composition) and/or premix and/or feed or feedstuff according to the present invention is packaged.

In one preferred embodiment the feed additive composition and/or premix and/or feed or feedstuff is packaged in a bag, such as a paper bag.

In an alternative embodiment the feed additive composition and/or premix and/or feed or feedstuff may be sealed in a container. Any suitable container may be used.

Forms

The synthetic enzyme or composition comprising the synthetic enzyme (e.g. the feed additive composition) of the present invention and other components and/or the feedstuff comprising same may be used in any suitable form.

The synthetic enzyme or composition comprising same (e.g. feed additive composition) of the present invention may be used in the form of solid or liquid preparations or alternatives thereof. Examples of solid preparations include powders, pastes, boluses, capsules, pellets, tablets, pills, capsules, ovules, solutions or suspensions, dusts, and granules which may be wettable, spray-dried or freeze-dried. Examples of liquid preparations include, but are not limited to, aqueous, organic or aqueous-organic solutions, suspensions and emulsions.

The composition comprising the synthetic enzyme may contain flavouring or colouring agents, for immediate-, delayed-, modified-, sustained-, pulsed- or controlled-release applications.

By way of example, if the composition of the present invention is used in a solid, e.g. pelleted form, it may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

Subject

The term "subject", as used herein, means an animal that is to be or has been administered with a synthetic xylanase according to the present invention or a feed additive composition according to the present invention or a feedstuff comprising said feed additive composition according to the present invention.

The term "subject", as used herein, means an animal.

In one embodiment, the subject is a mammal, bird, fish or crustacean including for example livestock or a domesticated animal (e.g. a pet).

In one embodiment the "subject" is livestock.

The term "livestock", as used herein refers to any farmed animal. Preferably, livestock is one or more of ruminants such as cattle (e.g. cows or bulls (including calves)), monogastric animals such as poultry (including broilers, chickens and turkeys), pigs (including piglets), birds, aquatic animals such as fish, agastric fish, gastric fish, freshwater fish such as salmon, cod, trout and carp, e.g. koi carp, marine fish such as sea bass, and crustaceans such as shrimps, mussels and scallops), horses (including race horses), sheep (including lambs).

In another embodiment the "subject" is a domesticated animal or pet or an animal maintained in a zoological environment.

The term "domesticated animal or pet or animal maintained in a zoological environment" as used herein refers to any relevant animal including canines (e.g. dogs), felines (e.g. cats), rodents (e.g. guinea pigs, rats, mice), birds, fish (including freshwater fish and marine fish), and horses.

Performance

As used herein, "animal performance" may be determined by the feed efficiency and/or weight gain of the animal and/or by the feed conversion ratio and/or by the digestibility of a nutrient in a feed (e.g. amino acid digestibility) and/or digestible energy or metabolizable energy in a feed and/or by nitrogen retention and/or by animals ability to avoid the negative effects of necrotic enteritis and/or by the immune response of the subject.

Preferably "animal performance" is determined by feed efficiency and/or weight gain of the animal and/or by the feed conversion ratio.

By "improved animal performance" it is meant that there is increased feed efficiency, and/or increased weight gain and/or reduced feed conversion ratio and/or improved digestibility of nutrients or energy in a feed and/or by improved nitrogen retention and/or by an improved immune response in the subject resulting from the use of feed additive composition of the present invention in feed in comparison to feed which does not comprise said feed additive composition.

Preferably, by "improved animal performance" it is meant that there is increased feed efficiency and/or increased weight gain and/or reduced feed conversion ratio.

As used herein, the term "feed efficiency" refers to the amount of weight gain per unit of feed when the animal is fed ad-libitum or a specified amount of feed during a period of time.

By "increased feed efficiency" it is meant that the use of a feed additive composition according the present invention in feed results in an increased weight gain per unit of feed intake compared with an animal fed without said feed additive composition being present.

Feed Conversion Ratio (FCR)

As used herein, the term "feed conversion ratio" refers to the amount of feed fed to an animal to increase the weight of the animal by a specified amount.

An improved feed conversion ratio means a lower feed conversion ratio.

By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Nutrient Digestibility

Nutrient digestibility as used herein means the fraction of a nutrient that disappears from the gastro-intestinal tract or a specified segment of the gastro-intestinal tract, e.g. the small intestine. Nutrient digestibility may be measured as the difference between what is administered to the subject and what comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastrointestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed.

Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Combination with Other Components

The synthetic xylanase of the present invention may be used in combination with other components.

In one embodiment the synthetic xylanase of the present invention may be used in combination with a probiotic or a direct fed microbial (DFM), e.g. a direct fed bacteria.

The combination of the present invention comprises the synthetic xylanase of the present invention or a composition comprising the synthetic xylanase, e.g. a feed additive composition, and another component which is suitable for human or animal consumption and is capable of providing a medical or physiological benefit to the consumer.

In one embodiment the "another component" may be one or more further enzymes (e.g. further feed enzymes or brewing or malting enzymes, or grain processing enzymes or wheat gluten-starch separation enzymes).

Suitable additional enzymes for use in the present invention may be one or more of the enzymes selected from the group consisting of: endoglucanases (E.C. 3.2.1.4); cellio-biohydrolases (E.C. 3.2.1.91), β-glucosidases (E.C. 3.2.1.21), cellulases (E.C. 3.2.1.74), lichenases (E.C. 3.2.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), amylases, alpha-amylases (E.C. 3.2.1.1), other xylanases (E.C. 3.2.1.8, E.C. 3.2.1.32, E.C. 3.2.1.37, E.C. 3.2.1.72, E.C. 3.2.1.136), glucoamylases (E.C. 3.2.1.3), hemicellulases, proteases (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)), debranching enzymes, cutinases, esterases and/or mannanases (e.g. a β-mannanase (E.C. 3.2.1.78)).

In one embodiment (particularly for feed applications) the other component may be one or more of the enzymes selected from the group consisting of an amylase (including α-amylases (E.C. 3.2.1.1), G4-forming amylases (E.C. 3.2.1.60), β-amylases (E.C. 3.2.1.2) and γ-amylases (E.C. 3.2.1.3)); and/or a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or a phytase (e.g. a 6-phytase (E.C.3.1.3.26) or a 3-phytase (E.C. 3.1.38)).

In one embodiment (particularly for feed applications) the other component may be a combination of an amylase (e.g. α-amylases (E.C. 3.2.1.1)) and a protease (e.g. subtilisin (E.C. 3.4.21.62)).

In one embodiment (particularly for feed applications) the other component may be a 3-glucanase, e.g. an endo-1,3(4)-β-glucanases (E.C. 3.2.1.6).

In one embodiment (particularly for feed applications) the other component may be a phytase (e.g. a 6-phytase (E.C.3.1.3.26) or a 3-phytase (E.C. 3.1.38).

In one embodiment (particularly for feed applications) the other component may be a mannanases (e.g. a β-mannanase (E.C. 3.2.1.78)).

In one embodiment (particularly for feed applications) the other component may be a lipase lipase (E.C. 3.1.1.3), a lipid acyltransferase (generally classified as E.C. 2.3.1.x), or a phospholipase (E.C. 3.1.1.4, E.C. 3.1.1.32 or E.C. 3.1.1.5), suitably a lipase (E.C. 3.1.1.3).

In one embodiment (particularly for feed applications) the other component may be a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

In one embodiment the additional component may be a stabiliser or an emulsifier or a binder or carrier or an excipient or a diluent or a disintegrant.

The term "stabiliser" as used here is defined as an ingredient or combination of ingredients that keeps a product (e.g. a feed product) from changing over time.

The term "emulsifier" as used herein refers to an ingredient (e.g. a feed ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers.

As used herein the term "binder" refers to an ingredient (e.g. a feed ingredient) that binds the product together through a physical or chemical reaction. During "gelation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others. Examples of granulation binders include one or more of: polyvinylpyrrolidone, hydroxypropylmethylcellulose (HPMC), hydroxypropylcellulose (HPC), sucrose, maltose, gelatin and acacia.

"Carriers" mean materials suitable for administration of the enzyme and include any such material known in the art such as, for example, any liquid, gel, solvent, liquid diluent, solubilizer, or the like, which is non-toxic and which does not interact with any components of the composition in a deleterious manner.

The present invention provides a method for preparing a composition (e.g. a feed additive composition) comprising admixing an enzyme of the present invention with at least one physiologically acceptable carrier selected from at least one of maltodextrin, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

Examples of "excipients" include one or more of: microcrystalline cellulose and other celluloses, lactose, sodium citrate, calcium carbonate, dibasic calcium phosphate, glycine, starch, milk sugar and high molecular weight polyethylene glycols.

Examples of "disintegrants" include one or more of: starch (preferably corn, potato or tapioca starch), sodium starch glycollate, croscarmellose sodium and certain complex silicates.

Examples of "diluents" include one or more of: water, ethanol, propylene glycol and glycerin, and combinations thereof.

The other components may be used simultaneously (e.g. when they are in admixture together or even when they are delivered by different routes) or sequentially (e.g. they may be delivered by different routes) to the xylanase of the present invention.

Preferably, when the feed additive composition of the present invention is admixed with another component(s), the DFM remains viable.

In one embodiment preferably the feed additive composition according to the present invention does not comprise chromium or organic chromium In one embodiment preferably the feed additive according to the present invention does not contain glucanase.

In one embodiment preferably the feed additive according to the present invention does not contain sorbic acid.

Isolated

In one aspect, preferably the amino acid sequence, or nucleic acid, or enzyme according to the present invention is in an isolated form. The term "isolated" means that the sequence or enzyme or nucleic acid is at least substantially free from at least one other component with which the sequence, enzyme or nucleic acid is naturally associated in nature and as found in nature. The sequence, enzyme or nucleic acid of the present invention may be provided in a form that is substantially free of one or more contaminants with which the substance might otherwise be associated. Thus, for example it may be substantially free of one or more potentially contaminating polypeptides and/or nucleic acid molecules.

Purified

In one aspect, preferably the sequence, enzyme or nucleic acid according to the present invention is in a purified form. The term "purified" means that the given component is present at a high level. The component is desirably the predominant component present in a composition. Preferably, it is present at a level of at least about 90%, or at least about 95% or at least about 98%, said level being determined on a dry weight/dry weight basis with respect to the total composition under consideration.

Nucleotide Sequence

The scope of the present invention encompasses nucleotide sequences encoding proteins having the specific properties as defined herein.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In one embodiment the term "nucleotide sequence" means cDNA.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e. arabinoxylan), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, in some embodiments a homologous sequence is taken to include an amino acid or a nucleotide sequence which may be at least 97.7% identical, preferably at least 98 or 99% identical to the subject sequence.

In some embodiments a homologous sequence is taken to include an amino acid or a nucleotide sequence which may be at least 85% identical, preferably at least 90 or 95% identical to the subject sequence.

Typically, the homologues will comprise the same active sites etc. as the subject amino acid sequence for instance. Although homology can also be considered in terms of similarity (i.e. amino acid residues having similar chemical properties/functions), in the context of the present invention it is preferred to express homology in terms of sequence identity.

In one embodiment, a homologous sequence is taken to include an amino acid sequence or nucleotide sequence which has one or several additions, deletions and/or substitutions compared with the subject sequence.

In the present context, "the subject sequence" relates to the nucleotide sequence or polypeptide/amino acid sequence according to the invention.

Preferably, the % sequence identity with regard to a polypeptide sequence is determined using SEQ ID No. 1 as the subject sequence in a sequence alignment. In one embodiment, the polypeptide subject sequence is selected from the group consisting of SEQ ID No. 1, SEQ ID No. 3, SEQ ID No. 5, SEQ ID No. 7, SEQ ID No 9 or SEQ ID No. 11.

Preferably, the % sequence identity with regard to a nucleotide sequence is determined using SEQ ID No. 2 as the subject sequence in the sequence alignment. In one embodiment, the subject sequence for nucleotide sequences may be selected from the group consisting of SEQ ID No. 2, SEQ ID No. 4, SEQ ID No. 6, SEQ ID No. 8, SEQ ID No. 10 or SEQ ID No. 12.

A "parent nucleic acid" or "parent amino acid" means a nucleic acid sequence or amino acid sequence, encoding or coding for the parent polypeptide, respectively.

In one embodiment the present invention relates to a protein whose amino acid sequence is represented herein or a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids, preferably over at least 100 contiguous amino acids, preferably over at least 200 contiguous amino acids.

In one embodiment the present invention relates to a nucleic acid sequence (or gene) encoding a protein whose amino acid sequence is represented herein or encoding a protein derived from this (parent) protein by substitution, deletion or addition of one or several amino acids, such as 2, 3, 4, 5, 6, 7, 8, 9 amino acids, or more amino acids, such as 10 or more than 10 amino acids in the amino acid sequence of the parent protein and having the activity of the parent protein.

In the present context, in one embodiment a homologous sequence or foreign sequence is taken to include a nucleotide sequence which may be at least 97.7% identical, preferably at least 98 or 99% identical to a nucleotide sequence encoding a polypeptide of the present invention (the subject sequence).

In another embodiment, a homologous sequence is taken to include a nucleotide sequence which may be at least 85% identical, preferably at least 90 or 95% identical to a nucleotide sequence encoding a polypeptide of the present invention (the subject sequence).

Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology or % identity between two or more sequences.

% homology or % identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology or % identity when a global alignment is performed.

Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology or % identity therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatiana@ncbi.nlm.nih.gov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60), such as for example in the GenomeQuest search tool (www.genomequest.com).

Although the final % homology or % identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST | |
|---|---|
| GAP OPEN | 9 |
| GAP EXTENSION | 2 |

| FOR CLUSTAL | DNA | PROTEIN |
|---|---|---|
| Weight Matrix | IUB | Gonnet 250 |
| GAP OPENING | 15 | 10 |
| GAP EXTEND | 6.66 | 0.1 |

In one embodiment, CLUSTAL may be used with the gap penalty and gap extension set as defined above.

Suitably, the degree of identity with regard to a nucleotide sequence or protein sequence is determined over at least 20 contiguous nucleotides/amino acids, preferably over at least 30 contiguous nucleotides/amino acids, preferably over at least 40 contiguous nucleotides/amino acids, preferably over at least 50 contiguous nucleotides/amino acids, preferably over at least 60 contiguous nucleotides/amino acids, preferably over at least 100 contiguous nucleotides/amino acids.

Suitably, the degree of identity with regard to a nucleotide sequence is determined over at least 100 contiguous nucleotides, preferably over at least 200 contiguous nucleotides, preferably over at least 300 contiguous nucleotides, preferably over at least 400 contiguous nucleotides, preferably over at least 500 contiguous nucleotides, preferably over at least 600 contiguous nucleotides, preferably over at least 700 contiguous nucleotides, preferably over at least 800 contiguous nucleotides.

Suitably, the degree of identity with regard to a nucleotide sequence may be determined over the whole sequence taught herein.

Suitably, the degree of identity with regard to a nucleotide sequence may be determined over the whole sequence taught herein as e.g. SEQ ID No. 2 or SEQ ID No. 4 or SEQ ID No. 6 or SEQ ID No. 8 or SEQ ID No. 10 or SEQ ID No. 12. Suitably, the degree of identity with regard to a nucleotide sequence may be determined over the whole sequence as taught herein as SEQ ID No. 2.

Suitably, the degree of identity with regard to a protein (amino acid) sequence is determined over at least 100 contiguous amino acids, preferably over at least 200 contiguous amino acids, preferably over at least 300 contiguous amino acids.

Suitably, the degree of identity with regard to an amino acid or protein sequence may be determined over the whole sequence taught herein.

Suitably, the degree of identity with regard to an amino acid or protein sequence may be determined over the whole sequence taught herein as the mature sequence, e.g. SEQ ID No. 1, SEQ ID No. 3, SEQ ID No. 5, SEQ ID No. 7, SEQ ID No. 9 or SEQ ID No. 11.

Suitably, the degree of identity with regard to an amino acid or protein sequence may be determined over the whole sequence taught herein as SEQ ID No. 1.

In the present context, the term "query sequence" means a homologous sequence or a foreign sequence, which is aligned with a subject sequence in order to see if it falls within the scope of the present invention. Accordingly, such query sequence can for example be a prior art sequence or a third party sequence.

In one preferred embodiment, the sequences are aligned by a global alignment program and the sequence identity is calculated by identifying the number of exact matches identified by the program divided by the length of the subject sequence.

In one embodiment, the degree of sequence identity between a query sequence and a subject sequence is determined by 1) aligning the two sequences by any suitable alignment program using the default scoring matrix and default gap penalty, 2) identifying the number of exact matches, where an exact match is where the alignment program has identified an identical amino acid or nucleotide in the two aligned sequences on a given position in the alignment and 3) dividing the number of exact matches with the length of the subject sequence.

In yet a further preferred embodiment, the global alignment program is selected from the group consisting of CLUSTAL and BLAST (preferably BLAST) and the sequence identity is calculated by identifying the number of exact matches identified by the program divided by the length of the subject sequence.

The sequences may also have deletions, insertions or substitutions of amino acid residues result in a functionally equivalent substance. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ϵ-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

In one embodiment the xylanase for use in the present invention may comprise a polypeptide sequence shown as SEQ ID No. 1, SEQ ID No. 3, SEQ ID No. 5, SEQ ID No. 7, or SEQ ID No. 9 or SEQ ID No. 11 with a conservative substitution of at least one of the amino acids.

Suitably there may be at least 2 conservative substitutions, such as at least 3 or at least 4 or at least 5.

Suitably there may be less than 15 conservative substitutions, such as less than 12, less than 10, or less than 8 or less than 5.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Amino Acid Numbering

In the present invention, a specific numbering of amino acid residue positions in the xylanases used in the present invention may be employed. By alignment of the amino acid sequence of a sample xylanases with the xylanase of the present invention (particularly SEQ ID No. 1) it is possible to allot a number to an amino acid residue position in said sample xylanase which corresponds with the amino acid residue position or numbering of the amino acid sequence shown in SEQ ID No. 1 of the present invention.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringency conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Preferably hybridisation is analysed over the whole of the sequences taught herein.

Expression of Enzymes

The nucleotide sequence for use in the present invention may be incorporated into a recombinant replicable vector. The vector may be used to replicate and express the nucleotide sequence, in protein/enzyme form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of a protein having the specific properties as defined herein.

In one embodiment the organism is an expression host.

Thus, a further embodiment of the present invention provides host cells transformed or transfected with a nucleotide sequence that expresses the protein of the present invention.

The cells will be chosen to be compatible with the said vector and may for example be prokaryotic (for example bacterial), fungal or yeast cells.

Examples of suitable bacterial host organisms are gram positive or gram negative bacterial species.

In one embodiment the xylanases taught herein are expressed in the expression host *Trichoderma reesei*.

In some embodiments the expression host for the xylanases taught herein may be one or more of the following fungal expression hosts: *Fusarium* spp. (such as *Fusarium oxysporum*); *Aspergillus* spp. (such as *Aspergillus niger, A. oryzae, A. nidulans*, or *A. awamori*) or *Trichoderma* spp. (such as *T. reesei*).

In some embodiments the expression host may be one or more of the following bacterial expression hosts: *Streptomyces* spp. or *Bacillus* spp. (e.g. *Bacillus subtilis* or *B. licheniformis*).

The use of suitable host cells—such as yeast and fungal host cells—may provide for post-translational modifications (e.g. myristoylation, glycosylation, truncation, lipidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the polypeptide according to the present invention and/or products obtained therefrom, and/or wherein a promoter can allow expression of the nucleotide sequence according to the present invention when present in the organism.

In one embodiment the organism is an expression host.

Suitable organisms may include a prokaryote, fungus, yeast or a plant.

The term "transgenic organism" in relation to the present invention includes any organism that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the polypeptide of the present invention under the control of a heterologous promoter.

Transformation of Host Cells/Organism

As indicated earlier, the host organism can be a prokaryotic or a eukaryotic organism. Examples of suitable prokaryotic hosts include *E. coli, Streptomyces* spp. and *Bacillus* spp., e.g. *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Transformation of prokaryotes, fungi and yeasts are generally well known to one skilled in the art.

A host organism may be a fungus—such as a mould. Examples of suitable such hosts include any member belonging to the genera *Trichoderma* (e.g. *T. reesei*), *Thermomyces, Acremonium, Fusarium, Aspergillus, Penicillium, Mucor, Neurospora* and the like.

In one embodiment, the host organism may be a fungus. In one preferred embodiment the host organism belongs to the genus *Trichoderma*, e.g. *T. reesei*).

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Large Scale Application

In one preferred embodiment of the present invention, the amino acid sequence is used for large scale applications.

Preferably the amino acid sequence is produced in a quantity of from 1 g per litre to about 100 g per litre of the total cell culture volume after cultivation of the host organism.

Suitably the amino acid sequence may be produced in a quantity of from 30 g per litre to about 90 g per litre of the total cell culture volume after cultivation of the host organism.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

Assays

Activity Assay

Xylanases are assayed for xylanase activity on wheat WE-AX (water extractable arabinoxylan) in presence of bovine serum albumin (BSA). The amount of reducing end groups increases when xylanases active on soluble arabinoxylan hydrolyzes β1-4-bonds in the substrate. By heat and alkaline conditions the reducing end groups react with the colorless PAHBAH (4-Para-Hydroxybenzoic Acid Hydrazide), whereby PAHBAH is oxidized and absorbance is measured at 410 nm (Lever, 1972. Analytical Biochemistry 47, 273-279).

Buffers and Reagents:

100 mM sodium acetate (NaAc), pH 5.0, 0.10% BSA: 9.6 g sodium acetate trihydrate is dissolved in 800 ml deionized water and the pH is adjusted to 5.0 with concentrated acetic acid. Subsequently deionized water is added to 1000 ml. 1.0 g BSA (Sigma Aldrich, A7906) is dissolved in 1000 ml 100 mM NaAc, pH 5.0.

WE-AX, arabino xylan substrate 0.5%, pH 5.0: 0.5 g soluble wheat arabinoxylan ( MEGAZYME® high viscosity 43 cSt, P-WAXYH) is moistened with 5 ml 96% ethanol and 95 ml 100 mM NaAc, pH 5.0 was added. The solution is heated whilst stirring to boiling, and subsequently cooled whilst stirring to room temperature (RT).

PAHBAH working solution: Three solutions are prepared: 1) 0.5 M sodium hydroxide (NaOH): 10.0 g sodium hydroxide in 500 ml deionized water; 2) 0.5 M HCl: 20.8 ml 37% HCl in 500 ml deionized water; 3) 5% PAHBAH stock solution: 25.0 g PAHBAH (4-Hydroxybenzhydrazide, Sigma H9882) is dissolved in 500 ml 0.5 M HCl. The solution is protected against light and stored at 4° C. Just before use, the PAHBAH working solution was prepared by diluting the PAHBAH stock solution five times with 0.5 M NaOH.

Procedure:

All dilutions are prepared with a BIOMEK® dispensing robot (Beckman Coulter, USA) in MTPs (assay stock plate and assay plate: 96 well Clear Polystyrene Microplate, Corning, Cat. no. 9017; PCR plate: VWR, Eu. Cat No. 211-0297; Reading plate: Kisker Biotech, Cat. No. G080-F)

1. 3 µl enzyme sample (concentration ranging from 40-65 µg/ml) is diluted with 147 µl 100 mM NaAc, pH 5.0, 0.1% BSA buffer in the assay stock plate.
2. 25 µl sample from the assay stock plate is mixed with 150 µl WE-AX substrate in assay plate.

3. The assay plate is incubated at 30° C. and 1150 rpm shaking for 15 minutes in an iEMS® shaker (Thermo Scientific).
4. After end incubation 45.4 µl reaction mix from the assay plate is mixed with 135 µl PAHBAH working solution in a PCR plate.
5. The PCR plate is incubated in a PCR machine (TETRAD 2®, peltier thermo cycler, Bio-Rad) at 95° C. for 5 minutes and subsequently cooled to 20° C. for 10 sec.
6. 100 µl sample is transferred to a reading plate and the plate was read at 410 nm at a microplate reader (Molecular Devices).

The activity of all synthetic xylanases is calculated as the mean of three replicates subtracting a blank comprising 100 mM NaAc, pH 5.0, 0.1% BSA buffer instead of enzyme.

Thermostability Assay
Buffers and Reagents:
1% TWEEN® 80 (polysorbate 80): 1 g TWEEN® 80 (polysorbate 80) (Sigma P-8074) is dissolved with 9 ml MES buffer, pH 6.0 and subsequently diluted additionally 10 times with MES buffer, pH 6.

25 mM MES buffer, pH 6.0, 0.00125% Tween 80: 25 mM MES buffer, pH 6.0: 4.88 g MES (2-(N-morpholino)-ethanesulfonic acid) is dissolved in 800 ml deionized water and the pH is adjusted to 6.0 with NaOH. 1.25 ml 1% Tween80 was added followed by addition of deionized water to 1000 ml.

Procedure:
Thermostability of the synthetic xylanase is measured by incubating the synthetic xylanases at approximately 1 µg/ml protein concentration (range: 0.8-1.3 µg/ml) in 25 mM MES buffer, 0.00125% TWEEN® 80 (polysorbate 80), pH 6.0 for 10 minutes at elevated temperature. At the end of the incubation, the residual activity for the heat treated synthetic xylanases is measured as described in the Activity Assay (steps 2-6).

The residual activity of each synthetic xylanase is calculated as the mean of three replicates subtracted blank including 25 mM MES buffer, 0.00125% TWEEN® 80 (polysorbate 80), pH 6.0 instead of enzyme. The residual activity is calculated as the ratio between the activity measured for the heat treated sample and the activity measured for an identical sample, which has not been incubated at elevated temperature.

Pepsin Resistance Assay
The ability of synthetic xylanases to withstand pepsin degradation is tested at 40° C. in a buffered solution at pH 3.5.

The ability of synthetic xylanases to withstand pepsin degradation is measured by incubating the synthetic xylanases in 100 mM Glycine buffer, pH 3.5 containing 0.2 g/l pepsin for 2 hours at 40° C. and 1150 rpm in an iEMS® shaker (Thermo scientific). At the end of the incubation, the residual activity for the synthetic xylanases is measured as described in Activity Assay (steps 2-6).

Buffers and Reagents:
100 mM Glycine buffer, pH 3.5: 7.52 g glycine is dissolved in 800 ml deionized water and the pH was adjusted to pH 3.5 with HCl. Subsequently deionized water is added to 1000 ml. 0.2 mg/ml Pepsin solution: 0.2 g pepsin (Sigma, P-7000) is dissolved in 1000 ml 100 mM glycine buffer pH 3.5.

The residual activity of each synthetic xylanase is calculated as the mean of three replicates subtracted blank including 0.2 mg/ml pepsin solution instead of enzyme. The residual activity of each synthetic xylanase is calculated as the ratio between the activity measured for the pepsin treated samples and the activity measured fin the activity assay using non-treated samples.

Solubilisation Assay
Buffers and Reagents:
100 mM MES buffer, pH 6.0: 19.52 g MES (2-(N-morpholino)-ethanesulfonic acid) is dissolved in 800 ml deionized water and the pH is adjusted to 6.0 with NaOH. Subsequently deionized water is added to 1000 ml.

Corn DDGS substrate solution, 10%: cDDGS with particle size<212 µm is hydrated in 100 mM MES buffer pH 6.0 by stirring 15 min at 600 rpm. Immediately after stirring is terminated, the pH is adjusted if there is a drop in pH caused by acid residues in the cDDGS. 190 µl/well cDDGS substrate is transferred to the substrate plates, which are stored at −20° C. until use.

Procedure:
All dilutions are prepared with a BIOMEK® dispensing robot (Beckman Coulter, USA) in MTPs (substrate plate and collection plate: 96 well Clear Polystyrene Microplate, Corning, Cat. no. 9017; Filter plate: 0.2 µm PVDF membrane, Corning, Cat. no. 3504; half deep well plate: Low profile 1.2 ml square storage plate, Cat. No. AB-1127, Thermo Scientific.
1. 10 µl enzyme sample (apparent concentration of 150 µg/ml) is added to the premade substrate plates.
2. Incubation in iEMS at 40° C. for 240 minutes.
3. 170 µl sample from the incubated substrate plate is transferred to a filter plate.
4. The filter plates are placed on top of a collection plates and centrifuged for 10 min at 1666×g.
5. The collection plates are stored at −20° C. before further analysis.
6. 100 µl from the collection plate was diluted with 900 µl MILLI-Q® (ultrapure water in a half deep well plate and mixed for 2 minutes at a shaking table before transfer to the Skalar apparatus.

Quantification of Pentosans
Total amount of C5 sugars (pentosans) brought into solution is measured using a continuous flow injection apparatus (SKALAR system) according to the method described by Rouau & Surget (1994, Carbohydrate Polymers, 24, 123-132). The supernatants are treated with a mixture of $CH_3COOH$ and HCl to hydrolyse polysaccharides to monosugars. Phloroglucinol (1, 3, 5-trihydroxybenzen) is added to react with monopentoses and monohexoses to form a coloured complex. By measuring the absorbance at 550 nm with 510 nm as reference wavelength, the concentration of pentose in solution is calculated using a xylose standard curve (50-400 µg xylose/ml). Unlike the pentose-phloroglucinol complex, the absorbance of the hexose-phloroglucinol complex is constant at these wavelengths. Glucose (0.3%) is added to the phloroglucinol solution to create a constant glucose signal and further ensure no interference from hexose sugars.

The results may be presented as performance index (PI) which were calculated as the ratio between the values after incubation of cDDGS respectively with and without addition of the synthetic xylanase: (total amount of C5-sugars in solution after incubation with synthetic xylanase)/(total amount of C5-sugars in solution after incubation without enzyme present).

Pelleting Process and Determination of Residual Xylanase Activity after a Feed Comprising the Polypeptide has been Conditioned for 30 Seconds at 90° C., e.g. as Part of a Pelleting Process During the pelleting process an enzyme may be formulated on a substrate, e.g. wheat, and may be formulated into a premix, e.g. a corn/soy feed mix (such as 61.1% Corn, 31.52% Hipro Soya 48, 4.00% Soya Oil, 0.40% Sodium Bicarbonate, 0.25% Vitamins/Minerals Leghennen, 0.20% DL-methionine, 1.46% Dicalcium Phosphate, 1.16% Limestone).

The xylanase can be included at a level which ensures a final target dosage is achieved, e.g. 20 000 XU/kg feed. The premix may be prepared by mixing the enzyme(s) formulated on the substrate, e.g. wheat, into a feed mixture (meal), e.g. 10 kg corn/soy feed mix, and mixed for a specified time, e.g. 10 min.

The premix may be added to feed, e.g. 110 kg feed, and mixed for a specified time, e.g. 10 min, before conditioning. The feed comprising the enzyme is typically conditioned for 30 seconds at 90° C. before pelleting.

The term "conditioned" or "conditioning" as used herein means mixing the feed/enzyme mixture and treating same with dry steam to reach a target temperature of 90° C. after 30 seconds.

Conditioning may be carried out by placing the feed/enzyme mixture in a mixer, e.g. a cascade mixer (such as a KAHL mixer, length 130 cm, diameter 30 cm, speed 155 rpm).

The dwell time for 300 kg/h is approx. 30 sec., calculated as follows:
Capacity: 300 kg/h-83.3 g/sec.
Measured filling in cascade mixer: 2500 g.
Dwell time in cascade mixer: 2500 g: 83.3 g/sec.=30 sec.

Mounted on the side of the cascade mixer may be a manifold with a water discharger and 3 steam valves from which steam can be directed to the meal (e.g. feed mixture) or feed/enzyme mixture.

Steam in this system may be provided by a high-pressure boiler, e.g. Dan Stoker boiler, max. capacity 400 kg steam/h. Tests can be conducted with 2 ato overpressure and the steam may be led via a pressure reduction valve, which controls the addition of steam to the cascade mixer. Three valves on the manifold may be used for fine adjustment of the desired meal (e.g. feed mixture) or feed/enzyme mixture temperature. By adding 1% steam the meal (e.g. feed mixture) or feed/enzyme mixture temperature increases by 14° C.

Following the conditioning the feed/enzyme mixture may be formed into pellets. The pellets may be formed in a Simon Heesen pellet press with a Ø 3 mm*35 mm die. The capacity is set to 300 kg/hour and is adjusted to the dosing screw. The meal/premix is heated to target temperature between 65 and 95° C. by steam in the cascade mixer. The steam quantity may be regulated by a pressure reduction valve and a manifold. For each temperature level a sample is first taken when operation is established after 8-10 min. pelleting.

The pellet press may be a Simon Heesen, type labor (monoroll) with 7.5 kW motor. Internal diameter of die: 173 mm, height of press roll: 50 mm, diameter of press roll: 140 mm. Pellet press: 500 rpm and nominal capacity: 300 kg/h.

Samples may be taken after the pellet press. They are cooled, e.g. in a partitioned cooling box with perforated bottom, Ventilator: 1500 m3 air/h.

The xylanase containing feed mixture (meal) and resulting feed pellets are ground using a Perten laboratory mill, before xylanase activity in the samples are analyzed using azurine cross linked arabinoxylan from wheat as substrate. 5.0 g of ground sample is mixed with 50 ml McIlvaine buffer, pH 5.0 and stirred on a magnetic stirrer for 10 min. The extract is filtered through a glass fiber filter. 100 μl extract was mixed with 400 μl McIlvaine buffer, pH 5.0 and equilibrated at 50° C. for 2 min. A 60 mg Xylazyme tablet (Megazyme, Ireland) is added to initiate the reaction and samples are incubated at 50° C. for 60 min before the reaction is stopped by adding 5 ml of 2% Tris(hydroxymethyl)aminomethane (Sigma, T-1503). The solution is mixed using vortex, left to stand for 5 min and mixed again before centrifuged at 3500 rpm for 10 min. Absorbance of the supernatant is measured at 590 nm. Each sample is measured in duplicate.

Xylanase activity is quantified using a xylanase standard curve prepared on blank (no enzyme) meal and 90° C. feed. The activity for the meal sample comprising xylanase is set to 100% and the residual activity of the synthetic xylanase in the pellet of feed conditioned at 90° C. is calculated as relative to this.

The invention will now be described, by way of example only, with reference to the following Figures and Examples.

EXAMPLES

Example 1

Generation of Synthetic Xylanases

Plasmid Construction

The genes encoding the synthetic xylanases shown as SEQ ID No. 2, 4, 6, 8, 10 and 12 were generated via a de novo gene synthesis (GeneArt GmbH, Germany). Synthetic xylanases were then cloned by the vendor into the destination vector pTTT-pyr2 via a Gateway recombination technique (Invitrogen, Carlsbad, Calif., USA). The resulting expression plasmids pTTTpyr2-synXyn_VAR (FIG. 13) expressing the synthetic xylanases were amplified in the *Escherichia coli* DH5a strain, purified, sequenced, arrayed individually in 96 MTPs and used for fungal transformation as described further. The expression vector contains the *T. reesei* cbhI promoter and terminator regions allowing for a strong inducible expression of a gene of interest, the *Aspergillus nidulans* amdS and *T. reesei* pyr2 selective markers conferring growth of transformants on minimal medium with acetamide in the absence of uridine. The plasmids are maintained autonomously in the fungal cell due to *T. reesei* derived telomere regions. Usage of replicative plasmids results in increased frequencies of transformation and circumvents problems of locus-dependent expression observed with integrative fungal transformation.

Fungal Strains, Growth Media and Transformation

Expression plasmids (5-10 ul) were transformed using a PEG-protoplast method into a *T. reesei* strain deleted for major cellulases and xylanase 2 (Δcbh1 Δcbh2 Δegl1 Δegl2 Δegl3 Δegl4 Δegl5 Δegl6 Δbgl1 Δman1 ΔLxyn2 Prdiv: iRNAxyn1 xyn3: amdS pyr2-). Additional downregulation of the endogenous xylanase 1 and 3 background was further achieved via introducing into the host strain genome an iRNA interference cassette targeting to shut down the xyn1 and xyn3 expression simultaneously. All high throughput transformations were performed robotically in a 24 well MTP format using BIOMEK® robots (Beckman Coulter, USA). Plasmids with synthetic xylanases were received from the vendors in 96 well MTPs arrayed according to a predetermined layout. Transformation mixtures containing approximately 1 μg of DNA and $5 \times 10^6$ protoplasts in a total volume of 50 μl were treated with 200 ul of 25% PEG solution, diluted with 1 volumes of 1.2M sorbitol/10 mM Tris, pH7.5/10 mM $CaCl_2$ solution, rearranged robotically into 24 well MTPs and mixed with 1 ml of 3% agarose Minimal Medium containing 1M sorbitol and 10 mM NH4Cl. After growth of transformants, spores from each well were pooled and repatched on fresh 24 well MTPs with MM containing acetamide for additional selective pressure. Once sporulated, spores were harvested and used for inoculation of liquid cultures either in a 24-well MTP format or shake flasks in the following production medium: 37 g/L glucose, 1 g/L sophorose, 9 g/L casmino acids, 10 g/L $(NH_4)_2SO_4$, 5 g/L $KH_2PO_4$, 1 g/L $CaCl_2 \times 2H_2O$, 1 g/L $MgSO_4 \times 7H_2O$, 33 g/L 1,4-Piperazinebis(propanesulfonic acid), pH 5.5, 2.5 ml/L of 400×*T. reesei* trace elements (175 g/L citric acid, 200 g/L $FeSO4 \times 7H_2O$, 16 g/L $ZnSO4 \times 7H_2O$, 3.2 g/L $CuSO4 \times 5H_2O$, 1.4 g/L $MnSO4 \times H_2O$, 0.8 g/L boric acid). 1 ml of production medium was added to produce synthetic xylanases in 24 well MTPs. For shake flasks, volumes were scaled up.

Plates were grown for 6 days at 28° C. and 80% humidity with shaking at 200 rpm. Cells were harvested by centrifugation at 2500 rpm for 10 minutes and filtered through MILLIPORE® Multiscreen filterplate using a MILLIPORE® vacuum system. Culture supernatants were harvested by vacuum filtration and used to assay their performance as well as expression level.

Protein profile of the whole broth samples was determined by PAGE electrophoresis on NuPAGE® Novex 10% Bis-Tris Gel with MES SDS Running Buffer (Invitrogen, Carlsbad, Calif, USA). Polypeptide bands were visualized with SIMPLYBLUE® SafeStain (Invitrogen, Carlsbad, Calif., USA).

For larger scale production fermentation in a 6 Liter autoclaveable Continuers Stirred Reactor was conducted. Shake flasks were inoculated with spores and incubated with shaking for 3 days at 28° C. in the following shake flask medium: 5 g/L $(NH_4)_2SO_4$, 4.5 g/L $KH_2PO_4$, 1 g/L $MgSO_4 \times 7H_2O$, 14.4 g/L citric acid×$1H_2O$, 1 g/L $CaCl_2 \times 2H_2O$, 27.5 g/L glucose, 1 drop antifoam agent (EROL DF 6000K). The pH was adjusted with NaOH (2M) to 5.5 and media was autoclaved 20 minutes at 122° C. After cooling 2.5 ml/L of 400×*T. reesei* trace elements (175 g/L citric acid, 200 g/L $FeSO4 \times 7H_2O$, 16 g/L $ZnSO4 \times 7H_2O$, 3.2 g/L $CuSO4 \times 5H_2O$, 1.4 g/L $MnSO4 \times H_2O$, 0.8 g/L boric acid) was added. Cells from the shake flask was used to inoculate the bioreactor containing the following Bioreactor medium: 4.7 g/L $KH_2PO_4$, 1 g/L $MgSO_4 \times 7H_2O$, 4.3 g/L $(NH_4)_2SO_4$, 45 g/L glucose, 0.7 g/L $CaCl_2 \times 2H_2O$, 0.3 g/L antifoam agent (EROL DF 6000K), 2.5 ml/L of 400×*T. reesei* trace elements (175 g/L citric acid, 200 g/L $FeSO4 \times 7H_2O$, 16 g/L $ZnSO4 \times 7H_2O$, 3.2 g/L $CuSO4 \times 5H_2O$, 1.4 g/L $MnSO4 \times H_2O$, 0.8 g/L boric acid). Temperature was controlled at 34° C.; pH was continuously controlled by adding 20% ammoniumhydroxide. Dissolved oxygen was controlled to minimum 40% saturation by varying the stirring rate. Off gas carbon dioxide and oxygen content were measured. When the initial glucose was depleted a constant feeding of a glucose/sophorose was started. At the same time temperature was reduced to and controlled at 28° C., pH was increased to and controlled at 4.5. The fermentation was terminated after 140 hours. Broth was removed from the tank, and cells were removed by filtration. After cell separation the filtrate was concentrated by ultrafiltration. Finally, the concentrate was sterile filtered and used for pelleting stability studies.

Example 2

Synthetic Xylanase Performance

In addition to being good on bio-efficacy (e.g. have a positive effect on animal performance) new xylanase products for commercial use, e.g. for feed application also need to have good product characteristics including processing stability.

Synthetic polypeptides have been identified having xylanase activity. The synthetic polypeptides were found to be thermostable. The synthetic xylanases were found to have high recovery (residual activity) after undergoing the pelleting process. The synthetic xylanases were able to degrade WU-AX (water unextractable arabinoxylan) from DDGS (e.g. corn DDGS—and thus solubilize corn). Furthermore, the synthetic polypeptides were found to be resistant towards pepsin degradation.

The purpose of the synthetic xylanases in feed is to maximize energy utilization of a feedstuff by having more insoluble fibers digested and taken into solution, thereby make more nutrients available and thus producing more fermentable non-starch polysaccharides (NSP).

In addition to high bio-efficacy (e.g. have a positive effect on animal performance) the new synthetic xylanases taught herein also have good product characteristics including thermostability, stability against heat processing (e.g. pelleting) and/or pepsin resistance.

The synthetic xylanases were tested in a series of tests detailed in the material and methods section below.

Materials and Methods

Normalization

The synthetic xylanases were normalized based on activity. Crude samples were diluted 20 and 130 times, respectively and activity was measured using the activity assay together with a commercial xylanase standard curve with the following concentrations: 0, 10, 20, 30, 40, 50, 60 and 70 μg/ml. The samples were diluted in 25 mM NaAcetate, 250 mM NaCl, pH 4.0. Samples with an apparent concentration of less than 1000 μg/ml were quantified using the 20 times dilution, while the remaining of the samples were quantified using the 130 times dilution. The synthetic xylanase crude samples were subsequently diluted to an apparent concentration of 150 μg/ml with 25 mM NaAcetate, 250 mM NaCl, pH 4.0 in a micro titer plate (MTP) (the normalized plate) with a well volume at 210 μl. 53 μl of the normalized sample were diluted to an apparent concentration of 50 μg/ml with 107 μl 25 mM NaAcetate, 250 mM NaCl, pH 4.0.

Quantification

The samples in the normalized plate were quantified using the CRITERION® Gel system. Laemmli sample buffer (Bio-rad #161-0737) was mixed with Dithiothreitol (DTT) (Bio-rad #161-0611) and MILLI-Q® (ultrapure) water to a final concentration after enzyme addition at 50% Laemmli sample buffer with 50 mM DTT. 70 μl Laemmli sample buffer mix was mixed thoroughly with 10 μl sample from the normalized plate in parallel to a standard curve made of purified commercial xylanase diluted with 25 mM NaAcetate, 250 mM NaCl, pH 4.0 to the following concentrations: 120, 160, 200, 240, 280 and 320 μg/ml.

The molecular weight (Mw), Tryptophan number in addition to the Tryptophan number to Mw ratio for each of the synthetic xylanases is given in Table 1. The concentration of each xylanase was calculated by correcting the apparent commercial xylanase concentration, which was done by multiplying the Tryptophan number to Mw ratio for the commercial xylanase divided by the Tryptophan number to Mw ratio for the synthetic xylanase. The concentration for all synthetic xylanase samples in the normalized plate were determined to be in the range of 120-200 μg/ml.

TABLE 1

Mw and Tryptophan number to Mw ratios for each of the synthetic xylanases

|  | MW | #W | #W/MW |
|---|---|---|---|
| SynXyn72 | 32593 | 7 | 0.02147 |
| SynXyn80 | 33103 | 7 | 0.02114 |
| SynXyn85 | 32929 | 7 | 0.02125 |
| SynXyn89 | 32854 | 7 | 0.02130 |
| SynXyn92 | 32894 | 7 | 0.02128 |
| SynXyn93 | 32894 | 7 | 0.02128 |
| Commercial xylanase | 33254 | 8 | 0.02406 |

Activity Assay

The synthetic xylanases were assayed for xylanase activity on wheat WE-AX (water extractable arabinoxylan) in presence of bovine serum albumin (BSA). The amount of reducing end groups increased when xylanases active on soluble arabinoxylan hydrolyzed β1-4-bonds in the substrate. By heat and alkaline conditions the reducing end groups reacted with the colorless PAHBAH (4-Para-Hydroxybenzoic Acid Hydrazide), whereby PAHBAH was oxidized and absorbance was measured at 410 nm (Lever, 1972, *Analytical Biochemistry*, 47, 273-279).

Buffers and Reagents:

100 mM sodium acetate (NaAc), pH 5.0, 0.10% BSA: 9.6 g sodium acetate trihydrate was dissolved in 800 ml deionized water and the pH was adjusted to 5.0 with concentrated acetic acid. Subsequently deionized water was added to 1000 ml. 1.0 g BSA (Sigma Aldrich, A7906) was dissolved in 1000 ml 100 mM NaAc, pH 5.0.

WE-AX, arabino xylan substrate 0.5%, pH 5.0: 0.5 g soluble wheat arabinoxylan (MEGAZYME® high viscosity 43 cSt, P-WAXYH) was moistened with 5 ml 96% ethanol and 100 ml 100 mM NaAc, pH 5.0 was added. The solution was heated under stirring to boiling, and subsequently cooled under stirring to room temperature (RT).

PAHBAH working solution: Three solutions were prepared: 1) 0.5 M sodium hydroxide (NaOH): 10.0 g sodium hydroxide in 500 ml deionized water; 2) 0.5 M HCl: 20.8 ml 37% HCl in 500 ml deionized water; 3) 5% PAHBAH stock solution: 25.0 g PAHBAH (4-Hydroxybenzhydrazide, Sigma H9882) was dissolved in 500 ml 0.5 M HCl. The solution was protected against light and store at 4° C. Just before use the PAHBAH working solution was prepared by diluting the PAHBAH stock solution five times with 0.5 M NaOH.

Procedure:

All dilutions were prepared with a BIOMEK® dispensing robot (Beckman Coulter, USA) in MTPs (assay stock plate and assay plate: 96 well Clear Polystyrene Microplate, Corning, Cat. no. 9017; PCR plate: VWR, Eu. Cat No. 211-0297; Reading plate: Kisker Biotech, Cat. No. G080-F)

1. 3 µl enzyme sample (concentration ranging from 40-65 µg/ml) was diluted with 147 µl 100 mM NaAc, pH 5.0, 0.1% BSA buffer in the assay stock plate.
2. 25 µl sample from the assay stock plate was mixed with 150 µl WE-AX substrate in assay plate.
3. The assay plate was incubated at 30° C. and 1150 rpm shaking for 15 minutes in an iEMS® shaker (Thermo Scientific).
4. After end incubation 45.4 µl reaction mix from the assay plate was mixed with 135 µl PAHBAH working solution in a PCR plate.
5. The PCR plate was incubated in a PCR machine (TETRAD 2®, peltier thermo cycler, Bio-Rad) at 95° C. for 5 minutes and subsequently cooled to 20° C. for 10 sec.
6. 100 µl sample was transferred to a reading plate and the plate was read at 410 nm at a microplate reader (Molecular Devices).

The activity of all synthetic xylanases was calculated as the mean of three replicates subtracted a blank including 100 mM NaAc, pH 5.0, 0.1% BSA buffer instead of enzyme.

Thermostability Assay

Buffers and Reagents: 1% Tween80: 1 g TWEEN® 80 (polysorbate 80) (Sigma P-8074) was dissolved with 9 ml MES buffer, pH 6.0 and subsequently diluted additionally 10 times with MES buffer, pH 6. 25 mM MES buffer, pH 6.0, 0.00125% TWEEN® 80 (polysorbate 80): 25 mM MES buffer, pH 6.0: 4.88 g MES (2-(N-morpholino)-ethanesulfonic acid) was dissolved in 800 ml deionized water and the pH was adjusted to 6.0 with NaOH. 1.25 ml 1% TWEEN® 80 (polysorbate 80) was added followed by addition of deionized water to 1000 ml.

Procedure:

Thermostability of the synthetic xylanase was measured by incubating the synthetic xylanases at approximately 1 µg/ml protein concentration (range: 0.8-1.3 µg/ml) in 25 mM MES buffer, 0.00125% TWEEN® 80 (polysorbate 80), pH 6.0 for 10 minutes at elevated temperature. After end incubation, the residual activity for the heat treated synthetic xylanases was measured as described in the Activity Assay (steps 2-6).

The activity of each synthetic xylanase was calculated as the mean of three replicates subtracted blank including 25 mM MES buffer, 0.00125% TWEEN® 80 (polysorbate 80), pH 6.0 instead of enzyme. The residual activity is calculated as the ratio between the activity measured for the heat treated sample and the activity measured for an identical sample, which had not been incubated at elevated temperature.

Pepsin Resistance Assay

The ability of synthetic xylanases to withstand pepsin degradation was tested at 40° C. in a buffered solution at pH 3.5.

The ability of synthetic xylanases to withstand pepsin degradation was measured by incubating the synthetic xylanases in 100 mM Glycine buffer, pH 3.5 containing 0.2 g/l pepsin for 2 hours at 40° C. and 1150 rpm in an iEMS® shaker (Thermo scientific). At the end of the incubation, the residual activity for the synthetic xylanases was measured as described in Activity Assay (steps 2-6).

Buffers and Reagents:

100 mM Glycine buffer, pH 3.5: 7.52 g glycine was dissolved in 800 ml deionized water and the pH was adjusted to pH 3.5 with HCl. Subsequently deionized water was added to 1000 ml. 0.2 mg/ml Pepsin solution: 0.2 g pepsin (Sigma, P-7000) was dissolved in 1000 ml 100 mM glycine buffer pH 3.5.

The activity of each synthetic xylanase was calculated as the mean of three replicates subtracted blank including 0.2 mg/ml pepsin solution instead of enzyme. The residual activity of each synthetic xylanase is calculated as the ratio between activity measured for the pepsin treated samples and the activity measured in the activity assay using non-treated samples.

Solubilisation Assay

Buffers and Reagents:

100 mM MES buffer, pH 6.0: 19.52 g MES (2-(N-morpholino)-ethanesulfonic acid) was dissolved in 800 ml deionized water and the pH was adjusted to 6.0 with NaOH. Subsequently deionized water was added to 1000 ml.

Corn DDGS substrate solution, 10%: cDDGS with particle size<212 µm was hydrating in 100 mM MES buffer pH 6.0 by stirring 15 min at 600 rpm. Immediately after stirring was terminated the pH was adjusted due to a drop in pH caused by acid residues in the cDDGS. 190 µl/well cDDGS substrate was transferred to the substrate plates, which were stored at −20° C. until use.

Procedure:

All dilutions were prepared with a BIOMEK® dispensing robot (Beckman Coulter, USA) in MTPs (substrate plate and collection plate: 96 well Clear Polystyrene Microplate, Corning, Cat. no. 9017; Filter plate: 0.2 µm PVDF membrane, Corning, Cat. no. 3504; half deep well plate: Low profile 1.2 ml square storage plate, Cat. No. AB-1127, Thermo Scientific.

1. 10 µl enzyme sample (apparent concentration of 150 µg/ml) was added to the premade substrate plates.
2. Incubation in iEMS® at 40° C. for 240 minutes.
3. 170 µl sample from the incubated substrate plate was transferred to a filter plate.
4. The filter plates were placed on top of a collection plates and centrifuged for 10 min at 1666×g.
5. The collection plates were stored at −20° C. before further analysis.
6. 100 µl from the collection plate was diluted with 900 µl MILLI-Q® (ultrapure) water in a half deep well plate and mixed for 2 minutes at a shaking table before transfer to the Skalar apparatus.

Quantification of Pentosans

Total amount of C5 sugars (pentosans) brought into solution was measured using a continuous flow injection apparatus (SKALAR system) according to the method described by Rouau & Surget (1994, Carbohydrate Polymers, 24, 123-132). The supernatants were treated with a mixture of $CH_3COOH$ and HCl to hydrolyse polysaccharides to monosugars. Phloroglucinol (1, 3, 5-trihydroxybenzen) was added to react with monopentoses and monohexoses to form a coloured complex. By measuring the absorbance at 550 nm with 510 nm as reference wavelength, the concentration of pentose in solution was calculated using a xylose standard curve (50-400 µg xylose/ml). Unlike the pentose-phloroglucinol complex, the absorbance of the hexose-phloroglucinol complex was constant at these wavelengths. Glucose (0.3%) was added to the phloroglucinol solution to create a constant glucose signal and further ensure no interference from hexose sugars.

The results are presented as performance index (PI) which were calculated as the ratio between the values after incubation of cDDGS respectively with and without addition of the synthetic xylanase: (total amount of C5-sugars in solution after incubation with synthetic xylanase)/(total amount of C5-sugars in solution after incubation without enzyme present).

Pelleting Stability

Pelleting trials were performed in full scale at Technological Institute, Kolding, Denmark. Each xylanase was formulated on wheat and mixed into a corn/soy feed mix (61.1% Corn, 31.52% Hipro Soya 48, 4.00% Soya Oil, 0.40% Sodium Bicarbonate, 0.25% Vitamins/Minerals Leghennen, 0.20% DL-methionine, 1.46% Dicalcium Phosphate, 1.16% Limestone).

The xylanase was included to reach a final target at 20 000 XU/kg feed. A premix was prepared by mixing the xylanases formulated on wheat into 10 kg corn/soy feed mix and mixed for 10 min. The premix was then added to 110 kg feed and mixed for 10 min before conditioning. The feed comprising the enzyme was conditioned for 30 seconds at 90° C. before pelleting. The term "conditioning" as used herein means mixing the feed/enzyme mixture and treating same with dry steam to reach a target temperature of 90° C. after 30 seconds.

Conditioning was carried out by placing the feed/enzyme mixture in a cascade mixer, namely a KAHL mixer, length 130 cm, diameter 30 cm, speed 155 rpm).

The dwell time for 300 kg/h is approx. 30 sec., calculated as follows:

Capacity: 300 kg/h-83.3 g/sec.
Measured filling in cascade mixer: 2500 g.
Dwell time in cascade mixer: 2500 g: 83.3 g/sec.=30 sec.

Mounted on the side of the cascade mixer was a manifold with a water discharger and 3 steam valves from which steam was directed to the meal (e.g. feed mixture) or feed/enzyme mixture.

Steam in this system was provided by a high-pressure Dan Stoker boiler, max. capacity 400 kg steam/h. Tests were conducted with 2 ato overpressure and the steam may be led via a pressure reduction valve, which controls the addition of steam to the cascade mixer. Three valves on the manifold may be used for fine adjustment of the desired meal (e.g. feed mixture) or feed/enzyme mixture temperature. By adding 1% steam the meal (e.g. feed mixture) or feed/enzyme mixture temperature increases by 14° C.

Following the conditioning the feed/enzyme mixture was formed into pellets. The pellets were formed in a Simon Heesen pellet press with a Ø 3 mm*35 mm die. The capacity was set to 300 kg/hour and was adjusted to the dosing screw. The meal was heated to target temperature between 65 and 95° C. by steam in the cascade mixer. The steam quantity was regulated by a pressure reduction valve and a manifold. For each temperature level a sample was first taken when operation is established after 8-10 min. pelleting.

The pellet press was a Simon Heesen, type labor (monoroll) with 7.5 kW motor. Internal diameter of die: 173 mm, height of press roll: 50 mm, diameter of press roll: 140 mm. Pellet press: 500 rpm and nominal capacity: 300 kg/h.

Samples were taken after the pellet press. They are cooled, e.g. in a partitioned cooling box with perforated bottom, Ventilator: 1500 m3 air/h.

The xylanase containing feed mixture (meal) and resulting feed pellets were ground using a Perten laboratory mill, before xylanase activity in the samples were analyzed using azurine cross linked arabinoxylan from wheat as substrate. 5.0 g of ground sample was mixed with 50 ml McIlvaine buffer, pH 5.0 and stirred on a magnetic stirrer for 10 min. The extract was filtered through a glass fiber filter. 100 µl extract was mixed with 400 µl McIlvaine buffer, pH 5.0 and equilibrated at 50° C. for 2 min. A 60 mg Xylazyme tablet (MEGAZYME®,Ireland) was added to initiate the reaction and samples were incubated at 50° C. for 60 min before the reaction was stopped by adding 5 ml of 2% Tris (Sigma, T-1503). The solution was mixed using vortex, left to stand for 5 min and mixed again before centrifuged at 3500 rpm for 10 min. Absorbance of the supernatant was measured at 590 nm. Each sample was measured in duplicate.

Xylanase activity was quantified using a standard curve prepared on blank (no enzyme) mash and 90° C. feed. The wheat formulated SynXyn92 xylanase was extracted for 10 minutes in McIlvaine buffer, pH 5.0 to obtain a concentration of 160 U/ml. The extract was filtered through a glass fiber filter and hereafter 0, 200, 400, 600, 800, and 1000 µl extract was added to 5.0 g samples of ground blank mash and 90° C. feed. Xylanase activity in these standard samples was measured as described in the extract method above.

The activity for the meal sample comprising xylanase is set to 100% and the residual activity of the synthetic xylanase in the pellet of feed conditioned at 90° C. is calculated as relative to this.

Results

The synthetic xylanases taught herein are good at in vitro degradation of WU-AX (water unextractable arabinoxylan) from cDDGS, have acceptable specific activities at pH 5, are thermostable and are resistant towards pepsin degradation at pH 3.5 (with a residual activity of at least 70% after 2 hours incubation). Feed processing stability has been determined for the synthetic enzymes designated herein as synXyn92 and the feed processing stability were consider to be high (with a residual activity of at least 80% for treatment at 90° C.).

TABLE 2

Residual activities after 10 minutes incubation at selected temperatures (61° C., 65° C. or 71° C.), residual activities after 2 h incubations in the presence of pepsin and PI for pentosan solubilisation for the synthetic xylanases listed herein. Synthetic xylanases with PI greater than 1.5 were considered to be able to degrade WU-AX from cDDGS.

| Sample Name | Thermostability. Residual activity. Incubation temperature: 61° C. | Thermostability. Residual activity. Incubation temperature: 65° C. | Thermostability. Residual activity. Incubation temperature: 71° C. | Pepsin resistance. Residual activity. | Pentosan solubilisation PI relative to blank |
|---|---|---|---|---|---|
| SYNXYN85 | 1.03 | 1.02 | | 1.06 | 1.5 |
| SYNXYN92 | 1.00 | 1.00 | | 1.08 | 1.8 |
| SYNXYN89 | 1.01 | 0.88 | | 1.05 | 1.7 |
| SYNXYN72 | 0.99 | 0.68 | | 1.05 | 1.7 |
| SYNXYN80 | 0.95 | 0.65 | | 0.98 | 1.7 |
| SYNXYN93 | | | 0.99 | 1.13 | |

| | Identity to SynXyn92 SEQ ID No 1 (%) |
|---|---|
| SynXyn72 | 89 |
| SynXyn80 | 92 |
| SynXyn85 | 90 |
| SynXyn89 | 94 |
| SynXyn92 | 100 |
| SynXyn93 | 99 |

Table 3 shows the sequence identity in a pair wise alignment expressed as percent. The identity percentages were calculated using the Indonesia software suit, which also was used for preparation of sequence alignments. The identity percentages were calculated by dividing the number of identical amino acids with the number of amino acids for the shortest polypeptide.

Processing stability in the form of feed pelleting stability was determining using a standard procedure at Danish Technological Institute and is described in pelleting stability in the materials and methods section. The residual activity after pelleting was 84% for SynXyn92. A recovery at 80% after pelleting would be considered as full recovery.

The synthetic sequences designated herein as SynXyn 92, SynXyn85, SynXyn89, SynXyn72, SynXyn80 and SynXyn93 also gave a positive response when tested in the Activity Assay. Polypeptides resulting in an OD (410 nm)>0.7 when analysed under the conditions mentioned in Activity Assay are considered as having xylanase activity.

Example 3

Wheat Viscosity Reduction

In the European fuel alcohol industry, small grains like wheat, barley and rye are common raw materials, in contrast to the US where mainly corn is used. These small grains contain, next to starch, high levels of non-starch polysaccharide polymers (NSP), like cellulose, beta-glucan and hemicellulose.

The ratio in which the different NSPs are represented differ for each feedstock. Table 1 shows the different amounts of NSPs in wheat, barley and rye compared to some other feedstocks.

TABLE 1

Non-starch Polysaccharides present in different feedstocks (g kg$^{-1}$ dry matter)[1,2]

| | | | | Barley | | Oats | |
|---|---|---|---|---|---|---|---|
| | Corn | Wheat | Rye | Hulled | Hulless | Hulled | Hulless |
| Beta-Glucan | 1 | 8 | 16 | 42 | 42 | 28 | 41 |
| Cellulose | 22 | 17-20 | 15-16 | 43 | 10 | 82 | 14 |
| Soluble and Non-soluble NCP[3] | 75 | 89-99 | 116-136 | 144 | 114 | 150 | 113 |
| Total NSP | 97 | 107-119 | 132-152 | 186 | 124 | 232 | 116 |

[1]Bach Knudsen, K. E, 1997. Carbohydrate and lignin contents of plant materials used in animal feeding. Anim. Feed Sci. Technol., 67 (4): 319-338
[2]Englyst, H. N., Anderson, V. and Cummings, J. H., 1983. Starch and non-starch polysaccharides in some cereal foods. J. Sci. Food Agric., 34: 1434-1440.
[3]Non Cellulosic Polysaccharides: pentosans, (arabino)xylans and other hemicelluloses NSPs give high viscosity to grain mashes. High viscosity has a negative impact on ethanol production since it will limit the solid concentration that can be used in mashing and it will reduce the energy efficiency of the process. In addition, residual hemicelluloses present throughout the process may contribute to fouling in heat exchangers and distillation equipment. The largest impact of a high viscosity is seen when a mash is cooled to fermentation temperature (32° C.). This explains that the viscosity needs to be reduced in the process anywhere before the cooling step. Depending on the process used, enzymes are needed that operate at 60° C. and/or 85° C.

Viscosity reducing enzymes can be added in different stages of the ethanol production process: mixing and/or saccharification/fermentation. Preferably the enzymes are added in mixing to breakdown initial viscosity.

The benefits of using viscosity reduction enzymes in the ethanol production process are multiple:
Higher dry substance mash can be used in the process
Higher solids content of final syrup can be obtained
Better heat transfer, lower energy requirement
Reduced evaporator fouling leading to reduced cleaning costs
Increased final ethanol yields
Improved quality of DDGS
Methods A Rapid Visco Analyzer (RVA 4500) from Perten Instruments was used to measure viscosity profiles of a wheat mash. This wheat mash was prepared according to following protocol: Prepare 60 grams of 30% DS (34.65% 'as is') wheat slurry (for simultaneous runs on two RVA's) as follows:
Weigh 20.80 grams of wheat
In a 100 ml beaker glass, weigh 39.20 grams of tap water and add 137 µl 4N $H_2SO_4$
Add the wheat to the water and stir for 5 minutes at maximum speed (approx. 500 rpm) with an overhead stirrer
Transfer 25.0 grams of slurry to an RVA cup, add 50-fold diluted enzymes and start RVA run (check if starting pH is around 5.3)
Check pH at end of RVA run (5.6-5.7)

In each experiment (25 grams of slurry), xylanase was dosed at 25 µg protein (per 8.66 g wheat 'as is'), corresponding to 2.9 µg protein/g wheat 'as is'. SPEZYME® CL was dosed at 0.15 kg/MT wheat 'as is' (2.2 AAU/g 'as is' or 2.6 AAU/g DS).

A standard wheat liquefaction was mimicked in the RVA. Pretreatment was performed for 20 minutes at 60° C., followed by a liquefaction step for 30 minutes at 85° C. After pretreatment and liquefaction, slurry was cooled down to 32° C., to determine viscosity at fermentation conditions. Liquefaction pH was kept between 5.3-5.7.

In this experiment, the performance of SynXyn93 was compared to a known xylanase with viscosity reducing properties (positive control).

| | Viscosity (mPa*s) | | |
|---|---|---|---|
| | Blank (n = 2) | Positive control enzyme | SynXyn93 |
| After pretreatment (1200 sec. process time) | 533 ± 16 | 224 | 592 |
| After liquefaction (3120 sec. process time) | 347 ± 16 | 130 | 167 |

| | Viscosity (mPa*s) | | |
|---|---|---|---|
| | Blank (n = 2) | Positive control enzyme | SynXyn93 |
| At fermentation temperature (3660 sec. process time) | 765 ± 20 | 275 | 341 |

Figure 16:
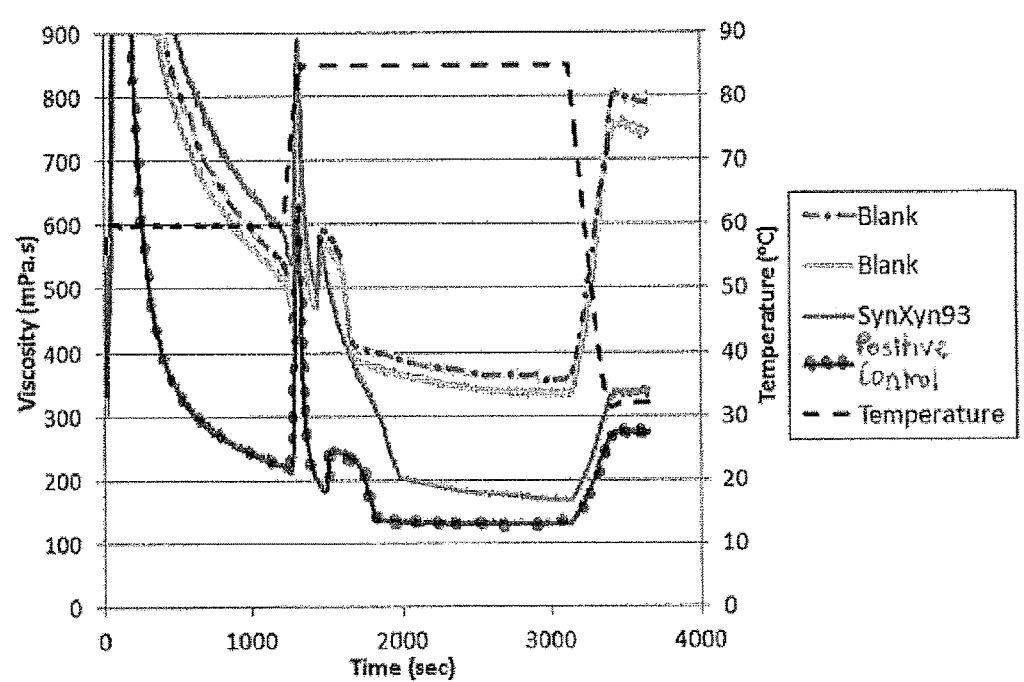
FIG. 16 shows viscosity reduction in grain based material of synthetic enzyme SynXyn93 according to the present invention compared with a positive control enzyme. These data show that SynXyn93 enzyme has no activity during pretreatment step (60° C.), but catches up in liquefaction step (85° C.). The viscosity reduction continues during the liquefaction step at 85° C., indicating that SynXyn93 has significant activity at this elevated temperature. Final viscosities with SynXyn93 are 52-55% lower than blank.

The Data is Shown in FIG. 16.

These data show that SynXyn93 enzyme has no activity during pretreatment step (60° C.), but catches up in liquefaction step (85° C.). The viscosity reduction continues during the liquefaction step at 85° C., indicating that SynXyn93 has significant activity at this elevated temperature. Final viscosities with SynXyn93 are 52-55% lower than blank.

A follow up experiment was performed where xylanase enzyme was added at liquefaction temperature (85° C.), rather than at the beginning of the process. This was done to demonstrate the improved Thermostability of SynXyn93. For these runs, a special spindle with injection port was used, enabling the addition of enzyme during the RVA run. Spindle was stopped for 1 minute when liquefaction temperature (85° C.) was reached (22 minutes process time) and xylanase enzyme was added. Injection port was rinsed with 50 µl demi water and spindle started rotating again at 23 minutes process time. In these runs, SPEZYME® CL was added at the beginning of the process.

| | Viscosity (mPa*s) | | |
|---|---|---|---|
| | Blank (n = 2) | Positive control enzyme | SynXyn93 |
| After pretreatment (1200 sec. process time) | 533 ± 16 | 603 * | 552 * |
| After liquefaction (3120 sec. process time) | 347 + 16 | 209 | 159 |
| At fermentation temperature (3660 sec. process time) | 765 ± 20 | 449 | 308 |

* No xylanase added in pretreatment, so same value expected as blank

Figure 17:
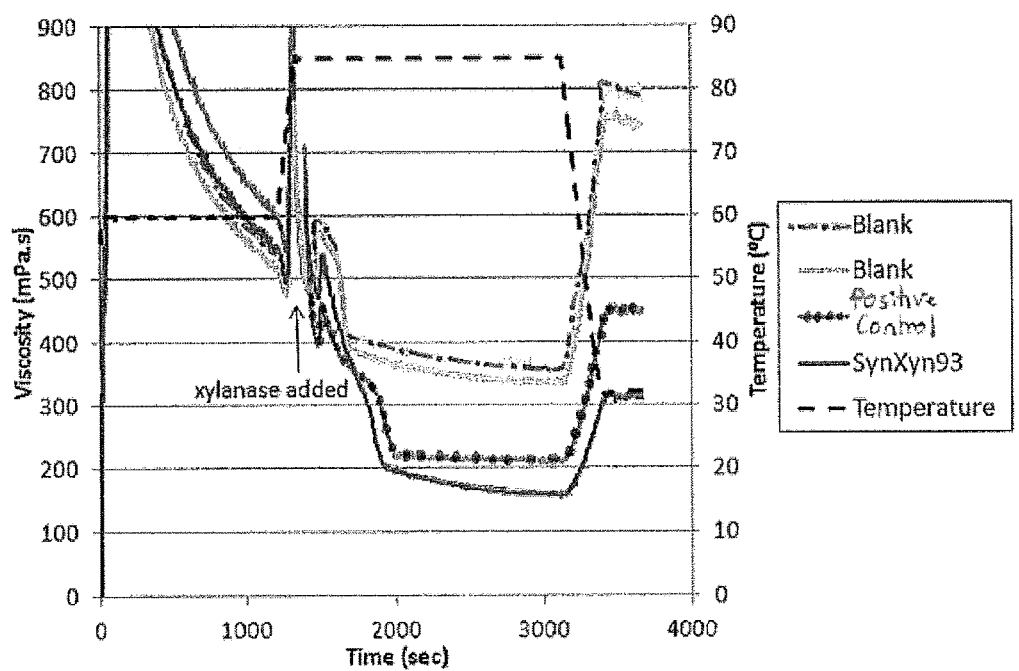
FIG. 17 shows viscosity reduction in grain based material of synthetic enzyme SynXyn93 according to the present invention compared with a positive control enzyme. These data confirms the increased thermostability of SynXyn93 compared to the positive control enzyme. SynXyn93 shows viscosity reduction of 54-60% compared to the blank, whereas for the positive control enzyme is only 40-41%. The final viscosity with SynXyn93 is lower than with the positive control enzyme.

The data is shown in FIG. 17.

These data confirms the increased thermostability of SynXyn93 compared to the positive control enzyme. SynXyn93 shows viscosity reduction of 54-60% compared to the blank, whereas for the positive control enzyme is only 40-41%. For SynXyn93 there is no difference in performance when added at beginning of the process or at 85° C. The positive control enzyme on the other hand is considerably impacted when added at 85° C. instead of at beginning of process: viscosity reduction (compared to blank) is reduced from 63% to 41%. So in this case final viscosity with SynXyn93 is lower than with the positive control enzyme.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A polypeptide having xylanase activity, selected from the group consisting of:
   (a) a polypeptide comprising an amino acid sequence having at least 94% identity with SEQ ID NO: 1; or
   (b) a polypeptide encoded by a polynucleotide having at least 94% identity with SEQ ID NO:2.

2. The polypeptide according to claim 1, wherein the polypeptide comprises the amino acid sequence of SEQ ID No. 1.

3. The polypeptide of claims 1 or 2 wherein the polypeptide is encoded by the polynucleotide of SEQ ID No. 2.

4. The polypeptide of claims 1 or 2, wherein the polypeptide is an endo-1,4-β-xylanase.

5. The polypeptide of claims 1 or 2, wherein the polypeptide has at least 50% residual activity of xylanase activity after incubation at 65° C. for 10 minutes at pH 6 and/or has at least 80% residual activity of xylanase activity after incubation at 61° C. for 10 minutes at pH 6.

6. The polypeptide according to claim 1, wherein the polypeptide has a residual activity of at least 70% when incubated with 0.2 mg/ml pepsin in a buffered solution at pH 3.5 for two hours at a temperature of 40° C.

7. The polypeptide according to claim 1, wherein the polypeptide solubilizes arabinoxylans without increasing viscosity in a reaction medium.

8. A feed or feedstuff comprising the polypeptide of claims 1 or 2.

9. A method for producing the polypeptide of claims 1 or 2 comprising (a) cultivating a host cell comprising a polynucleotide having at least 94% identity with SEQ ID No. 2 under conditions conducive for production of the polypeptide; and (b) recovering the polypeptide.

10. The method according to claim 9 wherein the polypeptide produced is isolated and/or purified.

11. A method for solubilizing arabinoxylan in a xylan-containing material by contacting the xylan-containing material with the polypeptide of claims 1 or 2.

12. The method of claim 11 wherein the arabinoxylan is insoluble arabinoxylan (AXinsol).

13. The method of claim 11 wherein the xylan-containing material is selected from one or more of the group consisting of: a feed or feedstuff; a feed component; a grain-based material; a mash; a wort; a malt; malted barley; an adjunct, a barley mash; and a cereal flour.

14. The method of claim 13 wherein the feed or feedstuff or feed component comprises or consists of corn, Distillers Dried Grain Solubles (DDGS), corn based Distillers Dried Grain Solubles (cDDGS), wheat, wheat bran or a combination thereof.

15. The method of claim 11 wherein the polypeptide is used in combination with one or more of the enzymes selected from the group consisting of endoglucanases (E.C. 3.2.1.4) celliobiohydrolases (E.C. 3.2.1.91), β-glucosidases (E.C. 3.2.1.21), cellulases (E.C. 3.2.1.74), lichenases (E.C. 3.2.1.73), lipases (E.C. 3.1.1.3), lipid acyltransferases (E.C. 2.3.1.x), phospholipases (E.C. 3.1.1.4, E.C. 3.1.1.32 and E.C. 3.1.1.5), 6-phytase (E.C. 3.1.3.26) 3-phytase (E.C. 3.1.3.8), amylases, alpha-amylases (E.C. 3.2.1.1), xylanases (E.C. 3.2.1.8, E.C. 3.2.1.32, E.C. 3.2.1.37, E.C. 3.2.1.72, and E.C. 3.2.1.136), glucoamylases (E.C. 3.2.1.3), hemicellulases, subtilisin (E.C. 3.4.21.62) bacillolysin (E.C. 3.4.24.28) alkaline serine proteases (E.C. 3.4.21.x) akeratinases (E.C. 3.4.x.x), debranching enzymes, cutinases, esterases and β-mannanase (E.C. 3.2.1.78).

16. The method of claim 12 wherein the polypeptide is used in combination with one or more of the enzymes selected from the group consisting of endoglucanases (E.C. 3.2.1.4) celliobiohydrolases (E.C. 3.2.1.91), β-glucosidases (E.C. 3.2.1.21), cellulases (E.C. 3.2.1.74), lichenases (E.C. 3.2.1.73), lipases (E.C. 3.1.1.3), lipid acyltransferases (E.C. 2.3.1.x), phospholipases (E.C. 3.1.1.4, E.C. 3.1.1.32 and E.C. 3.1.1.5), 6-phytase (E.C. 3.1.3.26) 3-phytase (E.C. 3.1.3.8), amylases, alpha-amylases (E.C. 3.2.1.1), xylanases (E.C. 3.2.1.8, E.C. 3.2.1.32, E.C. 3.2.1.37, E.C. 3.2.1.72, and E.C. 3.2.1.136), glucoamylases (E.C. 3.2.1.3), hemicellulases, subtilisin (E.C. 3.4.21.62) bacillolysin (E.C. 3.4.24.28) alkaline serine proteases (E.C. 3.4.21.x) akeratinases (E.C. 3.4.x.x), debranching enzymes, cutinases, esterases and β-mannanase (E.C. 3.2.1.78).

17. The method of claim 13 wherein the polypeptide is used in combination with one or more of the enzymes selected from the group consisting of endoglucanases (E.C. 3.2.1.4) celliobiohydrolases (E.C. 3.2.1.91), β-glucosidases (E.C. 3.2.1.21), cellulases (E.C. 3.2.1.74), lichenases (E.C. 3.2.1.73), lipases (E.C. 3.1.1.3), lipid acyltransferases (E.C. 2.3.1.x), phospholipases (E.C. 3.1.1.4, E.C. 3.1.1.32 and E.C. 3.1.1.5), 6-phytase (E.C. 3.1.3.26) 3-phytase (E.C. 3.1.3.8), amylases, alpha-amylases (E.C. 3.2.1.1), xylanases (E.C. 3.2.1.8, E.C. 3.2.1.32, E.C. 3.2.1.37, E.C. 3.2.1.72, and E.C. 3.2.1.136), glucoamylases (E.C. 3.2.1.3), hemicellulases, subtilisin (E.C. 3.4.21.62) bacillolysin (E.C. 3.4.24.28) alkaline serine proteases (E.C. 3.4.21.x) akeratinases (E.C. 3.4.x.x), debranching enzymes, cutinases, esterases and β-mannanase (E.C. 3.2.1.78).

\* \* \* \* \*

```
                        SEQUENCE LISTING

<160> NUMBER OF SEQ ID NOS: 12

<210> SEQ ID NO 1
<211> LENGTH: 302
<212> TYPE: PRT
<213> ORGANISM: Artificial Sequence
<220> FEATURE:
<223> OTHER INFORMATION: Synthetic xylanase SynXyn92

<400> SEQUENCE: 1

Gln Ala Ala Ala Ser Ile Asn Asn Ala Phe Lys Ala His Gly Lys Lys
1               5                   10                  15

Tyr Phe Gly Thr Cys Ala Asp Gln Asp Thr Leu Thr Asn Pro Lys Asn
            20                  25                  30

Ala Ala Ile Ile Lys Ala Asp Phe Gly Gln Leu Thr Pro Glu Asn Ser
        35                  40                  45

Met Lys Trp Asp Ala Thr Glu Pro Ser Gln Gly Lys Phe Asn Phe Gly
    50                  55                  60

Gly Ala Asp Tyr Leu Val Asn Phe Ala Lys Gln Asn Gly Lys Leu Ile
65                  70                  75                  80

Arg Gly His Thr Leu Val Trp His Ser Gln Leu Pro Ser Trp Val Gln
                85                  90                  95

Asn Ile Asn Asp Lys Asn Thr Leu Thr Lys Val Met Lys Asn His Ile
            100                 105                 110

Thr Thr Val Met Ser Arg Tyr Lys Gly Lys Ile Tyr Ala Trp Asp Val
        115                 120                 125

Val Asn Glu Ile Phe Asn Glu Asp Gly Thr Leu Arg Asn Ser Val Phe
    130                 135                 140

Tyr Asn Val Leu Gly Glu Asp Phe Val Arg Ile Ala Phe Glu Thr Ala
145                 150                 155                 160

Arg Ala Ala Asp Pro Asn Ala Lys Leu Tyr Ile Asn Asp Tyr Asn Leu
                165                 170                 175

Asp Ser Ala Asn Tyr Ala Lys Thr Lys Gly Met Val Ser His Val Lys
            180                 185                 190

Lys Trp Ile Ala Glu Gly Ile Pro Ile Asp Gly Ile Gly Ser Gln Thr
        195                 200                 205

His Leu Gly Ala Gly Gly Ala Gly Val Ala Gly Ala Leu Asn Ala
    210                 215                 220

Leu Ala Ala Gly Val Ser Glu Val Ala Ile Thr Glu Leu Asp Ile
225                 230                 235                 240

Ala Gly Ala Ser Ser Asn Asp Tyr Val Asn Val Val Lys Ala Cys Leu
                245                 250                 255

Asn Glu Pro Lys Cys Val Gly Ile Thr Val Trp Gly Val Ser Asp Lys
            260                 265                 270

Asp Ser Trp Arg Ser Asp Asp Asn Pro Leu Leu Phe Asp Ser Asn Tyr
        275                 280                 285

Lys Pro Lys Ala Ala Tyr Asn Ala Ile Ile Asp Ala Leu Arg
    290                 295                 300

<210> SEQ ID NO 2
<211> LENGTH: 978
<212> TYPE: DNA
<213> ORGANISM: Artificial Sequence
```

<220> FEATURE:
<223> OTHER INFORMATION: Synthetic xylanase SynXyn92

<400> SEQUENCE: 2

```
atgaagctca gctcgttcct ctacaccgcc agcctcgtcg ctgccatccc taccgctatc      60
gagccccgac aggctgctgc cagcatcaac aacgccttca aggcccacgg caagaagtac     120
ttcggcactt gcgccgacca ggacacgctc accaacccca gaacgccgc catcatcaag      180
gccgacttcg gccagctcac ccccgagaac agcatgaagt gggacgccac cgagcccagc     240
cagggcaagt tcaactttgg cggcgctgac tacctcgtca acttcgccaa gcagaacggc     300
aagctcatcc gcggccacac cctcgtctgg cacagccagc tccctagctg ggtccagaac     360
atcaacgaca gaacaccct gaccaaggtc atgaagaacc acatcaccac cgtcatgagc      420
cgctacaagg gcaagatcta cgcctgggac gtcgtcaacg agatcttcaa cgaggacggc     480
accctccgca cagcgtctt ttacaacgtc ctgggcgagg acttcgtccg cattgccttc      540
gagactgccc gagccgccga ccccaacgct aagctctaca tcaacgacta caacctcgac     600
agcgccaact acgccaagac caagggcatg gtcagccacg tcaagaagtg gatcgccgag     660
ggcatcccca tcgacggcat cggcagccag actcaccttg gcgctggcgg cggcgctggc     720
gttgctggcg ctctcaacgc tctggccgct gccggcgtca gcgaggtcgc catcaccgag     780
ctggacattg ctggcgctag cagcaacgac tacgtcaacg tcgtcaaggc tgcctcaac     840
gagcccaagt gcgtcggcat caccgtctgg ggcgtcagcg acaaggacag ctggcgcagc     900
gacgacaacc cctcctctct cgactccaac tacaagccca aggccgccta caacgccatc     960
atcgacgccc tccgctaa                                                   978
```

<210> SEQ ID NO 3
<211> LENGTH: 304
<212> TYPE: PRT
<213> ORGANISM: Artificial Sequence
<220> FEATURE:
<223> OTHER INFORMATION: Synthetic xylanase SynXyn85

<400> SEQUENCE: 3

```
Gln Ala Ala Ala Ser Ile Asn Asn Ala Phe Lys Ala His Gly Lys Lys
1               5                   10                  15

Tyr Phe Gly Thr Cys Ala Asp Gln Asp Thr Leu Ser Asn Ser Gln Asn
            20                  25                  30

Ala Ala Ile Ile Lys Ala Asp Phe Gly Gln Leu Thr Pro Glu Asn Ser
        35                  40                  45

Met Lys Trp Asp Ala Thr Glu Pro Ser Gln Gly Lys Phe Asn Phe Ala
    50                  55                  60

Gly Ala Asp Tyr Leu Val Asn Tyr Ala Lys Gln Asn Gly Lys Leu Val
65                  70                  75                  80

Arg Gly His Thr Leu Val Trp His Ser Gln Leu Pro Ser Trp Val Ser
                85                  90                  95

Ala Ile Thr Asp Lys Asn Thr Leu Thr Ser Val Met Lys Asn His Ile
            100                 105                 110

Thr Thr Val Met Ser Arg Tyr Lys Gly Gln Ile Tyr Ala Trp Asp Val
        115                 120                 125

Val Asn Glu Ile Phe Asn Glu Asp Gly Thr Leu Arg Asn Ser Val Phe
    130                 135                 140

Tyr Asn Val Leu Gly Glu Asp Phe Val Arg Ile Ala Phe Glu Thr Ala
145                 150                 155                 160
```

```
Arg Ala Val Asp Pro Asp Ala Lys Leu Tyr Ile Asn Asp Tyr Asn Leu
            165                 170                 175

Asp Ser Ala Asn Tyr Ala Lys Thr Gln Gly Met Val Ser His Val Lys
        180                 185                 190

Lys Trp Leu Ala Ala Gly Ile Pro Ile Asp Gly Ile Gly Ser Gln Thr
            195                 200                 205

His Leu Ser Pro Gly Gly Leu Ser Ser Ser Gly Val Ala Gly Ala Leu
        210                 215                 220

Thr Ala Leu Ala Ser Thr Gly Val Ser Glu Val Ala Ile Thr Glu Leu
225                 230                 235                 240

Asp Ile Ala Gly Ala Ser Ser Asn Asp Tyr Val Asn Val Val Lys Ala
                245                 250                 255

Cys Leu Asp Val Pro Lys Cys Val Gly Ile Thr Val Trp Gly Val Ser
            260                 265                 270

Asp Lys Asp Ser Trp Arg Ser Asp Asp Ser Pro Leu Leu Phe Asp Ser
        275                 280                 285

Asn Tyr Gln Pro Lys Ala Ala Tyr Asn Ala Ile Ile Asp Ala Leu Ser
    290                 295                 300
```

<210> SEQ ID NO 4
<211> LENGTH: 984
<212> TYPE: DNA
<213> ORGANISM: Artificial Sequence
<220> FEATURE:
<223> OTHER INFORMATION: Synthetic xylanase SynXyn85

<400> SEQUENCE: 4

```
atgaagctca gctcgttcct ctacaccgcc agcctcgtcg ccgctatccc taccgctatc      60
gagccccgac aggccgctgc cagcatcaac aacgccttca aggcccacgg caagaagtac     120
ttcggcactt gcgccgacca ggacaccctc agcaacagcc agaacgccgc catcatcaag     180
gccgacttcg ccagctcac ccccgagaac agcatgaagt gggacgccac cgagcccagc      240
cagggcaagt tcaacttcgc tggcgccgac tacctcgtca actacgctaa gcagaacggc     300
aagctcgtcc gcggccacac cctcgtctgg cacagccagc tcccgtcctg ggtcagcgcc     360
atcaccgaca gaacaccct caccagcgtc atgaagaacc acatcaccac cgtcatgagc      420
cgctacaagg ccagatcta cgcctgggac gtcgtcaacg agatcttcaa cgaggacggc      480
acctccgca actccgtctt ttacaacgtc ctcggcgagg acttcgtccg cattgccttc      540
gagactgccc gagccgtcga ccccgacgcc aagctctaca tcaacgacta caacctcgac     600
agcgccaact acgccaagac ccagggcatg gtcagccacg tcaagaagtg gctcgctgcc     660
ggcatcccca tcgacggcat cggcagccag acccacctca gccctggcgg cctcagcagc     720
agcggcgtcg ctggcgctct caccgccctc gcctctaccg gcgtcagcga ggtcgccatt     780
accgagctgg acattgctgg cgctagcagc aacgactacg tcaacgtcgt caaggcctgc     840
ctcgacgtcc ccaagtgcgt cggcatcacc gtctggggcg tcagcgacaa ggacagctgg     900
cgcagcgacg acagcccccct cctcttcgac tccaactacc agcccaaggc cgcctacaac     960
gccatcatcg acgccctcag ctaa                                            984
```

<210> SEQ ID NO 5
<211> LENGTH: 304
<212> TYPE: PRT
<213> ORGANISM: Artificial Sequence
<220> FEATURE:
<223> OTHER INFORMATION: Synthetic xylanase SynXyn89

<400> SEQUENCE: 5

```
Gln Ala Ala Ala Ser Ile Asn Asn Ala Phe Lys Ala His Gly Lys Lys
1               5                   10                  15
Tyr Phe Gly Thr Cys Ala Asp Gln Gly Thr Leu Ser Asn Ser Lys Asn
            20                  25                  30
Ala Ala Ile Ile Lys Ala Asp Phe Gly Gln Leu Thr Pro Glu Asn Ser
        35                  40                  45
Met Lys Trp Asp Ala Thr Glu Pro Ser Gln Gly Lys Phe Asn Phe Gly
50                  55                  60
Gly Ala Asp Tyr Leu Val Asn Tyr Ala Lys Gln Asn Gly Lys Leu Ile
65                  70                  75                  80
Arg Gly His Thr Leu Val Trp His Ser Gln Leu Pro Ser Trp Val Gln
                85                  90                  95
Asp Ile Thr Asp Lys Asn Thr Leu Thr Ser Val Met Lys Asn His Ile
            100                 105                 110
Thr Thr Val Met Ser Arg Tyr Lys Gly Lys Ile Tyr Ala Trp Asp Val
        115                 120                 125
Val Asn Glu Ile Phe Asn Glu Asp Gly Thr Leu Arg Asn Ser Val Phe
130                 135                 140
Tyr Asn Val Leu Gly Glu Asp Phe Val Arg Ile Ala Phe Glu Thr Ala
145                 150                 155                 160
Arg Ala Ala Asp Pro Asp Ala Lys Leu Tyr Ile Asn Asp Tyr Asn Leu
                165                 170                 175
Asp Ser Ala Asn Tyr Ala Lys Thr Lys Gly Met Val Ser His Val Lys
            180                 185                 190
Lys Trp Ile Ala Ala Gly Ile Pro Ile Asp Gly Ile Gly Ser Gln Thr
        195                 200                 205
His Leu Gly Ala Gly Gly Leu Ser Gly Ser Gly Val Ala Gly Ala Leu
210                 215                 220
Asn Ala Leu Ala Ser Thr Gly Val Ser Glu Val Ala Ile Thr Glu Leu
225                 230                 235                 240
Asp Ile Ala Gly Ala Ser Ser Asn Asp Tyr Val Asn Val Val Lys Ala
                245                 250                 255
Cys Leu Asn Val Pro Lys Cys Val Gly Ile Thr Val Trp Gly Val Ser
            260                 265                 270
Asp Lys Asp Ser Trp Arg Ser Asp Ser Pro Leu Leu Phe Asp Ser
        275                 280                 285
Asn Tyr Gln Pro Lys Ala Ala Tyr Asn Ala Ile Ile Asp Ala Leu Ser
290                 295                 300
```

<210> SEQ ID NO 6
<211> LENGTH: 984
<212> TYPE: DNA
<213> ORGANISM: Artificial Sequence
<220> FEATURE:
<223> OTHER INFORMATION: Synthetic xylanase SynXyn89

<400> SEQUENCE: 6

```
atgaagctca gctcgttcct ctacaccgcc agcctcgtcg ccgctatccc taccgccatc      60
gagccccgac aggccgctgc cagcatcaac aacgccttca aggcccacgg caagaagtac     120
ttcggcactt gcgccgacca gggcacgctc agcaacagca agaacgccgc catcatcaag     180
gccgacttcg gccagctcac ccccgagaac agcatgaagt gggacgccac cgagcccagc     240
cagggcaagt tcaactttgg cggcgctgac tacctcgtca actacgctaa gcagaacggc     300
```

```
aagctcatcc gcggccacac cctcgtctgg cacagccagc tcccgtcctg ggtccaggac    360
atcaccgaca gaacaccct caccagcgtc atgaagaacc acatcaccac cgtcatgagc     420
cgctacaagg gcaagatcta cgcctgggac gtcgtcaacg agatcttcaa cgaggacggc   480
accctccgca actccgtctt ttacaacgtc ctcggcgagg acttcgtccg cattgccttc   540
gagactgccc gagccgccga ccccgacgcc aagctctaca tcaacgacta caacctcgac   600
agcgccaact acgccaagac caagggcatg gtcagccacg tcaagaagtg gatcgctgcc   660
ggcatcccca tcgacggcat cggcagccag acccacctcg gcgctggcgg cctttctggc   720
tctggcgtgg ctggcgccct caacgccctc gccagcaccg cgtcagcga ggtcgccatc    780 accgagctgg acattgctgg cgctagcagc aacgactacg tcaacgtcgt caaggcctgc   840
ctcaacgtcc ccaagtgcgt cggcatcacc gtctggggcg tcagcgacaa ggacagctgg   900
cgcagcgacg acagccccct cctcttcgac tccaactacc agcccaaggc cgcctacaac   960
gccatcatcg acgccctcag ctaa                                           984
```

<210> SEQ ID NO 7
<211> LENGTH: 301
<212> TYPE: PRT
<213> ORGANISM: Artificial Sequence
<220> FEATURE:
<223> OTHER INFORMATION: Synthetic xylanase SynXyn72

<400> SEQUENCE: 7

```
Gln Ala Ala Ala Ser Ile Asn Asn Ala Phe Lys Ala Lys Gly Lys Lys
1               5                   10                  15

Tyr Phe Gly Thr Cys Ala Asp Gln Gly Thr Leu Ser Asp Ser Thr Asn
            20                  25                  30

Ser Ala Ile Ile Lys Ala Asp Phe Gly Gln Leu Thr Pro Glu Asn Ser
        35                  40                  45

Met Lys Trp Asp Ala Thr Glu Pro Ser Gln Gly Lys Phe Ser Phe Gly
    50                  55                  60

Gly Ala Asp Tyr Leu Val Asn Tyr Ala Thr Ser Asn Gly Lys Leu Ile
65                  70                  75                  80

Arg Gly His Thr Leu Val Trp His Ser Gln Leu Pro Ser Trp Val Gln
                85                  90                  95

Gly Ile Thr Asp Lys Asn Thr Leu Thr Ser Val Leu Lys Asn His Ile
            100                 105                 110

Thr Thr Val Met Asn Arg Tyr Lys Gly Lys Ile Tyr Ala Trp Asp Val
        115                 120                 125

Val Asn Glu Ile Phe Asn Glu Asp Gly Thr Leu Arg Asn Ser Val Phe
    130                 135                 140

Tyr Asn Val Leu Gly Glu Asp Phe Val Arg Ile Ala Phe Glu Thr Ala
145                 150                 155                 160

Arg Ala Val Asp Pro Gln Ala Lys Leu Tyr Ile Asn Asp Tyr Asn Leu
                165                 170                 175

Asp Ser Ala Asn Tyr Ala Lys Thr Lys Gly Met Ala Asn His Val Lys
            180                 185                 190

Lys Trp Ile Ala Gln Gly Ile Pro Ile Asp Gly Ile Gly Ser Gln Thr
        195                 200                 205

His Leu Gly Ala Gly Gly Ser Ser Gly Val Lys Gly Ala Leu Asn Thr
    210                 215                 220

Leu Ala Ser Ser Gly Val Ser Glu Val Ala Ile Thr Glu Leu Asp Ile
225                 230                 235                 240
```

```
Ala Gly Ala Ser Ser Asn Asp Tyr Val Asn Val Val Lys Ala Cys Leu
                245                 250                 255

Asn Val Ser Lys Cys Val Gly Ile Thr Val Trp Gly Val Ser Asp Lys
            260                 265                 270

Asp Ser Trp Arg Ser Asp Ser Pro Leu Leu Phe Asp Ser Asn Tyr
        275                 280                 285

Gln Pro Lys Ala Ala Tyr Asn Ala Ile Ile Asn Ala Leu
    290                 295                 300

<210> SEQ ID NO 8
<211> LENGTH: 975
<212> TYPE: DNA
<213> ORGANISM: Artificial Sequence
<220> FEATURE:
<223> OTHER INFORMATION: Synthetic xylanase SynXyn72

<400> SEQUENCE: 8
atgaagctca gctcgttcct ctacaccgcc agcctcgtcg ccgccatccc taccgccatc      60
gagccccgac aggccgctgc cagcatcaac aacgccttca aggccaaggg caagaagtac     120
ttcggcactt gcgccgacca gggcacgctc agcgacagca ccaacagcgc catcatcaag     180
gccgacttcg gccagctcac ccccgagaac agcatgaagt gggacgccac cgagcccagc     240
cagggcaagt tcagctttgg cggcgctgac tacctcgtca actacgccac cagcaacggc     300
aagctcatcc gcgccacaca cctcgtctgg cacagccagc tcccgtcctg ggtccagggc     360
atcaccgaca agaacaccct caccagcgtc ctcaagaacc acatcaccac cgtcatgaac     420
cgctacaagg gcaagatcta cgcctgggac gtcgtcaacg agatcttcaa cgaggatggc     480
accctccgca acagcgtctt ttacaacgtc ctgggcgagg acttcgtccg cattgccttc     540
gagactgccc gagccgtcga ccccaggcc aagctctaca tcaacgacta caacctcgac     600
agcgccaact acgccaagac caagggcatg gccaaccacg tcaagaagtg gatcgcccag     660
ggcatcccca tcgacggcat cggcagccag acccacctcg gcgctggcgg ctctagcggc     720
gtcaagggcg ctctcaacac cctcgccagc tccggcgtca gcgaggtcgc catcaccgag     780
ctggacattg ctggcgcctc gagcaacgac tacgtcaacg tcgtcaaggc ctgcctcaac     840
gtcagcaagt gcgtcggcat caccgtctgg ggcgtctccg acaaggacag ctggcgcagc     900
gacgacagcc cctcctcttt cgactccaac taccagccca aggccgccta caacgccatc     960
attaacgccc tctaa                                                     975

<210> SEQ ID NO 9
<211> LENGTH: 302
<212> TYPE: PRT
<213> ORGANISM: Artificial Sequence
<220> FEATURE:
<223> OTHER INFORMATION: Synthetic xylanase SynXyn80

<400> SEQUENCE: 9

Gln Ala Ala Ala Ser Ile Asp Ala Lys Phe Lys Ala His Gly Lys Lys
1               5                   10                  15

Tyr Phe Gly Asn Ile Ala Asp Gln Tyr Thr Leu Thr Lys Asn Pro Lys
            20                  25                  30

Thr Ala Ala Ile Ile Lys Ala Asp Phe Gly Gln Leu Thr Pro Glu Asn
        35                  40                  45

Ser Met Lys Trp Asp Ala Thr Glu Pro Ser Arg Gly Lys Phe Asn Phe
    50                  55                  60
```

Gly Gly Ser Asp Tyr Leu Val Asn Phe Ala Lys Gln Asn Asn Lys Leu
65                  70                  75                  80

Ile Arg Gly His Thr Leu Val Trp His Ser Gln Leu Pro Ser Trp Val
            85                  90                  95

Gln Asn Ile Asn Asp Lys Asn Thr Leu Thr Gln Val Met Lys Asn His
        100                 105                 110

Ile Thr Thr Val Met Ser Arg Tyr Lys Gly Lys Ile Tyr Ala Trp Asp
    115                 120                 125

Val Val Asn Glu Ile Phe Asn Glu Asp Gly Thr Leu Arg Asn Ser Val
130                 135                 140

Phe Tyr Asn Val Leu Gly Glu Asp Phe Val Arg Ile Ala Phe Glu Thr
145                 150                 155                 160

Ala Arg Ala Ala Asp Pro Asn Ala Lys Leu Tyr Ile Asn Asp Tyr Asn
                165                 170                 175

Leu Asp Ser Ala Asn Tyr Ala Lys Thr Lys Gly Met Val Ser His Val
            180                 185                 190

Lys Lys Trp Ile Ala Glu Gly Ile Pro Ile Asp Gly Ile Gly Ser Gln
        195                 200                 205

Thr His Leu Gly Ala Gly Gly Ala Gly Val Ser Gly Ala Leu Asn
    210                 215                 220

Ala Leu Ala Thr Ala Gly Thr Lys Glu Val Ala Ile Thr Glu Leu Asp
225                 230                 235                 240

Ile Ala Gly Ala Ser Ser Thr Asp Tyr Val Asn Val Lys Ala Cys
                245                 250                 255

Leu Asn Gln Pro Lys Cys Val Gly Ile Thr Val Trp Gly Val Ser Asp
            260                 265                 270

Lys Asp Ser Trp Arg Ser Asp Asp Thr Pro Leu Leu Phe Asp Ser Asn
        275                 280                 285

Tyr Asn Pro Lys Pro Ala Tyr Asn Ala Ile Thr Asp Ala Leu
    290                 295                 300

<210> SEQ ID NO 10
<211> LENGTH: 978
<212> TYPE: DNA
<213> ORGANISM: Artificial Sequence
<220> FEATURE:
<223> OTHER INFORMATION: Synthetic xylanase SynXyn80

<400> SEQUENCE: 10
atgaagctca gctcgttcct ctacaccgcc agcctcgtcg ccgctatccc taccgccatc     60
gagccccgac aggccgctgc cagcatcgac gccaagttca aggcccacgg caagaagtac    120
ttcggcaaca ttgccgacca gtacacgctc accaagaacc ccaagaccgc cgccatcatc    180
aaggccgact tcggccagct cacccccgag aacagcatga gtgggacgc cacccgagccc    240 agccgaggca agttcaactt cggcggcagc gactacctcg tcaacttcgc caagcagaac    300
aacaagctca tccgcggcca caccctcgtc tggcacagcc agctcccgtc ctgggtccag    360
aacatcaacg acaagaacac cctcacccag gtcatgaaga accacatcac caccgtcatg    420
agccgctaca agggcaagat ctacgcctgg gacgtcgtca cgagatcttc aacgaggac    480 ggcacccctcc gcaacagcgt cttttacaac gtcctgggcg aggacttcgt ccgcattgcc    540
ttcgagactg cccgagccgc cgaccccaac gccaagctct acatcaacga ctacaacctc    600
gacagcgcca actacgccaa gaccaagggc atggtcagcc acgtcaagaa gtggatcgcc    660

```
gagggcatcc ccatcgacgg catcggctct cagactcacc tcggcgctgg cggcggcgct      720
ggcgtctctg gcgctctcaa cgccctcgcc accgccggca ccaaggaggt cgccatcacc      780
gagctggaca ttgctggcgc tagcagcacc gactacgtca acgtcgtcaa ggcctgcctc      840
aaccagccca gtgcgtcgg catcaccgtc tggggcgtca cgacaagga cagctggcgc       900 agcgacgaca ccccctgct gttcgacagc aactacaacc ccaagcccgc ctacaacgcc       960
atcacggacg ccctctaa                                                    978
```

```
<210> SEQ ID NO 11
<211> LENGTH: 302
<212> TYPE: PRT
<213> ORGANISM: Artificial Sequence
<220> FEATURE:
<223> OTHER INFORMATION: Synthetic xylanase SynXyn93

<400> SEQUENCE: 11
```

```
Gln Ala Ala Ala Ser Ile Asp Asn Ala Phe Lys Ala His Gly Lys Lys
1               5                   10                  15

Tyr Phe Gly Thr Cys Ala Asp Gln Asp Thr Leu Thr Asn Pro Lys Asn
            20                  25                  30

Val Ala Ile Ile Lys Ala Asp Phe Gly Gln Leu Thr Pro Glu Asn Ser
        35                  40                  45

Met Lys Trp Asp Ala Thr Glu Pro Ser Gln Gly Lys Phe Asn Phe Gly
    50                  55                  60

Gly Ala Asp Tyr Leu Val Asn Phe Ala Lys Gln Asn Gly Lys Leu Ile
65                  70                  75                  80

Arg Gly His Thr Leu Val Trp His Gly Gln Leu Pro Ser Trp Val Gln
                85                  90                  95

Asn Ile Asn Asp Lys Asn Thr Leu Thr Lys Val Met Lys Asn His Ile
            100                 105                 110

Thr Thr Val Met Ser Arg Tyr Lys Gly Lys Ile Tyr Ala Trp Asp Val
        115                 120                 125

Val Asn Glu Ile Phe Asn Glu Asp Gly Thr Leu Arg Asn Ser Val Phe
    130                 135                 140

Tyr Asn Val Leu Gly Glu Asp Phe Val Arg Ile Ala Phe Glu Thr Ala
145                 150                 155                 160

Arg Ala Ala Asp Pro Asn Ala Lys Leu Tyr Ile Asn Asp Tyr Asn Leu
                165                 170                 175

Asp Ser Ala Asn Tyr Ala Lys Thr Lys Gly Met Val Ser His Val Lys
            180                 185                 190

Lys Trp Ile Ala Glu Gly Ile Pro Ile Asp Gly Ile Gly Ser Gln Thr
        195                 200                 205

His Leu Gly Ala Gly Gly Ala Gly Val Ala Gly Ala Leu Asn Ala
    210                 215                 220

Leu Ala Ala Ala Gly Val Ser Glu Val Ala Ile Thr Glu Leu Asp Ile
225                 230                 235                 240

Ala Gly Ala Ser Ser Asn Asp Tyr Val Asn Val Val Lys Ala Cys Leu
                245                 250                 255

Asn Glu Pro Lys Cys Val Gly Ile Thr Val Trp Gly Val Ser Asp Lys
            260                 265                 270

Asp Ser Trp Arg Ser Asp Asp Asn Pro Leu Leu Phe Asp Ser Asn Tyr
        275                 280                 285

Lys Pro Lys Ala Ala Tyr Asn Ala Ile Ile Asp Ala Leu Arg
    290                 295                 300
```

-continued

```
<210> SEQ ID NO 12
<211> LENGTH: 978
<212> TYPE: DNA
<213> ORGANISM: Artificial Sequence
<220> FEATURE:
<223> OTHER INFORMATION: Synthetic xylanase SynXyn93

<400> SEQUENCE: 12
atgaagctca gctcgttcct ctacaccgcc agcctcgtcg ctgccatccc taccgctatc      60
gagccccgac aggctgctgc cagcatcgac aacgccttca aggcccacgg caagaagtac     120
ttcggcactt gcgccgacca ggacacgctc accaacccca agaacgtcgc catcatcaag     180
gccgacttcg gccagctcac ccccgagaac agcatgaagt gggacgccac cgagcccagc     240
cagggcaagt tcaactttgg cggcgctgac tacctcgtca acttcgccaa gcagaacggc     300
aagctcatcc gcgccacac cctcgtctgg cacggccagc tccctagctg ggtccagaac      360
atcaacgaca gaacaccct gaccaaggtc atgaagaacc acatcaccac cgtcatgagc      420
cgctacaagg gcaagatcta cgcctgggac gtcgtcaacg agatcttcaa cgaggacggc     480
accctccgca acagcgtctt ttacaacgtc ctgggcgagg acttcgtccg cattgccttc     540
gagactgccc gagccgccga ccccaacgct aagctctaca tcaacgacta caacctcgac     600
agcgccaact acgccaagac caagggcatg gtcagccacg tcaagaagtg gatcgccgag     660
ggcatcccca tcgacggcat cggcagccag actcaccttg gcgctggcgg cggcgctggc     720
gttgctggcg ctctcaacgc tctggccgct gccggcgtca gcgaggtcgc catcaccgag     780
ctggacattg ctggcgctag cagcaacgac tacgtcaacg tcgtcaaggc ctgcctcaac     840
gagcccaagt gcgtcggcat caccgtctgg ggcgtcagcg acaaggacag ctggcgcagc     900
gacgacaacc ccctcctctt cgactccaac tacaagccca aggccgccta caacgccatc     960
atcgacgccc tccgctaa                                                   978
```